United States Patent [19]

Aristoff

[11] 4,420,632

[45] Dec. 13, 1983

[54] COMPOSITION AND PROCESS

[75] Inventor: Paul A. Aristoff, Portage, Mich.

[73] Assignee: The Upjohn Company, Kalamazoo, Mich.

[21] Appl. No.: 219,175

[22] Filed: Dec. 22, 1980

Related U.S. Application Data

[63] Continuation-in-part of Ser. No. 140,547, Apr. 15, 1980, abandoned.

[51] Int. Cl.³ .................... C07C 177/00; C07C 57/26
[52] U.S. Cl. .................................. 560/119; 260/404;
562/466; 562/501; 260/404.5; 564/88; 564/89;
260/408; 564/91; 564/96; 260/410; 564/97;
564/98; 260/410.9 R; 564/99; 564/152;
260/413; 564/158; 564/159; 260/464; 564/172;
564/188; 260/465 D; 564/428; 564/454;
424/263; 568/633; 568/734; 424/275; 568/819;
424/285; 424/305; 424/308; 424/317; 424/320;
424/321; 424/324; 424/325; 424/330; 424/343;
542/421; 542/429; 549/79; 549/501; 560/12;
560/39; 560/45; 560/56; 562/501; 562/427;
562/444; 562/455
[58] Field of Search .................... 560/119, 56, 45, 12,
560/39; 562/501, 466, 455, 464, 427; 564/152,
158, 172, 188, 159, 87, 88, 89, 91, 96, 97, 98, 99,
454, 428; 260/404, 404.5, 408, 410, 410.9 R,
413, 465 D, 464; 568/633, 734, 819; 542/421,
429; 549/79, 501

[56] References Cited

U.S. PATENT DOCUMENTS 4,057,571  11/1977  Grudzinskas ...................... 560/121

FOREIGN PATENT DOCUMENTS 2017699  11/1978  United Kingdom ................ 560/119

OTHER PUBLICATIONS

Stork, J. Am. Chem. Soc. 98, 1583 (1976).

*Primary Examiner*—Robert Gerstl
*Attorney, Agent, or Firm*—L. Ruth Hattan; Robert A. Armitage

[57] ABSTRACT

The present specification provides novel analogs of carbacyclin ($CBA_2$), 6a-carba-prostacyclin (6a-carba-$PGI_2$), which have pronounced prostacyclin-like pharmacological activity, e.g., as platelet antiaggregatory agents. Specifically the novel chemical analogs of $CBA_2$ are those substituted by fluoro (C-5), alkyl (C-9), interphenylene (C-5), and methano (C-6a,9). Further provided are benzindene analogs of $CBA_2$ and substituted forms thereof, i.e., 9-deoxy-2',9-methano (or 2',9-metheno)-3-oxa-4,5,6-trinor-3,7-(1',3'-interphenylene)-$PGF_1$ compounds. Also provided are a variety of novel chemical intermediates, e.g., substituted bicyclo[3.3.0]octane intermediates, and chemical process utilizing such intermediates which are useful in the preparation of the novel $CBA_2$ analogs.

6 Claims, No Drawings

COMPOSITION AND PROCESS

CROSS REFERENCE TO RELATED APPLICATION

This application is a continuation-in-part of Application Ser. No. 140,547, filed Apr. 15, 1980, now abandoned.

DESCRIPTION

BACKGROUND OF THE INVENTION

The present invention relates to novel compositions of matter and novel processes for preparing these compositions of matter. Moreover, there are provided novel methods by which certain of these novel compositions of matter are employed for pharmacologically useful purposes. Further there are provided novel chemical intermediates for preparing these compositions of matter.

The present invention is specifically concerned with novel analogs of prostacyclin or $PGI_2$. Specifically, the present invention is concerned with analogs of carbacyclin modified at the C-5 or C-9 position, e.g., C-5 interphenylene analogs of carbacyclin, 5-fluoro analogs of carbacyclin, $9\beta$-alkyl analogs of carbacyclin, C-6a,9 tricyclic (cyclopropyl) analogs of carbacyclin, and combinations thereof as well as novel benzindene analogs thereof.

Prostacyclin is an endogenously produced compound in mammalian species, being structurally and biosynthetically related to the prostaglandins (PG's). In particular, prostacyclin exhibits the structure and carbon atom numbering of formula I when the C-5,6 positions are unsaturated. For convenience, prostacyclin is often referred to simply as "$PGI_2$". Carbacyclin, 6a-carba-$PGI_2$, exhibits the structure and carbon atom numbering indicated in formula II when the C-5,6 positions are unsaturated. Likewise, for convenience, carbacyclin is referred to simply as "$CBA_2$".

A stable partially saturated derivative of $PGI_2$ is $PGI_1$ or 5,6-dihydro-$PGI_2$ when the C-5,6 positions are saturated, depicted with carbon atom numbering in formula I when the C-5,6 positions are saturated. The corresponding 5,6-dihydro-$CBA_2$ is $CBA_1$, depicted in formula II.

As is apparent from inspection of formulas I and II, prostacyclin and carbacyclin may be trivially named as derivatives of PGF-type compounds, e.g., $PGF_{2\alpha}$ of formula III. Accordingly, prostacyclin is trivially named 9-deoxy-6,9α-epoxy-(5Z)-5,6-didehydro-$PGF_1$ and carbacyclin is named 9-deoxy-6,9α-methano-(5E)-5,6-didehydro-$PGF_1$. For description of prostacyclin and its structural identification, see Johnson, et. al., Prostaglandins 12:915 (1976).

For convenience, the novel prostacyclin or carbacyclin analogs will be referred to by the trivial, art-recognized system of nomenclature described by N. A. Nelson, J. Med. Chem. 17:911 (1974) for prostaglandins. Accordingly, all of the novel prostacyclin derivatives herein will be named as 9-deoxy-$PGF_1$-type compounds, $PGI_2$ derivatives, or preferably as $CBA_1$ or $CBA_2$ derivatives.

In the formulas herein, broken line attachments to a ring indicate substituents in the "alpha" (α) configuration, i.e., below the plane of said ring. Heavy solid line attachments to a ring indicate substituents in the "beta" (β) configuration, i.e., above the plane of said ring. The use of wavy lines ($\sim$) herein will represent attachment of substituents in the alpha or beta configuration or attached in a mixture of alpha and beta configurations. Alternatively wavy lines will represent either an E or Z geometric isomeric configuration or the mixture thereof.

A side chain hydroxy at C-15 in the formulas herein is in the S or R configuration as determined by the Cahn-Ingold-Prelog sequence rules, J. Chem. Ed. 41:16 (1964). See also Nature 212:38 (1966) for discussion of the stereochemistry of the prostaglandins which discussion applies to the novel prostacyclin or carbacyclin analogs herein. Molecules of prostacyclin and carbacyclin each have several centers of asymmetry and therefore can exist in optically inactive form or in either of two enantiomeric (optically active) forms, i.e., the dextrorotatory and laveorotatory forms. As drawn, the formula for $PGI_2$ corresponds to that endogenously produced in the mammalian species. In particular, refer to the stereochemical configuration at C-8 (α), C-9 (α), C-11 (α) and C-12 (β) of endogenously produced prostacyclin. The mirror image of the above formula for prostacyclin represents the other enantiomer. The racemic form of prostacyclin contains equal numbers of both enantiomeric molecules.

For convenience, reference to prostacyclin and carbacyclin will refer to the optically active form thereof. Thus, with reference to prostacyclin, reference is made to the form thereof with the same absolute configuration as that obtained from the mammalian species.

The term "prostacyclin-type" product, as used herein, refers to any cyclopentane derivative herein which is useful for at least one of the same pharmacological purposes for which prostacyclin is employed. A formula as drawn herein which depicts a prostacyclin-type product or an intermediate useful in the preparation thereof, represents that particular stereoisomer of the prostacyclin-type product which is of the same relative stereochemical configuration as prostacyclin obtained from mammalian tissues or the particular stereoisomer of the intermediate which is useful in preparing the above stereoisomer of the prostacyclin type product.

The term "prostacyclin analog" or "carbacyclin analog" represents that stereoisomer of a prostacyclin-type product which is of the same relative stereochemical configuration as prostacyclin obtained from mammalin tissues or a mixture comprising stereoisomer and the enantiomers thereof. In particular, where a formula is used to depict a prostacyclin type product herein, the term "prostacyclin analog" or "carbacyclin analog" refers to the compound of that formula or a mixture comprising that compound and the enantiomer thereof.

PRIOR ART

Carbacyclin and closely related compounds are known in the art. See Japanese Kokia 63,059 and 63,060, also abstracted respectively as Derwent Farmdoc CPI Numbers 48154B/26 and 48155B/26. See also British published specifications 2,012,265 and German Offenlegungsschrift 2,900,352, abstracted as Derwent Farmdoc CPI Number 54825B/30. See also British published applications 2,017,699, 2,014,143 and 2,013,661.

The synthesis of carbacyclin and related compounds is also reported in the chemical literature, as follows: Morton, D. R., et al., J. Organic Chemistry, 44:2880 (1979); Shibasaki, M., et al. Tetrahedron Letters, 433–436 (1979); Kojima, K., et al., Tetrahedron Letters, 3743–3746 (1978); Nicolaou, K. C., et al., J. Chem. Soc., Chemical Communications, 1067–1068 (1978); Sugie A., et al., Tetrahedron Letters 2607–2610 (1979); Shibasaki, M., Chemistry Letters, 1299–1300 (1979), and Hayashi, M., Chem. Lett. 1437–40 (1979); and Li, Tsung-tee, "A Facial Synthesis of 9(0)-Methano-prostacyclin", Abstract No. 378, (Organic Chemistry), and P. A. Aristoff, "Synthesis of 6a-Carbaprostacyclin $I_2$", Abstract No. 236 (Organic Chemistry) both at Abstract of Papers (Part II) Second Congress of the North American Continent, San Francisco, Calif. (Las Vegas, Nev.), USA, 24–29 August 1980.

7-Oxo and 7-hydroxy-$CBA_2$ compounds are apparently disclosed in U.S. Pat. No. 4,192,891. 19-Hydroxy-$CBA_2$ compounds are disclosed in U.S. Ser. No. 054,811, filed July 5, 1979. $CBA_2$ aromatic esters are disclosed in U.S. Pat. No. 4,180,657. 11-Deoxy-$\Delta^{10}$- or $\Delta^{11}$-$CBA_2$ compounds are described in Japanese Kokai 77/24,865, published Feb. 24, 1979.

SUMMARY OF THE INVENTION

The present specification particularly provides:
(a) a carbacyclin intermediate of formula IV, V, VI, VII, VIII, or IX; and
(b) a carbacyclin analog of formula X or XI; wherein g is 0, 1, 2, or 3;
wherein n is one or 2;
wherein $L_1$ is $\alpha$-$R_3$:$\beta$-$R_4$, $\alpha$-$R_4$:$\beta$-$R_3$, or a mixture of $\alpha$-$R_3$:$\beta$-$R_4$ and $\alpha$-$R_4$:$\beta$-$R_3$, wherein $R_3$ and $R_4$ are hydrogen, methyl, or fluoro, being the same or different, with the proviso that one of $R_3$ and $R_4$ is fluoro only when the other is hydrogen or fluoro;
wherein $M_1$ is $\alpha$-OH:$\beta$-$R_5$ or $\alpha$-$R_5$:$\beta$-OH, wherein $R_5$ is hydrogen or methyl;
wherein $M_6$ is $\alpha$-$OR_{10}$:$\beta$-$R_5$ or $\alpha$-$R_5$:$\beta$-$OR_{10}$, wherein $R_5$ is hydrogen or methyl and $R_{10}$ is an acid hydrolyzable protective group;
wherein $R_7$ is
(1) —$C_mH_{2m}$—$CH_3$, wherein m is an integer from one to 5, inclusive,
(2) phenoxy optionally substituted by one, two or three chloro, fluoro, trifluoromethyl, ($C_1$-$C_3$)alkyl, or ($C_1$-$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different,
(3) phenyl, benzyl, phenylethyl, or phenylpropyl optionally substituted on the aromatic ring by one, two or three chloro, fluoro, trifluoromethyl, ($C_1$-$C_3$)alkyl, or ($C_1$-$C_3$)alkoxy, with the proviso that no more than two substituents are other than alkyl,
(4) cis—CH═CH—$CH_2$—$CH_3$,
(5) —$(CH_2)_2$—CH(OH)—$CH_3$, or
(6) —$(CH_2)_3$—CH═C($CH_3$)$_2$;
wherein —C($L_1$)—$R_7$ taken together is
(1) ($C_4$-$C_7$)cycloalkyl optionally substituted by one to 3 ($C_1$-$C_5$) alkyl;
(2) 2-(2-furyl)ethyl,
(3) 2-(3-thienyl)ethoxy, or
(4) 3-thienyloxymethyl;
wherein $R_8$ is hydroxy, hydroxymethyl, or hydrogen;
wherein $R_{15}$ is hydrogen or fluoro;
wherein $R_{16}$ is hydrogen or $R_{16}$ and $R_{17}$ taken together are —$CH_2$— or $R_{16}$ and $R_{47}$ taken together form a second valence bond between C-6a and C-9 or are —$CH_2$—;
wherein $R_{17}$ is as defined above or is
(1) hydrogen, or
(2) ($C_1$-$C_4$)alkyl;
wherein $R_{18}$ is hydrogen, hydroxy, hydroxymethyl, —$OR_{10}$ or —$CH_2OR_{10}$, wherein $R_{10}$ is an acid-hydrolyzable protective group; wherein
(1) $R_{20}$, $R_{21}$, $R_{22}$, $R_{23}$, and $R_{24}$ are all hydrogen with $R_{22}$ being either $\alpha$-hydrogen or $\beta$-hydrogen,
(2) $R_{20}$ is hydrogen, $R_{21}$ and $R_{22}$ taken together form a second valence bond betwen C-9 and C-6a, and $R_{23}$ and $R_{24}$ taken together form a second valence bond between C-8 and C-9 or are both hydrogen, or
(3) $R_{22}$, $R_{23}$, and $R_{24}$ are all hydrogen, with $R_{22}$ being either $\alpha$-hydrogen or $\beta$-hydrogen, and
(a) $R_{20}$ and $R_{21}$ taken together are oxo, or
(b) $R_{20}$ is hydrogen and $R_{21}$ is hydroxy, being $\alpha$-hydroxy or $\beta$-hydroxy;
wherein $R_{27}$ is the same as $R_7$ except that —$(CH_2)_2$—CH(OH)—$CH_3$ is —$(CH_2)$—CH($OR_{11}$)—$CH_3$;
wherein $R_{32}$ is hydrogen or $R_{31}$, wherein $R_{31}$ is a hydroxyl hydrogen replacing group;
wherein $R_{33}$ is —CHO or —$CH_2OR_{32}$, wherein $R_{32}$ is as defined above;
wherein $R_{47}$ is as defined above or is
(1) ($C_1$-$C_4$)alkyl, or
(2) —$CH_2OH$;
wherein $X_1$ is
(1) —$COOR_1$, wherein $R_1$ is
(a) hydrogen,
(b) ($C_1$-$C_{12}$)alkyl,
(c) ($C_3$-$C_{10}$)cycloalkyl,
(d) ($C_7$-$C_{12}$)aralkyl,
(e) phenyl, optionally substituted with one, 2 or 3 chloro or ($C_1$-$C_3$)alkyl,
(f) phenyl substituted in the para position by
  (i) —NH—CO—$R_{25}$,
  (ii) —CO—$R_{26}$,
  (iii) —O—CO—$R_{54}$, or
  (iv) —CH═N—NH—CO—$NH_2$ wherein $R_{25}$ is methyl, phenyl, acetamidophenyl, benzamidophenyl, or —$NH_2$; $R_{26}$ is methyl, phenyl, —$NH_2$, or methoxy; and $R_{54}$ is phenyl or acetamidophenyl; inclusive, or
(g) a pharmacologically acceptable cation;
(2) —$CH_2OH$,
(3) —$COL_4$, wherein $L_4$ is
(a) amino of the formula —$NR_{51}R_{52}$, wherein $R_{51}$ and $R_{52}$
(i) hydrogen,
(ii) ($C_1$-$C_{12}$)alkyl,
(iii) $C_3$-$C_{10}$)cycloalkyl,
(iv) ($C_7$-$C_{12}$)aralkyl,
(v) phenyl, optionally substituted with one, 2 or 3 chloro, ($C_1$-$C_3$)alkyl, hydroxy, carboxy, ($C_2$-$C_5$)alkoxycarbonyl, or nitro,
(vi) ($C_2$-$C_5$)carboxyalkyl,
(vii) ($C_2$-$C_5$)carbamoylalkyl,
(viii) ($C_2$-$C_5$)cyanoalkyl,
(ix) ($C_3$-$C_6$)acetylalkyl,
(x) ($C_7$-$C_{11}$)benzoalkyl, optionally substituted by one, 2 or 3 chloro, ($C_1$-$C_3$)alkyl, hydroxy, ($C_1$-$C_3$)alkoxy, carboxy, ($C_2$-$C_5$)alkoxycarbonyl, or nitro,
(xi) pyridyl, optionally substituted by one, 2 or 3 chloro, ($C_1$-$C_3$)alkyl, or ($C_1$-$C_3$)alkoxy,
(xii) ($C_6$-$C_9$)pyridylalkyl optionally substituted by one, 2 or 3 chloro, ($C_1$-$C_3$)alkyl, hydroxy, or ($C_1$-$C_3$)alkyl,
(xiii) ($C_1$-$C_4$)hydroxyalkyl,
(xiv) ($C_1$-$C_4$)dihydroxyalkyl,
(xv) ($C_1$-$C_4$)trihydroxyalkyl, with the further proviso that not more than one of $R_{51}$ and $R_{52}$ is other than hydrogen or alkyl, (b) cycloamino selected from the group consisting of pyrolidino, piperidino, morpholino, piperazino, hexamethyleneimino, pyrrolino, or 3,4-didehydropiperidinyl optionally substituted by one or 2 $(C_1-C_{12})$alkyl of one to 12 carbon atoms, inclusive, (c) carbonylamino of the formula $-NR_{53}COR_{51}$, wherein $R_{23}$ is hydrogen or $(C_1-C_4)$alkyl and $R_{51}$ is other than hydrogen, but otherwise as defined above, (d) sulfonylamino of the formula $-NR_{53}SO_2R_{51}$, wherein $R_{21}$ and $R_{23}$ are as defined in (c), (4) $-CH_2NL_2L_3$, wherein $L_2$ and $L_3$ are hydrogen or $(C_1-C_4)$-alkyl, being the same or different, or the pharmacologically acceptable acid addition salts thereof when $X_1$ is $-CH_2NL_2L_3$, wherein $Y_1$ is trans—$CH=CH-$, cis—$CH=CH-$, $-CH_2CH_2-$, or $-C\equiv C-$; wherein $Z_1$ is (1) $-CH_2-(CH_2)_f-C(R_2)_2$, wherein $R_2$ is hydrogen or fluoro and f is zero, one, 2, or 3, (2) trans—$CH_2-CH=CH-$, (3) $-(Ph)-(CH_2)_g-$, wherein (Ph) is 1,2-, 1,3-, or 1,4-phenylene and g is zero, one, 2, or 3; wherein $Z_4$ is $-CH_2-$ or $-(CH_2)_f-CF_2$, wherein f is as defined above;

with the overall proviso that (1) $R_{15}$, $R_{16}$, and $R_{17}$ are all hydrogen only when $Z_1$ is $-(Ph)-(CH_2)_g-$, and (2) $Z_1$ is $-(Ph)-(CH_2)_g-$ only when $R_{15}$ is hydrogen.

With regard to the divalent substitutents described above (e.g., $L_1$ and $M_1$), these divalent radicals are defined as $\alpha$-$R_i$:$\beta$-$R_j$, wherein $R_i$ represents the substituent of the divalent moiety in the alpha configuration with respect to the plane of the C-8 to C-12 cyclopentane ring and $R_j$ represents the substituent of the divalent moiety in the beta configuration with respect to the plane of the ring. Accordingly, when $M_1$ is defined as $\alpha$-OH:$\beta$-$R_5$, the hydroxy of the $M_1$ moiety is in the alpha configuration, i.e., as in $PGI_2$ above, and the $R_5$ substituent is in the beta configuration.

The carbon atom content of various hydrocarbon-containing moieties is indicated by a prefix designating the minimum and maximum number of carbon atoms in the moiety, i.e., the prefix $(C_i-C_j)$ indicates a moiety of the integer "i" to the integer "j" carbon atoms, inclusive. Thus $(C_1-C_3)$alkyl refers to alkyl of one to 3 carbon atoms, inclusive, or methyl, ethyl, propyl, and isopropyl.

Certain novel prostacyclin analogs herein, i.e., formula X compounds, are all named as $CBA_1$ or $CBA_2$ compounds, respectively, by virtue of the substitution of methylene for oxa in the heterocyclic ring of prostacyclin. $CBA_2$ compounds are those exhibiting the olefinic double bond at C-5,6, while $CBA_1$ compounds are those saturated at C-5,6. Formula XI compounds are named as $PGE_1$ or $PGF_1$ derivatives as hereinafter described.

Novel compounds wherein $Z_1$ is (Ph)-$(CH_2)_g$ are designated inter-o-, inter-m-, or inter-p-phenylene depending on whether the attachment between C-5 and the $-(CH_2)_g-$ moiety is ortho, meta, or para, respectively.

For those compounds wherein g is zero, one, 2 or 3, the carbacyclin analogs so described are further characterized as 2,3,4-trinor-, 3,4-dinor-, or 4-nor, since in this event the $X_1$-terminated side chain contains (not including the phenylene) 2, 3, or 4 carbon atoms, respectively, in place of the five carbon atoms contained in $PGI_2$. The missing carbon atom or atoms are considered to be at the C-4 to C-2 positions such that the phenylene is connected to the C-5 and C-1 to C-3 positions. Accordingly these compounds are named as 1,5-, 2,5-, 3,5-, and 4,5-inter-phenylene-CBA compounds when g is zero, one, 2, or 3, respectively.

Those CBA analogs wherein $Z_1$ is $-CH_2-(CH_2)_f-CF_2-$ are characterized as "2,2-difluoro-" compounds. For those compounds wherein f is zero, 2, or 3, the carbacyclin analogs so described are further characterized as 2-nor, 2a-homo, or 2a,2b-dihomo, since in this event the $X_1$-terminated side chain contains 4, 6, or 7 carbon atoms, respectively, in place of the five carbon atoms contained in $CBA_2$. The missing carbon atom is considered to be at the C-2 position such that the C-1 carbon atom is connected to the C-3 position. The additional carbon atom or atoms are considered as though they were inserted between the C-2 and C-3 positions. Accordingly these additional carbon atoms are referred to a C-2a and C-2b, counting from the C-2 to the C-3 position.

Those CBA analogs wherein $Z_1$ is trans—$CH_2-CH=CH-$ are described as "trans-2,3-didehydro-CBA" compounds.

Those novel compounds where n is 2 are further characterized as 7-a-homo-CBA compounds by virtue of the cyclohexyl ring replacing the heterocyclic ring of prostacyclin.

Further, the novel compounds are named as 9$\beta$-alkyl-CBA compounds when $R_{17}$ is alkyl.

When $R_{16}$ and $R_{17}$ taken together are $-CH_2-$(methylene), the novel compounds so described are "6a$\beta$,9$\beta$-methano-CBA" compounds by vitrue of the methylene bridge between C-6a and C-9.

When $R_{15}$ is fluoro, "5-fluoro-CBA" compounds are described.

The formula XI CBA analogs wherein $R_{20}$, $R_{21}$, $R_{22}$, $R_{23}$, and $R_{24}$ are all hydrogen with $R_{22}$ being $\beta$-hydrogen are characterized as "9-deoxy-2',9$\alpha$-methano-3-oxa-4,5,6-trinor-3,7-(1',3'-inter-phenylene)-$PGF_1$" compounds. Corresponding compounds wherein $R_{22}$ is $\alpha$-hydrogen are characterized as "9-deoxy-2',9$\beta$-methano-3-oxa-4,5,6-trinor-3,7-(1',3'-inter-phenylene)-$PGF_1$" compounds. CBA analogs wherein $R_{20}$, $R_{23}$, and $R_{24}$ are all hydrogen and $R_{21}$ and $R_{22}$ taken together form a valence bond between C-9 and C-6a are characterized as "9-deoxo-2',9-metheno-3-oxo-4,5,6-trinor-3,7-(1',3'-inter-phenylene)-$PGE_1$" compounds. CBA analogs wherein $R_{20}$ is hydrogen and $R_{21}$ and $R_{22}$ taken together form a second valence bond between C-9 and C-6a and $R_{23}$ and $R_{24}$ taken together form a second valence bond between C-7 and C-8 are characterized as "9-deoxo-2',9-methano-3-oxa-4,5,6-trinor-3,7-(1',3'-inter-phenylene)-7,8-didehydro-$PGE_1$" compounds. The formula XI CBA analogs wherein $R_{22}$, $R_{23}$, and $R_{24}$ are all hydrogen and $R_{20}$ and $R_{21}$ taken together are oxo are characterized as "6a-oxo-9-deoxy-2',9$\alpha$-methano-3-oxa-4,5,6-trinor-3,7-(1',3'-inter-phenylene)-$PGF_1$" or "6a-oxo-9-deoxy-2',9$\beta$-methano-3-oxa-4,5,6-trinor-3,7-(1',3'-interphenylene)-$PGF_1$" depending on whether $R_{22}$ is $\alpha$-hydrogen or $\beta$-hydrogen, respectively. Formula XI CBA analogs wherein $R_{20}$, $R_{22}$, $R_{23}$, and $R_{24}$ are all hydrogen and $R_{21}$ is $\alpha$-hydroxy are characterized as "6a$\alpha$-hydroxy-9-deoxy-2',9$\alpha$-methano-3-oxa-4,5,6-trinor-3,7-(1',3'-interphenylene)-$PGF_1$" or "6a$\alpha$-hydroxy-9-deoxy-2',9$\beta$-methano-3-oxa-4,5,6-trinor-3,7-(1',3'-inter-phenylene)-$PGF_1$" compounds depending on whether $R_{22}$ is α-hydrogen or β-hydrogen, respectively. Finally, formula XI TXA analogs wherein $R_{20}$, $R_{22}$, $R_{23}$, and $R_{24}$ are all hydrogen and $R_{21}$ is β-hydroxy are characterized as "6αβ-hydroxy-9-deoxy-2',9β-methano-3-oxa-4,5,6-trinor-3,7(1',3'-inter-phenylene)-PGF$_1$" or "6αβ-hydroxy-9-deoxy-2',9α-methano-3-oxa-4,5,6-trinor-3,7-(1',3'-interphenylene)-PGF$_1$" compounds depending on whether $R_{22}$ is α-hydrogen or β-hydrogen, respectively. When $Z_4$ is —(CH$_2$)$_f$—CF$_2$ and f is zero, the formula XI CBA analogs are additionally characterized as "2,2-difluoro" compounds. When f is one, 2, or 3, such compounds are additionally characterized as "2a-homo", "2a,2b-dihomo" or "2a,2b,2c-trihomo" compounds.

When $R_5$ is methyl, the carbacyclin analogs are all named as "15-methyl-CBA" compounds. Further, except for compounds wherein $Y_1$ is cis—CH═CH—, compounds wherein the $M_1$ moiety contains as hydroxyl in the beta configuration are additionally named as "15-epi-CBA" compounds.

For the compounds where $Y_1$ is cis—CH═CH—, then compounds wherein the $M_1$ moiety contains an hydroxyl in the alpha configuration are named as "15-epi-CBA" compounds. For a description of this convention of nomenclature for identifying C-15 epimers, see U.S. Pat. No. 4,016,184, issued Apr. 5, 1977, particularly columns 24–27 thereof.

The novel carbacyclin analogs herein which contain —(CH$_2$)$_2$—, cis—CH═CH—, or —C≡C— as the $Y_1$ moiety, are accordingly referred to as "13,14-dihydro", "cis-13", or "13,14-didehydro" compounds, respectively.

When $R_7$ is straight chained —C$_m$H$_{2m}$—CH$_3$, wherein m is as defined above, the compounds so described are named as "19,20-dinor", "20-nor", "20-methyl" or "20-ethyl" compounds when m is one, 2, 4 or 5, respectively. When $R_7$ is branched chain —C$_m$H$_{2m}$—CH$_3$, then the compounds so described are "17-, 18-, 19-, or 20-alkyl" or "17,17-, 17,18-, -17,19-, 17,20-, 18,18-, 18,19-, 18,20-, 19,19-, or 19,20-dialkyl" compounds when m is 4 or 5 and the unbranched portion of the chain is at least n-butyl, e.g., 17,20-dimethyl" compounds are described when m is 5 -(1-methylpentyl).

When $R_7$ is phenyl and neither $R_3$ nor $R_4$ is methyl, the compounds so described are named as "16-phenyl-17,18,19,20-tetranor" compounds. When $R_7$ is substituted phenyl, the corresponding compounds are named as "16-(substituted phenyl)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenyl or 16-(substituted phenyl)-18,19,20-trinor" compounds or "16-methyl-16-phenyl- or 16-(substituted phenyl)-18,19,20-trinor" compounds respectively.

When $R_7$ is benzyl, the compounds so described are named as "17-phenyl-18,19,20-trinor" compounds. When $R_7$ is substituted benzyl, the corresponding compounds are named as "17-(substituted phenyl)-18,19,20-trinor" compounds.

When $R_7$ is phenylethyl, the compounds so described are named as "18-phenyl-19,20-dinor" compounds. When $R_7$ is substituted phenylethyl, the corresponding compounds are named as "18-(substituted phenyl)-19,20-dinor" compounds.

When $R_7$ is phenylpropyl, the compounds so described are named as "19-phenyl-20-nor" compounds. When $R_7$ is substituted phenylpropyl the corresponding compounds are named as "19-(substituted phenyl)-20-nor" compounds.

When $R_7$ is phenoxy and neither $R_3$ nor $R_4$ is methyl, the compounds so described are named as "16-phenoxy-17,18,19,20-tetranor" compounds. When $R_7$ is substituted phenoxy, the corresponding compounds are named as "16-(substituted phenoxy)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenoxy or 16-(substituted phenoxy)-18,19,20-trinor" compounds or "16-methyl-16-phenoxy- or 16-(substituted phenoxy)18,19,20-trinor" compounds, respectively.

When $R_7$ is cis—CH═CH—CH$_2$CH$_3$, the compounds so described are named as "cis-17,18-didehydro" compounds.

When $R_7$ is —(CH$_2$)$_2$—CH(OH)—CH$_3$, the compounds so described are named as "19-hydroxy" compounds.

When $R_7$ is —(CH$_2$)$_3$—CH═C(CH$_3$)$_2$, the compounds so described are named as "20-isopropylidene" compounds.

When —C(L$_1$)-R$_7$ is optionally substituted cycloalkyl, 2-(2-furyl)ethyl, 2-(3-thienyl)ethyl, or 3-thienyloxymethyl, the compounds so described are respectively 15-cycloalkyl-16,17,18,19,20-pentanor compounds, 17-(2-furyl)-18,19,20-trinor-CBA compounds, 17-(3-thienyl)-18,19,20-trinor compounds, or 16-(3-thienyl)oxy-17,18,19,20-tetranor compounds.

When at least one of $R_3$ and $R_4$ is not hydrogen then (except for the 16-phenoxy or 16-phenyl compounds discussed above) there are described the "16-methyl" (one and only one of $R_3$ and $R_4$ is methyl), "16,16-dimethyl" ($R_3$ and $R_4$ are both methyl), "16-fluoro" ($R_3$ or $R_4$ is fluoro), "16,16-difluoro" ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $X_1$ is —CH$_2$OH, the compounds so described are named as "2-decarboxy-2-hydroxymethyl" compounds.

When $X_1$ is —CH$_2$NL$_2$L$_3$, the compounds so described are named as "2-decarboxy-2-aminomethyl" or "2-(substituted amino)methyl" compounds.

When $X_1$ is —COL$_4$, the novel compounds herein are named as CBA-type amides. Further, when $X_1$ is —COOR$_1$, the novel compounds herein are named as CBA-type esters and CBA-type salts.

Examples of phenyl esters substituted in the para position (i.e., $X_1$ is —COOR$_1$, $R_1$ is p-substituted phenyl) include p-acetamidophenyl ester, p-benzamidophenyl ester, p-(p-acetamidobenzamido)pheny ester, p-(p-benzamidobenzamido)phenyl ester, p-amidocarbonylaminophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel amides herein (i.e., $X_1$ is —COL$_4$) include the following:

(1) Amides within the scope of alkylamino groups of the formula-NR$_{51}$R$_{52}$ are methylamide, ethylamide, n-propylamide, n-butylamide, n-pentylamide, n-hexylamide, n-heptylamide, n-octylamide, n-nonylamide, n- decylamide, n-undecylamide, and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentyl amide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, and N-ethyl-Ncyclohexylamide. Amides within the scope of aralkylamino are benzylamide, 2-phenyl-ethylamide, and N-methyl-N benzylamide. Amides within the scope of substituted phenylamide are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methyl anilide, p-ethylanilide, t-butylanilide, p-carboxyanilide, p-methoxycarbonyl anilide, p-carboxyanilide and o-hydroxyanilide. Amides within the scope of carboxyalkylamino are carboxyethylamide, carboxypropylamide and carboxymethylamide, carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxy benzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutyl-amide, 3,4,5-trimethoxybenzoylbutylamide, p-hydroxymethylbenzoylbutyl-amide, p-methylbenzoylbutyamide, m-methylbenzoylbutylamide, p-ethyl-benzoylbutyalmide, m-methylbenzoylbutylamide, p-ethylbenzoylbutyl-amide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4-chloro-β-pyridylmethylamide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-chloro-γ-pyridylbutyl-amide. Amides within the scope of hydroxyalkylamino are hydroxymethylamide, β-hydroxyethylamide, β-hydroxypropylamide, γ-hydroxypropylamide, 1-(hydroxymethyl)ethyl-amide, 1-(hydroxymethyl)propylamide, (2-hydroxymethyl)propylamide, and α,α,-dimethyl-hydroxyethylamide. Amides within the scope of dihydroxyalkylamino are dihydroxymethylamide, β,γ-dihydroxypropylamide, 1-(hydroxymethyl)2-hydroxymethylamide, β,γ-dihydroxybutylamide, β,δ-dihydroxybutyl-amide, γ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamino of the formula $-NR_{53}COR_{51}$ are methylcarbonylamide, ethylcarbonylamide, phenylcarbonylamide, and benzylcarbonylamide.

(4) Amides within the scope of sulfonylamino of the formula $-NR_{53}SO_2R_{51}$ are methylsulfonylamide, ethylsufonylamide, phenylsulfonylamide, p-tolylsulfonylamide, benzylsulfonylamide.

Examples of alkyl of one to 12 carbon atoms, inclusive, are methyl, ethyl, propyl, butyl, pentyl, hexyl, heptyl, octyl, nonyl, decyl, undecyl, dodecyl, isomeric forms thereof.

Examples of $(C_3-C_{10})$cycloalkyl which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of $(C_7-C_{12})$aralkyl are benzyl, 2-phenylethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclsive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of $(C_5-C_7)$cycloalkyl optionally substituted by $(C_1-C_4)$alkyl are cyclobutyl, 1-propylcyclobutyl, 1-butylcyclobutyl, 1-pentylcyclobutyl, 2-methylcyclobutyl, 2-propylcyclobutyl, 3-ethylcyclobutyl, 3-propylcyclobutyl, 2,3,4-triethylcyclobutyl, cyclopentyl, 2,2-dimethylcyclopentyl, 3-ethylcyclopentyl, 3-propylcyclopentyl, 3-butylcyclopentyl, 3-tert-butylcyclopentyl, 1-methyl-3-propylcyclopentyl, 2-methyl-3-propylcyclopentyl, 2-methyl-4-propylcyclopentyl, cyclohexyl, 3-ethylcyclohexyl, 3-isopropylcyclohexyl, 4-methylcyclohexyl, 4-ethylcyclohexyl, 4-propylcyclohexyl, 4-butylcyclohexyl, 4-tert-butylcyclohexyl, 2,6-dimethylcyclohexyl, 2,2-dimethylcyclohexyl, 2,6-dimethyl-4-propylcyclohexyl, and cycloheptyl.

Examples of substituted phenoxy, phenylmethyl, phenylethyl, or phenylpropyl of the $R_7$ moiety are (o-, m-, or p-)tolyl, (o-, m-, or p-)ethylphenyl, 4-ethyl-o-tolyl, 5-ethyl-m-tolyl, (o-, m-, or p-)propylphenyl, 2-propyl-(m- or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro(m- or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)-chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-)chloro-2-fluorophenyl, (o-, m-, or p-)trifluoromethylphenyl, (o-, m-, or p-)methoxyphenyl, (o-, m-, or p-)ethoxyphenyl, (4- or 5-)chloro-2-methoxyphenyl, 2,4-dichloro-(4- or 6-)methylphenyl, (o-, m-, or p-)tolyloxy, (o-, m-, or p-)ethylphenyloxy, 4-ethyl-o-tolyloxy, 5-ethyl-m-tolyloxy, (o-, m-, or p-)propylphenoxy, 2-propyl-(m- or p-)tolyloxy, 4-isopropyl-2,6-xylyloxy, 3-propyl-4-ethylphenyloxy, (2,3,4-, 2,3,5-, 2,3,6-, or 2,4,5-)trimethylphenoxy, (o-, m-, or p-)fluorophenoxy, 2-fluoro-(m- or p-)tolyloxy, 4-fluoro-2,5-xylyloxy, (2,4-, 2,5-, 2,6-, 3,4-, or 3,5-)difluorophenoxy, (o-, m-, or p-)-chlorophenoxy, 2-chloro-p-tolyloxy, (3, 4, 5, or 6-)chloro-o-tolyloxy, 4-chloro-2-propylphenoxy, 2-isopropyl-4-chlorophenoxy, 4-chloro-3,5-xylyloxy, (2,3-, 2,4-, 2,5-, 2,6-, 3,4-, or 3,5-)dichlorophenyloxy, 4-chloro-3-fluorophenoxy, (3- or 4-)chloro-2-fluorophenoxy, (o-, m-, or p-)trifluoromethylphenoxy, (o-, m-, or p-)methoxyphenoxy, (o-, m-, or p-)ethoxyphenoxy, (4- or 5-)chloro-2-methoxyphenoxy, 2,4-dichloro-(5- or 6-)methylphenoxy, (o-, m-, or p-)tolylmethyl, (o-, m-, or p-)ethylphenyl methyl, 4-ethyl-o-tolylmethyl, 5-ethyl-m-tolylmethyl, (o-, m-, or p-)propylphenylmethyl, 2-propyl-(m- or p-)tolylmethyl, 4-isopropyl-2,6-xylylmethyl, 3-propyl-4-ethylphenylmethyl, (2,3,4-, 2,3,5-, 2,3,6-, or 2,4,5-)trimethylphenylmethyl, (o-, m-, or p-)fluorophenylmethyl, 2-fluoro-(m- or p-)tolylmethyl, 4-fluoro-2,5-xylylmethyl, (2,4-, 2,5-, 2,6-, 3,4-, or 3,5-)difluorophenyl, (o-, m-, or p-)chlorophenylmethyl, 2-chloro-p-tolylmethyl, (3, 4, 5, or 6-)chloro-o-tolylmethyl, 4-chloro-2-propylphenylmethyl, 2-isopropyl-4-chlorophenylmethyl, 4-chloro-3,5-xylylmethyl, (2,3-, 2,4-, 2,5-, 2,6-, 3,4-, or 3,5-)dichlorophenylmethyl, 4-chloro-3-fluorophenylmethyl, (3- or 4-)chloro-2-fluorophenylmethyl, (o-, m-, or p-)trifluoromethylphenylmethyl, (o-, m-, or p-)methoxyphenylmethyl, (o-, m-, or p-)ethoxyphenylmethyl, (4- or 5-)chloro-2-methoxyphenylmethyl, and 2,4-dichloro-(4- or 6-)methoxyphenylmethyl.

The novel CBA analogs disclosed herein produce certain prostacyclin-like pharmacological responses.

Accordingly, the novel formula X and XI CBA analogs are used as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys). In particular, these compounds have useful application as antithrombotic agents, anti-ulcer agents, and anti-asthma agents, as indicated below:

(a) Platelet Aggregation Inhibition

These novel CBA analogs disclosed herein are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, to treat peripheral vascular diseases, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg per kg of body weight per day are used, the exact dose depending on the age, weight, and condition of the patient or animal, and on the frequency and route of administration.

The preferred dosage form for these compounds is oral, although other non-parenteral routes (e.g., buccal, rectal, sublingual) are likewise employed in preference to parenteral routes. Oral dosage forms are conventionally formulated (tablets, capsules, et cetera) and administered 2-4 times daily. Doses in the range of about 0.05 to 100 mg per kg of body weight per day are effective.

The addition of these compounds to whole blood provides in vitro applications such as storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation therapy. In vitro applications utilize a dose of 0.001–1.0 μg per ml of whole blood. For treatment of peripheral vascular diseases, see U.S. Pat. No. 4,103,026.

(b) Gastric Secretion Reduction

These novel CBA analogs disclosed herein are also useful in mammals, including man and certain useful animals, e.g., dogs and pigs, to reduce and control gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg to about 20 μg per kg of body weight per minute, or in a total daily dose by injection or infusion in the range about 0.01 to about 10 mg per kg of body weight per day, the exact dose depending on the age, weight, and condition of the patient or animal, and on the frequency and route of administration.

Preferably, however, these novel compounds are administered orally or by other non-parenteral routes. As employed orally, one to 6 administrations daily in a dosage range of about 1.0 to 100 mg per kg of body weight per day is employed. Once healing of the ulcers has been accomplished the maintenance dosage required to prevent recurrence is adjusted downward so long as the patient or animals remains asymptomatic.

(c) NOSAC-Induced Lesion Inhibition

These novel CBA analogs disclosed herein are also useful in reducing the undesirable gastrointestinal effects resulting from systemic administration of anti-inflammatory prostaglandin synthetase inhibitors, and are useful for that purpose by concomitant administration of the prostaglandin derivative and the anti-inflammatory prostaglandin synthetase inhibitor. See Partridge, et al., U.S. Pat. No. 3,781,429, for a disclosure that the ulcerogenic effect induced by certain non-steroidal anti-inflammatory agents in rats is inhibited by concomitant oral administration of certain prostaglandins. Accordingly these novel CBA analogs herein are useful, for example, in reducing the undesirable gastrointestinal effects resulting from systemic administration of indomethacin, phenylbutazone, and aspirin. These are substances specifically mentioned in Partridge, et al. as non-steroidal, anti-inflammatory agents. These are also known to be prostaglandin synthetase inhibitors.

The anti-inflammatory synthetase inhibitor, for example, indomethacin, aspirin, or phenylbutazone is administered in any of the ways known in the art to alleviate an inflammatory conditions, for example, in any dosage regimen and by any of the known routes of systemic administration.

(d) Bronchodilation (Anti-asthma)

These novel analogs disclosed herein are also useful in the treatment of asthma. For example, these compounds are useful as bronchodilators or as inhibitors of mediator-induced bronchoconstriction, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the above use these CBA analogs can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

These compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Suitable means to employ the aerosol inhalation therapy technique are described fully in U.S. Pat. No. 3,868,691, for example.

When $X_1$ is —COOR$_1$, the novel CBA analogs so described are used for the purposes described above in the free acid form, in ester form, or in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity.

Pharmacologically acceptable salts of the novel prostaglandin analogs of this invention for the purposes described above are those with pharmacologically acceptable metal cations, ammonia, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, and tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamine, and the like aliphatic, cycloaliphatic aliphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl) aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts of the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

When $X_1$ is —$CH_2NL_2L_3$, the novel CBA analogs so described are used for the purposes described in either free base or pharmacologically acceptable acid addition salt form.

The acid addition salts of the 2-decarboxy-2-aminomethyl- or 2-(substituted aminomethyl)-CBA analogs provided by this invention are the hydrochlorides, hydrobromides, hydriodides, sulfates, phosphates, cyclohexanesulfamates, methanesulfonates, ethanesulfonates, benzenesulfonates, toluenesulfonates and the like, prepared by reacting the CBA analog with the stoichiometric amount of the acid corresponding to the pharmacologically acceptable acid addition salt.

To obtain the optimum combination of biological response specificity, potency, and duration of activity, certain compounds within the scope of this invention are preferred.

It is preferred that in the $X_1$-terminated side chain for inter-p-phenylene-CBA compounds, g be zero, for inter-m-phenylene-CBA compounds g be zero or one (especially zero), and for inter-o-phenylene CBA compounds g be zero, one or 2 (especially one). Inter-o- and inter-m-phenylene-CBA compounds, especially inter-m-phenylene-CBA compounds are preferred. Moreover when $Z_1$ is —$CH_2$—$(CH_2)_f$—$C(R_2)_2$, f is preferably one and $R_2$ is preferably hydrogen. When $R_{17}$ is $(C_1-C_4)$alkyl, $R_{17}$ is preferably methyl. Further, when the C-12 side chain contains —$C_mH_{2m}$—$CH_3$, it is preferred that m be 3, 4, or 5, most preferably 3. When m is 5, more straight chain isomeric forms are preferred, especially methyl-substituted butyl. Further, it is preferred that, when $R_7$ is aromatic, $R_7$ be phenoxy, phenyl, or benzyl, including substituted forms thereof. For those compounds wherein $R_7$ is substituted phenoxy or phenylalkyl, it is preferred there be only one or 2 substituents selected from the group consisting of chloro, fluoro, or trifluoromethyl. Further, for those compounds wherein $R_7$ is aromatic, it is preferred that $R_3$ and $R_4$ both be hydrogen.

Most expecially preferred for biological potency are formula X $CBA_2$ analogs exhibiting the same C-5 isomeric configuration as $CBA_2$ itself.

Especially preferred are those compounds which satisfy two or more of the above preferences. Further, the above preferences are expressly intended to describe the preferred compounds within the scope of any generic formula of novel CBA analogs disclosed herein.

Those protective groups within the scope of $r_{10}$ are any group which replaces a hydroxy hydrogen and is neither attacked by nor is reactive to the reagents used in the transformations used herein as a hydroxy is and which is subsequently replaceable by acid hydrolysis with hydrogen in the preparation of the prostaglandin-type compounds. Several such protective groups are known in the art, e.g., tetrahydropyranyl and substituted tetrahydropyranyl. See for reference E. J. Corey, Proceedings of the Robert A. Welch Foundation Conferences on Chemical Research, XII Organic Synthesis, pgs. 51–79 (1969). Those blocking groups which have been found useful include:

(a) tetrahydropyranyl;
(b) tetrahydrofuranyl;
(c) a group of the formula —$C(OR_{11})(R_{12})$—$CH(R_{13})(R_{14})$, wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2 or 3 alkyl of one to 4 carbon atoms, inclusive, or when $R_{12}$ and $R_{13}$ are taken together —$(CH_2)_a$—or when $R_{12}$ are $R_{13}$ are taken together —$(CH_2)_b$—O—$(CH_2)_c$, wherein a is 3, 4, or 5 and b is one, 2, or 3, and c is one, 2, or 3, with the proviso that b plus c is 2, 3, or 4, with the further proviso that $R_{12}$ and $R_{13}$ may be the same or different, and wherein $R_{14}$ is hydrogen or phenyl; and (d) silyl groups according to $R_{28}$, as qualified hereinafter.

When the protective group $R_{10}$ is tetrahydropyranyl, the tetrahydropyranyl ether derivative of any hydroxy moieties of the CBA-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20°–50° C.

When the protective group is tetrahydrofuranyl, 2,3-dihydrofuran is used, as described in the preceding paragraph, in place of the 2,3-dihydropyran.

When the protective group is of the formula —$C(OR_{11})(R_{12})$—$CH(R_{13})(R_{14})$, wherein $R_{11}$, $R_{12}$, $R_{13}$, and $R_{14}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., J. American Chemical Society 89, 3366 (1967). The reaction conditions for such vinyl ethers and unsaturated compounds are similar to those for dihydropyran above.

$R_{28}$ is a silyl protective group of the formula —$Si(G_1)_3$. In some cases, such silylations are general, in that they silylate all hydroxyls of a molecule, while in other cases they are selective, in that while one or more hydroxyls are silylated, at least one other hydroxyl remains unaffected. For any of these silylations, silyl groups within the scope of —$Si(G_1)_3$ include trimethylsilyl, dimethylphenylsilyl, triphenylsilyl, t-butyldimethylsilyl, or methylphenylbenzylsilyl. With regard to $G_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-naphthylmethyl, and 2-(α-naphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

These silyl groups are known in the art. See for example, Pierce "Silylation of Organic Compounds," Pierce Chemical Company, Rockford, Ill. (1968). When silylated products of the charts below are intended to be subjected to chromatographic purification, then the use of silyl groups known to be unstable to chromatography (e.g. trimethylsilyl) is to be avoided. Further, when silyl groups are to be introduced selectively, silylating agents which are readily available and known to be useful in selective silylations are employed. For example, t-butyldimethylsilyl groups are employed when selective introduction is required. Further, when silyl groups are to be selectively hydrolyzed in the presence of protective groups according to $R_{10}$ or acyl protective groups, then the use of silyl groups which are readily available and known to be easily hydrolyzable with tetra-n-butylammonium fluoride are employed. A particularly useful silyl group for this purpose is t-butyldimethylsilyl, while other silyl groups (e.g. trimethylsilyl) are not employed when selective introduction and/or hydrolysis is required.

The protective groups as defined by $R_{10}$ are otherwise removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

$R_{31}$ is a hydroxy-hydrogen protective group, as indicated above. As such, $R_{31}$ may be an acyl protective group according to $R_9$, an acid hydrolyzable protective group according to $R_{10}$, a silyl protective group according to $R_{28}$, or an arylmethyl hydroxy hydrogen replacing group according to $R_{34}$.

Acyl protective groups according to $R_9$ include:
(a) benzoyl;
(b) benzoyl substituted with one to 5 alkyl of one to 4 carbon atoms, inclusive, or phenylalkyl of 7 to 12 carbon atoms, inclusive, or nitro, with the proviso that not more than two substituents are other than alkyl, and that the total number of carbon atoms in the substituents does not exceed 10 carbon atoms, with the further proviso that the substituents are the same or different;
(c) benzoyl substituted with alkoxycarbonyl of 2 to 5 carbon atoms, inclusive;
(d) naphthoyl;
(e) naphthoyl substituted with one to 9, inclusive, alkyl of one to 4 carbon atoms, inclusive, phenylalkyl of 7 to 10 carbon atoms, inclusive, or nitro, with the proviso that not more than two substituents on either of the fused aromatic rings are other than alkyl and that the total number of carbon atoms in the substituents on either of the fused aromatic rings does not exceed 10 carbon atoms, with the further proviso that the various substituents are the same or different; or
(f) alkanoyl of 2 to 12 carbon atoms, inclusive.

In preparing these acyl derivatives of a hydroxy-containing compound herein, methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g. p-toluenesulfonyl chloride or dicyclohexylcarbodiimide; or alternatively as anhydride of the aromatic acid of the formula $(R_9)OH$, e.g., benzoic anhydride, is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxyl-containing compound in the presence of a hydrogen chloride scavenger, e.g. a tertiary amine such as pyridine, triethylamine or the like. The reaction is carried out under a variety of conditions, using procedures generally known in the art. Generally mild conditions are employed: 0°–60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_9OH$), $(R_9)_2O$, or acyl chlorides ($R_9Cl$): benzoyl; substituted benzoyl, e.g., (2-, 3-, or 4-)methylbenzoyl, (2-, 3-, or 4-)ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, phenyl(2-, 3-, or 4-)toluyl, (2-, 3-, or 4-)phenethylbenzoyl, (2-, 3-, or 4-)nitrobenzoyl, (2,4, 2,5-, or 2,3-)dinitrobenzoyl, 2,3-dimethyl-2-nitrobenzoyl, 4,5-dimethyl-2-nitrobenzoyl, 2-nitro-6-phenylethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g. tert-butyl on both of the ring carbon atoms adjacent to the carbonyl attaching site.

The acyl protective groups, according to $R_9$, are removed by deacylation. Alkali metal carbonate or hydroxide are employed effectively at ambient temperature for this purpose. For example, potassium carbonate or hydroxide in aqueous methanol at about 25° C. is advantageously employed.

$R_{34}$ is defined as any arylmethyl group which replaces the hydroxy hydrogen of the intermediates in the preparation of the various CBA analogs herein which is subsequently replaceable by hydrogen in the processes herein for preparation of these respective prostacyclin analogs, being stable with respect to the various reactions to which $R_{34}$-containing compounds are subjected and being introduced and subsequently removed by hydrogenolysis under conditions which yield substantially quantitative yields of desired products.

Examples of arylmethyl hydroxy-hydrogen replacing groups are
(a) benzyl;
(b) benzyl substituted by one to 5 alkyl of one to 4 carbon atoms, inclusive, chloro, bromo, iodo, fluoro, nitro, phenylalkyl of 7 to 12 carbon atoms, inclusive, with the further proviso that the various substituents are the same or different;
(c) benzhydryl;
(d) benzhydryl substituted by one to 10 alkyl of one to 4 carbon atoms, inclusive, chloro, bromo, iodo, fluoro, nitro, phenylalkyl of 7 to 12 carbon atoms, inclusive, with the further proviso that the various substituents are the same or different on each of the aromatic rings;
(e) trityl;
(f) trityl substituted by one to 15 alkyl of one to 4 carbon atoms, inclusive, chloro, bromo, iodo, fluoro, nitro, phenylalkyl of 7 to 12 carbon atoms, inclusive, with the further proviso that the various substituents are the same or different on each of the aromatic rings.

The introduction of such ether linkages to the hydroxy-containing compounds herein, particularly the benzyl or substituted benzyl ether proceeds by methods known in the art, for example by reaction of the hydroxy-containing compound with the benzyl or substituted benzyl halide (chloride, bromide, or iodide) corresponding to the desired ether. This reaction proceeds in the presence of an appropriate condensing agent (e.g., silver oxide). The mixture is stirred and heated to 50°–80° C. Reaction times of 4 to 20 hours are ordinarily sufficient.

The Charts herein describe the methods whereby the novel intermediates and end products of the present specification are prepared by the novel processes herein. With respect to these charts, g, n, $L_1$, $M_1$, $M_6$, $R_7$, $R_8$, $R_{10}$, $R_{15}$, $R_{16}$, $R_{17}$, $R_{18}$, $R_{20}$, $R_{21}$, $R_{22}$, $R_{23}$, and $R_{24}$, $R_{28}$, $R_{31}$, $X_1$, $Y_1$, $Z_1$, and $Z_4$ are as defined above. $R_{37}$ is the same as $R_{47}$, but other than —$CH_2OH$. $R_{38}$ is —$OR_{31}$, hydrogen, or —$CH_2OR_{31}$, wherein $R_{31}$ is defined as above. $R_{27}$ is the same as $R_7$ except that —$(CH_2)_2$—$CH(OH)$—$CH_3$ is —$(CH_2)_2$—$CH(OR_{10})$—$CH_3$. $R_{37}$ is the same as $R_{17}$, but other than hydrogen. Ac is acetyl. $Z_2$ is the same as $Z_1$ but not —(P-h)—$(CH_2)_g$—. $Z_3$ is the same as $Z_1$, but not trans—$CH_2$—$CH=CH$—.

With respect to Chart A, a method is provided whereby the known formula XXI bicyclic lactone is transformed to the carbacyclin intermediate of formula XXV useful in the preparation of formula X CBA compounds wherein $R_{17}$ is alkyl or $R_{16}$ and $R_{17}$ taken together are methano or a second valence bond between C-6a and C-9. With respect to Chart A, the formula XXI compound is transformed to the formula XXII compound by treatment with the anion of dimethyl methylphosphonate. Methods for such a reaction are known in the art. See Dauben, W. G., et al., JACS, 97:4973 (1975), describing a reaction of this type.

The formula XXII lactol is transformed to the formula XXIII diketone by oxidation methods known in the art. For example, Collins reagent or Jones reagent is employed in this oxidative transformation.

The formula XXIII diketone is cyclized to the formula XXIV compound by an intramolecular Horner-Emmons reaction. The chemical methodology for analogous transformations is known in the art. See Piers, E., et al., Tetrahedron Letters, 3279 (1979) and Clark, R. D., et al., Synthetic Communications 5:1 (1975).

The formula XXIV compound is transformed to the novel formula XXV compound wherein $R_{16}$ is hydrogen and $R_{37}$ is alkyl by treatment with lithium dialkyl cuprate. The lithium dialkyl cuprate is prepared by conventional means, e.g., reaction of anhydrous copper iodide in diethyl ether with an alkyllithium in diethyl ether, and thereafter reacted with the formula XXIV compounds, e.g., in diethyl ether.

The formula XXIV compound is transferred to the novel formula XXV compound wherein $R_{16}$ and $R_{37}$ taken together are methylene (—$CH_2$—) by one of two methods. By the first method, the formula XXV compound is prepared by treatment of the formula XXIV compound with the anion of trimethyloxosulfonium iodide. See for reference E. J. Corey, et al., JACS 87:1353 (1965). By this method, the anion is conveniently generated by treatment of trimethyloxosulfonium iodide in sodium hydride.

By a second method, the formula XXIV compound is converted to the formula XXV compound wherein $R_{16}$ and $R_{37}$ taken together are methylene by first converting the formula XXIV compound to the corresponding formula XXVI hydroxymethyl compound by photochemical addition of methanol (e.g., see G. L. Bundy, Tetr. Lett. 1957, 1975), thereafter treating the resulting hydroxymethyl compound with an excess (e.g., two equivalents) of p-toluenesulfonyl chloride in a tertiary amine base to yield the corresponding formula XXVII tolsylate, and finally treating the resulting formula XXVII tosylate with base (e.g., potassium t-butoxide) to yield the formula XXV cyclopropyl compound.

With respect to Chart B, a method is provided whereby the formula XXXI compound prepared in accordance with methods of Chart A is transformed to the novel $CBA_2$ analogs of formula XXXVI.

The formula XXXI compound is transformed to the formula XXXVI compound by methods known in the art for preparing carbacyclin. See for example, British published applications referred to above. Alternatively, the formula XXXI compound is reacted with formula XXXII compound and thereby successively transformed to the formula XXXIII, formula XXXIV and formula XXXV compounds.

The reaction of the formula XXXI compound employing the formula XXXII compound is accomplished by methods known in the art. See Moersch, G. W., J. Organic Chemistry, 36:1149 (1971) and Mulzer, J., et al., Tetrahedron Letters, 2949 (1978). The formula XXXII reactants are known in the art or are prepared by methods known in the art. See Example 4 describing one such method of preparation of a formula XXXII compound.

The formula XXXIII compound is then transformed to the formula XXXIV compound by decarboxylative dehydration. Procedures for this reaction are known in the art. See Eschenmoser, A., et al., Helv. Chim. Acta. 58:1450 (1975), Hara, S., et al., Tetrahedron Letters, 1545 (1975) and Mulzer, J., et al., Tetradron Letters, 2953 (1978) and 1909 (1979).

Finally, the formula XXXV compound is prepared from formula XXXIV compound by selective desilylation. Such procedures are known in the art and typically employ the use of tetra-n-butyl ammonium fluoride and tetrahydrofuran. See Corey, E. J., et al., JACS 94:6190 (1972).

The formula XXXV compound is transformed to various acids, esters, amides, and amines of a formula XXXVI by methods known in the art. Particularly useful in this regard are methods described in the aforementioned British published specifications describing the preparation of carbacyclin analogs.

The preparation of formula XXXVI compounds from the formula XXXV compounds proceeds by, for example, oxidation to the corresponding carboxylic acid, followed by hydrolysis of any protective groups at the C-11 or C-15 position of the molecule. Such carboxylic acids are then esterified by conventional means or amidized by conventional means. Such amides may, for example, then be reduced to corresponding amines ($X_1$ is —$CH_2NL_2L_3$ by reduction by lithium aluminum hydride. See U.S. Pat. No. 4,073,808. In a preparation of the primary alcohols according to formula XXXVI from the formula XXXV compound, hydrolysis of any protective groups at C-11 or C-15 yields such products directly. Hydrolysis is accomplished by procedures described above, e.g., mild acidic conditions at elevated temperatures.

Chart C provides a method whereby the known formula XLI compounds are transformed to the formula XLIV aldehydes employed in Chart D in the preparation of inter-phenylene-$CBA_2$ compounds therein.

With respect to Chart C, the formula XLII compound is prepared from the formula XLI compounds by reduction. Conventional methods known in the art for the transformation of carboxylic acids to corresponding primary alcohols are employed. For example, one extremely useful conventional means for this reduction is employing lithium aluminum hydride as a reducing agent.

The formula XLIII compound is then prepared from the formula XLII compound by monosilylation. Particularly, formula XLIII compounds are prepared wherein $R_{28}$ represents a relatively stable silyl group, most preferably being t-butyldimethylsilyl or phenyldimethylsilyl. Other silyl groups, particularly trimethyl-silyl (TMS) are not preferred for use in connection with the methods of Chart C.

The formula XLIII monosilyl derivatives are prepared from the formula XLII compound by reacting the formula XLII compounds with about an equal molar amount of the silylating agent. For example, when $R_{28}$ is t-butyldimethylsilyl, a single equivalent of t-butyldimethylsilyl chloride is employed in the transformation. Accordingly, there are prepared both monosilyl derivatives of the formula XLII compound as well as the bis-silyl derivatives corresponding to formula XLII. From this mixture of products, the formula XLIII compound is recovered by conventional means, e.g., column chromatography. Otherwise, the silylation proceeds under conditions conventionally employed for silylating hydroxyl groups. Refer to the discussion hereinabove.

The formula XLIV compound is then prepared from the formula XLIII compound by oxidation of the formula XLIII alcohol to the corresponding aldehyde. Conventional oxidizing agents are employed, e.g., manganese dioxide.

Chart D provides a method whereby the known formula LI ketones are transformed to the formula LX inter-phenylene $CBA_2$ analogs disclosed herein.

In accordance with Chart D the formula LII compound is prepared from the formula LI compound by reduction of the formula LI ketone to the corresponding secondary alcohol. This reduction proceeds by conventional means, employing readily available reducing agents. Accordingly, sodium, potassium, or lithium borohydride is conveniently employed in this reduction.

Thereafter, the formula LII alcohol is transformed to the corresponding mesylate (methanesulfonate). Conventional methods for the transformation of alcohols to corresponding mesylates are employed. Thus, the formula LII alcohol is reacted with methane-sulfonyl chloride in the presence of a tertiary amine (e.g., tri-ethylamine) in the preparation of the formula LIII compound.

Other sulfonyl derivatives corresponding to the formula LII alcohol may be employed in place of the formula LIII compound in the transformations of Chart D. These other sulfonyl derivatives are preferably those derived from readily available sulfonylating reagents, i.e., the corresponding sulfonyl chlorides. One especially important alternative to the formula LIII compound is the tosylate (toluenesulfonate) corresponding to the formula LII compound.

The formula LIII compound, or an alternate sulfonate corresponding thereto, is transformed to the formula LIV compound by treatment with sodium lithium or potassium thiophenoxide. The thiphenoxide is conveniently prepare just prior to the transformation by mixing approximately equal molar amounts of thiophenol and base, e.g., potassium t-butoxide.

This formula LIV compound is then oxidized to the corresponding formula LV compound by oxidation with a readily available oxidizing agent such as m-chloroperbenzoic acid.

The formula LV compound is then condensed with the formula XLIV compound prepared according to Chart C by first treatment of the formula LV compound with a strong base, e.g., n-butyllithium, to generate the anion corresponding to the formula LV compound, treatment of the corresponding anion with the aldehyde of formula XLIV and finally treating the resulting adduct with acetic anhydride to yield the formula LVI acetyl compound.

The formula LVI compound is then transformed to the formula LVII compound by reaction with a sodium amalgam. Methods by which the formula LVII olefin is formed from the formula LV compound are analogous to known methods described by Kocienski, P. J., et al., "Scope and Stereochemistry of an Olefin Synthesis from $\beta$-Hydroxysulphones", JCS Perkin I, 829–834 (1978).

The formula LVII compound is then transformed to the formula LVIII compound by selective hydrolysis of the silyl group according to $R_{28}$. Conventional means for this hydrolysis are employed, e.g., tetra-n-butyl ammonium fluoride. Refer to the discussion above for a discription of this hydrolysis.

The formula LVIII C-5 diastereomers thusly prepared are conveniently purified into (5-E) and (5-Z) isomeric forms. This transformation proceeds by conventional means, e.g., column chromatography.

Thereafter either the (5E) or (5Z) isomer of formula LVIII is transformed to the formula LIX carboxylic acid or ester by conventional oxidation, followed by optional esterification. One especially convenient means of oxidation is employing the Jones reagent, although other oxidizing agents are employed. Esterification then proceeds by methods hereinafter described.

Finally, the formula LX products are prepared from the formula LIX compound by first hydrolyzing the protective groups under acidic conditions, e.g. mixtures of water, tetrahydrofuran, and acetic acid. Thereafter, the formula LIX acids and esters are transformed to various other C-1 derivatives by methods hereinafter described.

One especially convenient means of preparing the formula LX compound as a free carboxylic acid ($X_1$ is —COOH), is by purification of the corresponding methyl ester, followed by saponification under basic conditions (e.g., the treatment with potassium carbonate or sodium or potassium hydroxide).

Chart E provides a method whereby the known formula LXI compound is transformed into formula LXIII intermediate useful in the preparation of the novel $CBA_2$ analogs.

The procedures for the transformation of the formula LXI compound to the formula LXIII compound are analogous to those describing the transformation in Charts A, B, and D of the formula XXI compound to the formula XXXVI and LX compounds (i.e., corresponding to the transformation of formula LXI compound to the formula LXII compound is the transformation in Chart A of the formula XXI compound to the formula XXV compound and corresponding to the transformation of the formula LXII compound to the formula LXIII compound is the transformation in Chart D of the formula LI compound to the formula LX compound.). For convenience, the protective groups $R_{31}$ and $R_{38}$ may be the same or different, although preferably such protective groups are different, whereby the hydrolysis of a protective group according to $R_{31}$ is accomplished in the presence of a protective group according to $R_{38}$.

Chart F then provides a method whereby the formula LXXI compound prepared according to Chart E is transformed to the formula LXXII carbacyclin analog in accordance with the present invention. With respect to Chart F, the formula LXXI compound is transformed to the formula LXXII compound by selective hydrolysis of the protective group according to $R_{31}$. Thereafter, the formula LXXII compound is transformed to formula LXXIII compound by methods known in the art, e.g., oxidation of the formula LXXII primary alcohol to the corresponding aldehyde, Wittig oxylacylating the aldehyde, and reduction of the resulting ketone to the secondary or tertiary alcohol corresponding to $M_1$. For an example of the various transformations employed according to Chart F, see Chart A (part VI) of U.S. Pat. No. 4,107,427, issued Aug. 15, 1978.

Chart G provides a method whereby the novel formula LXXXI intermediate, prepared according to Chart A, is transformed to the formula LXXXVIII and LXXIX isomers of the novel C-6a- and/or C-9-substituted $CBA_2$ analogs.

With respect to Chart G, the formula LXXXIII compound is prepared from the formula LXXXI ketone by a Wittig ω-carboxyalkylation employing a formula LXXXII triphenylphosphonium compound. The Wittig reaction is undertaken under conventional reaction conditions for preparing prostaglandin-type substances. The formula LXXXIII compound is then optionally hydrolyzed to yield the formula X carboxylic acid products or employed in the further transformations of Chart G in ester form.

The formula LXXXIII compound thusly prepared is thereafter preferably separated directly into C-5 isomers of formulas LXXXVIII and LXXXIX (e.g., by chromatographic means followed by hydrolysis of any protective groups at C-11 or C-15 position of the molecule), or is alternatively transformed to the formula LXXXIV ester by conventional esterification techniques, e.g., ethereal diazomethane treatment or treatment with methyl iodide. The formula LXXXIV ester is then reduced to the corresponding primary alcohol by reduction with a suitable reducing agent, e.g., lithium aluminum hydride, by methods known in the art for preparing prostaglandin-type primary alcohols from corresponding prostaglandin esters.

The formula LXXXV compound represents an especially convenient intermediate for the facile separation of the C-5 diastereomers. Accordingly, the formula LXXXV compound may be separated by conventional means of separation of diastereomeric mixtures, e.g., column chromatography, whereby the formula LXXXVI and formula LXXXVII compounds are prepared in isomerically pure form. These primary alcohols are then conveniently transformed to the formula LXXXVIII and LXXXIX products by methods described above. Refer to the transformations of the formula XXXV compound to the formula XXXVI compound in Chart B.

Chart H provides a method whereby the formula XCVII 5-fluoro-$CBA_2$ compounds are prepared from the formula XCIII $CBA_2$ intermediates known in the art. See, for example, British Published Application No. 2,014,143, especially the discussion relative to step (b) of Chart A therein. This formula XCI sulfoximine is transformed to the formula XCII fluorinated sulfoximine by first generating an anion of the formula XCII compound, e.g., by treatment with n-butyllithium in hexane, and treating the resulting anion with a fluorine source. Particularly preferred as a source of fluorine is perchloryl fluoride ($FClO_3$).

The formula XCII compound thusly prepared and the known formula XCIII compound described above are then employed in the preparation of the formula XCIV compound by known methods. Refer again to step (b) of Chart A of British Published Application No. 2,014,143.

The formula XCIV compound thusly prepared is then transformed to the formula XCV primary alcohol by hydrolysis under mild acidic conditions (e.g., mixtures of acetic acid, water, and tetrahydrofuran) as is known in the art. Thereafter, the formula XCV primary alcohol is oxidized to the corresponding formula XCVI carboxylic acid employing conventional means. For example, treatment with oxygen and an aqueous suspension of platinum oxide hydrogenated at ambient temperature and pressure yields the formula LXXVI carboxylic acid. Thereafter, the formula XCVI compound is transformed into the various formula XCVII products by derivatization or transformation of the carboxyl group of the formula XCVI compound.

The C-5 isomers of the formula XCIV to formula XCVII compounds are conveniently separated at any step during the process of Chart H, but are most conveniently and preferably separated from the formula XCIV diastereomeric mixture. Conventional means, e.g., column chromatography, are employed in the separation.

Chart I provides an optional method whereby the known formula CI compound is transformed to the formula CIII products herein. With respect to Chart I, the formula XCII is prepared from the formula XCI compound by the procedure described in Chart H for the preparation of the formula XCVII compound from the formula XCIII compound. This formula CII $CBA_2$ intermediate is then transformed to the formula CIII compound by the procedures described in Chart F for the transformation of the formula LXXI to the formula LXXIII compound.

Chart J provides the preferred methods for preparing the formula X CBA analogs wherein $Z_1$ is trans—$CH_2$—CH=CH—. With respect to Chart J, $R_1$ therein is other than hydrogen or a cation, preferably being lower alkyl. The formula CXIV is prepared from the formula CXI compound by first preparing the α-phenylselenyl derivative thereof, dehydrophenylselenizing, whereby the formula CXIII, α,β-unsaturated ester is prepared. This ester is then transformed to the formula CXIV free acid ($X_1$ is —COOH) by saponification and this free acid is transformed to the various other formula CXIV compounds as indicated in Chart H (refer to the transformation of the formula XCVI compound to the formula XCVII compound).

Chart K provides the preferred method whereby the formula VI CBA intermediates wherein $Z_1$ is trans—$CH_2$—CH=CH— are prepared. With respect to Chart K, the formula CXXI compound is transformed to the formula CXXIII compound by methods analogous to those described in Chart J for the preparation of the formula CXIV compound from the formula CXI compound.

For a detailed description of the methodology employed in Charts J–K, refer to the discussion in British Pat. No. 2,014,143, and references cited therein.

Charts L–O provide methods whereby $CBA_2$ intermediates and analogs are employed in the synthesis of corresponding $CBA_1$ intermediates and analogs.

Chart L provides the preferred method for preparing the formula VII $CBA_1$ intermediates wherein $Z_1$ is trans—$CH_2$—CH=CH—. With respect to Chart L the formula CXXXI compound, prepared as the formula CXXII compound of Chart K, is reduced to the formula CXXXII compound by conventional methods. For a discussion of such methods, and general methodologies for transforming $CBA_2$ intermediates and analogs to corresponding $CBA_1$ intermediates and analogs, refer to British Published Application No. 2,017,699. For example, catalytic hydrogenation with conventional catalysts under atmospheric pressure is employed.

Thereafter, this formula CXXXII compound is successively transformed to the formula CXXXIII α,β-unsaturated ester and the formula CXXXIV $CBA_1$ intermediate by methods described in Charts J–K (i.e., the transformation of the formula CXII compound to the corresponding formula CXIV compounds and the transformation of the formula CXXII compound to the formula CXXIII compound).

Otherwise, the formula VII $CBA_1$ intermediates are prepared according to the method of Chart M, wherein the formula CXLI compound, prepared above, is reduced to the formula CXLII intermediates by techniques described in Chart L and references cited therein.

Chart N describes the preparation of the various $CBA_1$ analogs from the formula CLI compounds prepared in Charts L and M. Procedures employed in Chart N are those described in Chart F above.

Finally, Chart O provides an alternative method for the preparation of the formula CLXII $CBA_1$ analogs directly from formula CLXI $CBA_2$ analogs. This transformation of Chart O proceeds by direct reduction of the formula CLXI compound by methods described in Chart M and references cited therein. Chart O is an especially convenient method for the preparation of $CBA_1$ analogs wherein $Y_1$ is —$CH_2CH_2$—.

The formula XI CBA analogs are prepared according to the methods described in Charts P–U. With respect to Chart P, the formula CLXXI compound is known in the art or prepared by methods known in the art. See U.S. Pat. No. 4,181,789. This compound is conveniently transformed to the corresponding formula CLXXII methylene and formula CLXXIII hydroxymethyl compounds by methods known in the art. Such procedures are particularly and especially described in U.S. Pat. Nos. 4,012,467 and 4,060,534.

The formula CLXXIII compound thusly prepared is thereafter converted to the formula CLXXIV mesylate by methods known in the art, e.g., reaction with methanesulfonyl chloride in a tertiary amine base. Alternatively, other sulfonated derivatives corresponding to the formula CLXXIV compound are prepared such as those described in connection with formula LIII in Chart D.

Thereafter, the formula CLXXIV mesylate (or other sulfonate) is selectively hydrolyzed to yield the formula CLXXV phenol derivatives. Selective hydrolysis of $R_{28}$ silyl ether groups in the presence of protected $R_{18}$ or $M_6$ hydroxyl groups is accomplished by methods hereinabove described, i.e., the use of tetra-n-butyl ammonium floride by methods known in the art and hereinabove described. The formula CLXXV phenol derivative is then cyclized to yield the formula CLXXVI compounds. Cyclization proceeds most conveniently by treatment of the formula XVI compound with base at elevated temperatures. For example, n-butyllithium, sodium hydride, or potassium hydride are conveniently employed at reflux temperatures in organic solvent such as tetrahydrofuran or glyme.

The cyclized formula CLXXVI compound is then transformed to the formula CLXXVII compound by ω-carboxyalkylation. Methods known in the art are employed, e.g., methods for preparing 3,7-inter-phenylene-PGFα compounds and corresponding phenolic intermediates. For example, the preparation of the formula CLXXVII compound proceeds by reaction of the formula CLXXVI compound with sodium hydride and the alkyl bromoalkanoate corresponding to the —$Z_4$—$COOR_1$ group to be introduced into the molecule. Thereafter, the formula CLXXVIII compound is prepared by deprotection, i.e., hydrolysis under mild acidic conditions of the protective groups, followed by transformation to various other C-1 derivatives by methods hereinafter described.

Chart Q provides a method whereby further formula XI CBA analogs in accordance with the present invention are prepared. In particular, formula XI compounds wherein at least one of $R_{20}$, $R_{21}$, $R_{23}$, or $R_{24}$ is not hydrogen are prepared. In accordance with Chart Q, the formula CLXXXI compound, referred to above in the discussion pertaining to Chart P, is oxidized to the corresponding formula CLXXXII aldehyde by methods known in the art. For example, Collins reagent is employed in this oxidation. When conversion of one C-9 stereoisomer of formula CLXXXIII to the other is described, refer to the procedure in Chart R.

Thereafter, the formula CLXXXII aldehyde is hydrolyzed to the corresponding formula CLXXXIII phenol derivative by methods described above for the preparation of the formula CLXXV compound from the formula CLXXIV compound of Chart P.

Thereafter, cyclization of the formula CLXXXIII to the corresponding formula CLXXXIV compound is accomplished by heating at reflux in an organic solvent the phenoxide anion of the formula CLXXXII compound. See for reference Casiraghi, G., et al., J.C.S. Perkin I, 2027 (1979). The C-9 isomers of the formula CLXXXIV compound are conveniently separated by conventional techniques, e.g., column chromatography. Thereafter, the formula CLXXXIV compound is transformed to the formula CLXXXV compound by methods described in Chart P for the preparation of the formula CLXXVII compound from the formula CLXXVI compound. This alcohol is then oxidized to the corresponding formula CLXXXVI ketone (e.g., by methods described above for the preparation of the formula CLXXXII compound from the formula CLXXXI compound) or dehydrated to yield the formula CLXXXVIII compound. Such dehydrations proceed by methods known in the art and include first preparing the mesylate corresponding to the formula CLXXXV compound following by treatment with base.

Thereafter, the formula CLXXXVI or CLXXXVIII compound is transformed, respectively, to the formula CLXXXVII or CLXXIX compound by methods hereinafter described.

Finally, the formula CLXXXIX compound thusly prepared is dehydrogenated to yield the formula CXC compound by conventional means, e.g., catalytic dehydrogenation (palladium-on-carbon catalyst) or treatment with DDQ (2,3-dichloro-5,6-dicyano-1,4-benzoquinone).

Chart R provides a method whereby the C-9 epimeric forms of compounds prepared according to Chart P are prepared. With respect to Chart R, the formula CXCI aldehyde, prepared as the formula CLXXXII compound of Chart Q is isomerized by treatment under basic conditions (i.e., the use of an organic base such as 1,8-diazobicyclo[5.4.0]undec-7-ene in an organic solvent (e.g., methylene chloride). Thereafter this $9\beta$-aldehyde is reduced to the corresponding formula CXCIII alcohol by treatment with a suitable reducing agent, such as a borohydride reducing agent. (e.g., sodium, lithium, or potassium borohydride). Thereafter, the formula CXCIII alcohol thusly prepared is transformed to the corresponding $9\beta$-CBA analogs by methods described in Chart P, e.g., the transformation of the formula CLXXIII to the formula CLXXVIII compound.

Optionally, the various formula XI CBA analogs prepared according to Charts P, Q, and R are prepared by the procedure of Chart S. The procedure of Chart S employs the formula CCI starting material described in chart P which is thereafter converted to the formula CCII compound prepared in accordance with methods described for the preparation of the formula CLXXVIII compound from the formula CLXXI compound of Chart P, the formula CLXXXVII, formula CLXXXIX, formula CXC compounds from the formula CLXXXI compound of Chart Q and the formula CXCIV compounds from the formula CXCI compound of Chart R. The formula CCII compound thusly prepared is then transformed to the formula CCIII compounds by methods hereinabove described, e.g., the transformation of the formula LXXI compound to the formula LXXIII compound of Chart F.

Chart T provides a preferred method whereby the 9-deoxo-2',9-metheno-3-oxo-4,5,6-trinor-3,7-(1,3-interphenylene)-$PGE_1$ compounds of formula CCXIII are prepared. In accordance with Chart T the formula CCXI compound, prepared as the formula CLXXXIII compound of Chart Q, is treated with a methyl Grignard reagent, methyl magnesium bromide and heated at reflux in an organic solvent (e.g., glyme).

The formula CCXII thusly prepared is then transformed to the formula CCXIII product by the method described in Chart P for the preparation of the formula CLXXVIII product from the formula CLXXVI phenol intermediate.

Chart U provides a convenient method whereby formula XI compounds wherein $Y_1$ is trans—CH=CH—, the formula CCXXI compound of Chart U, are transformed to corresponding formula CCXXII aldehyde intermediates. This transformation is accomplished by ozonolysis by methods otherwise known in the art.

The formula CCXXII intermediate is then conveniently transformed to various formula XI products (the Formula CCXXIII compound of Chart U) by methods described above, i.e., reduction of the formula CCXXII compound with the appropriate Wittig reagent followed by reduction and hydrolysis. Accordingly by the procedure described in Chart U the C-12 side chains of the various formula CCXXI compounds is conveniently modified by the formula CCXXII aldehyde intermediates. As discussed above, the processes herein described lead variously to carboxylic acids ($X_1$ is —$COOR_1$ and $R_1$ is hydrogen) or to esters or primary alcohols ($X_1$ is —$CH_2OH$).

When the alkyl ester has been obtained and an acid is desired, saponification procedures, as known in the art for PGF-type compounds are employed.

When an acid has been prepared and an alkyl, cycloalkyl, or aralkyl ester is desired, esterification is advantageously accomplished by interaction of the acid with appropriate diazohydrocarbon. For example, when diazomethane is used, the methyl ester is produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about 10 min, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for alkyl, cycloalkyl or aralkyl esterification of the carboxy moiety of the acid compounds comprises transformation of the free acid to the corresponding substituted ammonium salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like.

Various methods are available for preparing phenyl or substituted phenyl esters within the scope of the invention from corresponding aromatic alcohols and the free acid, differing as to yield and purity of product.

With regard to the preparation of the phenyl, particularly p-substituted phenyl esters disclosed herein (i.e., $X_1$ is —$COOR_1$ and $R_1$ is p-substituted phenyl), such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This anhydride is then reacted with a solution of the phenol corresponding to the p-substituted phenyl ester to be prepared. This reaction proceeds preferably in the presence of a tertiary amine, such as pyridine. When the conversion is complete, the p-substituted phenyl ester has been recovered by conventional techniques.

A preferred method for substituted phenyl esters is that disclosed in U.S. Pat. No. 3,890,372 in which a mixed anhydride is reacted with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See, for example, U.S. Pat. No. 3,984,454, German Offenlegungsschrift No. 2,535,693, and Derwent Farmdoc No. 16828X.

Carboxyamides ($X_1$ is —$COL_4$) are prepared by one of several amidation methods known in the prior art. See, for example, U.S. Pat. No. 3,981,868, issued Sept. 21, 1976 for a description of the preparation of the present amido and cycloamido derivatives of prostaglandin-type free acids and U.S. Pat. No. 3,954,741 describing the preparation of carbonylamido and sulfonylamido derivatives of prostaglandin-type free acids.

The preferred method by which the present amido and cycloamido derivatives of the acids are prepared is, first, by transformation of such free acids to corresponding mixed acid anhydrides. By this procedure, the prostaglandin-type free acid is first neutralized with an equivalent of an amine base, and thereafter reacted with a slight stoichiometric excess of a chloroformate corresponding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the free acid is mixed with both the tertiary amine base and the chloroformate in a suitable solvent (e.g., aqueous tetrahydrofuran), allowing the reaction to proceed at $-10°$ C. to $20°$ C.

Thereafter, the mixed anhydride is converted to the corresponding amido or cycloamido derivatives by reaction with the amine corresponding to the amide to be prepared. In the case where the simple amide (—$NH_2$) is to be prepared, the transformation proceeds by the addition of ammonia. Accordingly, the corresponding amine (or ammonia) is mixed with the mixed anhydride at or about $-10°$ to $+10°$ C., until the reaction is shown to be complete.

Thereafter, the novel amido or cycloamido derivative is recovered from the reaction mixture by conventional techniques.

The carbonylamido and sulfonylamido derivative of the presently disclosed PG-type compounds are likewise prepared by known methods. See, for example, U.S. Pat. No. 3,954,741 for description of the methods by which such derivatives are prepared. By this known method the acid is reacted with a carboxyacyl or sulfonyl isocyanate, corresponding to the carbonylamido or sulfonylamido derivative to be prepared.

By another, more preferred method the sulfonylamido derivatives of the present compounds are prepared by first generating the PG-type mixed anhydride, employing the method described above for the preparation of the amido and cycloamido derivatives. Thereafter, the sodium salt of the corresponding sulfonamide is reacted with the mixed anhydride and hexamethylphosphoramide. The pure PG-type sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method methanolic sodium methoxide is reacted with an equal molar amount of the sulfonamide. The sulfonamide salt is then reacted, as described above, with the mixed anhydride, using about four equivalents of the sodium salt per equivalent of anhydride. Reaction temperatures at or about 0° C. are employed.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. in the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

DESCRIPTION OF THE PREFERRED EMBODIMENTS

The present invention is more completely understood by the operation of the following examples:

EXAMPLE 1

3-oxo-7α-tetrahydropyran-2-yloxy-6β[(3'S)-3'-tetrahydropyran-2-yloxy-trans-1'-octenyl]-bicyclo[3.3.0]-oct-1-ene (Formula XXIV: $R_{18}$ is tetrahydropyranyloxy; $Y_1$ is trans—CH=CH—, $M_6$ is α-tetrahydropyranyloxy:β-H, $L_1$ is α-H:β-H, $R_{27}$ is n-butyl; and n is the integer one)

Refer to Chart A.

A. To a stirred solution of 19 ml (170 mmoles) dimethyl methylphosphonate and 600 ml of dry tetrahydrofuran at −78° C. under an argon atmosphere is added dropwise over 5 min 110 ml (172 mmoles) of 1.56 M n-butyllithium in hexane. The resulting solution is stirred for 30 min at −78° C., treated with 25.4 g of 3α,5α-dihydroxy-2β-(3α-hydroxytrans-1-octenyl)-1α-cyclopentaneacetic acid, lactone, bis(tetrahydropyranyl)ether, in 100 ml of dry tetrahydrofuran dropwise over one hr, and stirred for one hr at −78° C. and four hr at room temperature. The reaction is then quenched by addition of 10 ml glacial acetic acid, diluted with 700 ml of brine, and extracted with diethyl ether (3×700 ml). The combined ethereal layers are washed with 200 ml bicarb and 500 ml brine and dried over anhydrous sodium sulfate and concentrated under reduced pressure to yield 37 g of formula XXII compound as oily white solid: 3-dimethylphosphonomethyl-3-hydroxy-2-oxa-7α-tetrahydropyran-2-yloxy-6β[(3'S)-3'-tetrahydropyran-2-yloxy-trans-1'-octenyl]-bicyclo[3.3.0]octane. Crystallization of the crude product from hexane and ether yields 22.1 g of purified formula XXII product. Silica gel TLC $R_f$ is 0.22 in ethyl acetate. The melting range is 89°–93° C. NMR absorptions are observed at 3.72 (doublet, J=11 Hz) and 3.83 (doublet, J=11 Hz)δ. Characteristic infrared absorptions are 3340, 1250, 1185, 1130, 1075, and 1030 cm$^{-1}$.

B. To a solution of 10.0 g of the product of Part A in 75 ml acetone stirring under a nitrogen atmosphere at −10° C. is added over 30 min 9.0 ml of Jones reagent. The resulting suspension is stirred for 30 min at −10° C. and then quenched with 4 ml 2-propanol. The solvents are decanted away from the green residue and most of the acetone removed at reduced pressure. The acetone concentrate is then taken up in ethyl acetate and washed with saturated aqueous sodium bicarbonate and then with brine and dried over anhydrous sodium sulfate. Concentration under reduced pressure yields 8.2 g of formula XXIII product: 2-decarboxy-6-desbutyl-6-dimethylphosphonomethyl-6-keto-PGE$_1$, 11,15-bis(tetrahydropyranyl ether). Chromatography of formula XXIII product on 600 g silica gel eluting with 20% acetone in methylene chloride yields 4.95 g of pure formula XXIII product. Silica gel TLC $R_f$ (in 20% acetone in methylene chloride) is 0.22. Characteristic NMR absorptions are observed at 3.14 (doublet, J=23 Hz) and 3.80 (doublet, J=11 Hz), 5.4–5.8 (m)δ. Characteristic infrared absorptions are observed at 1745, 1715, 1260, 1200, 1185, 1130, 1030, 970, 870 cm$^{-1}$.

C. A suspension of 5.37 g of the product of Example 1, Part B, 1.33 g anhydrous potassium carbonate, and 5.37 g 18-Crown-6 ether in 200 ml toluene is heated at 75° C. for six hr under a nitrogen atmosphere, cooled to 0° C., and washed with 200 ml brine, 200 ml of 3:1 water:brine, and 200 ml brine, and dried over anhydrous sodium sulfate. Most of the solvents are removed under reduced pressure and the residue is filtered through 50 g silica gel eluting with 250 ml ethyl acetate to give 3.9 g of formula XXIV product: 3-oxo-7α-tetrahydropyranyl-2-yloxy-6β[(3'S)-3'-tetrahydropyran-2-yl-trans-1'-octenyl]bicyclo[3.3.0]oct-1-ene. The crude product is chromatographed on 300 g silica gel eluting with 60:40 hexane:ethyl acetate to give 2.39 g of pure title product. Silica gel TLC $R_f$ is 0.22 in 60:40 hexane:ethyl acetate. NMR absorptions are observed at 5.18–5.86 (m) and 5.94 (broad singlet)δ. Infrared absorptions are observed at 1710 and 1632 cm$^{-1}$.

Following the procedure of Example 1, but employing the various 3α,5α-hydroxy-2-substituted-1α-cyclopentaneacetic acid δ-lactones of formula XXI, there are prepared each of the various corresponding formula XXIV products wherein n is one.

Further, following the procedure of Example 1, but employing each of the various 3α,5α-dihydroxy-2-substituted-1α-cyclopentanepriopionic acid, δ-lactones of formula XXI, there are prepared each of the various formula XXIV compounds wherein n is 2.

Further, following the procedure of Example 1, but employing each of the various 5α-hydroxy-2-substituted-1α-cyclopentanealkanoic acid lactones of formula XXI, there are prepared each of the various formula XXIV compounds wherein $R_{18}$ is hydrogen. Finally, following the procedure of Example 1, but employing each of the various 3α-hydroxymethyl-5α-hydroxy-2-substituted-1α-cyclopentanealkanoic acid lactones of formula XXI, there are prepared each of the various formula XXIV compounds wherein $R_{18}$ is —CH$_2$OR$_{10}$.

EXAMPLE 2

3-oxo-8α-tetrahydropyran-2-yloxy-7β[(3'S)-3'-tetrahydropyran-2-yloxy-trans-1'-octenyl]bicyclo[4.3.0]non-1-ene (Formula XXIV: $R_{18}$, $Y_1$, $M_6$, $R_7$ are defined in Example 1 and n is the integer 2)

Refer to Chart A.

A. A solution of 2.05 ml (18.9 mmoles) of dimethyl methylphosphonate and 100 ml of dry tetrahydrofuran is stirred at −78° C. under a nitrogen atmosphere and treated dropwise with 11.8 ml (18.9 mmoles) of 1.6 molar n-butyllithium in hexane. After stirring for 30 min at −78° C., the resulting mixture is treated dropwise over 25 min with 4.25 g of 3α,5α-dihydroxy-2β-(3α-hydroxy-trans-1-octenyl) 1α-cyclopentane propionic acid, δ-lactone, 11,15-bis(tetrahydropyranyl ether), in 30 ml of dry tetrahydrofuran. The resulting mixture is then stirred for one hr at 78° C. The solution is then allowed to stir at ambient temperature for 2 hr and is quenched by addition of 1.2 ml of acetic acid. The mixture is then added to 250 ml of brine and 200 ml of diethyl ether. The aqueous and organic layers are then separated and the aqueous layer extracted twice with diethyl ether. The ethereal extracts are then washed with brine, dried over anhydrous sodium sulfate, and concentrated to yield 5.6 g of crude formula XXII compound, as an oil: 3-(dimethylphosphonomethyl)-3-hydroxy-2-oxa-8α-tetra-hydropyran-2-yl-oxy-7β[(3'S)-3'-tetrahydropyran-2-yloxy-trans1'-octenyl]-bicyclo[4.3.0]nonane. Chromatography on silica gel eluting with 4:1 ethyl acetate:acetone yields 4.1 g of purified formula XXII product. Characteristic NMR absorption is observed at 5.15-5.65 (multiplet)$\delta$. Silica gel TLC $R_f$ is 0.34 in 4:1 ethyl acetate:acetone. Characteristic infrared absorptions are observed at 3350, 1235, and 1030 cm$^{-1}$.

B. A suspension of 3.42 g of chromium trioxide and 80 ml of methylene chloride is treated with 5.8 ml of pyridine, stirred at ambient temperature under a nitrogen atmosphere for 30 min, and combined with 3 scoops of dry diatomaceous earth. The resulting mixture is then treated with 3.25 g of the reaction product of Part A and 8 ml of dry dichloromethane, stirred for 30 min at ambient temperature under nitrogen, filtered through 30 g of silica gel (eluting with 200 ml of ethylacetate and acetone, 2:1) and concentrated under reduced pressure. Chromatographing the residue (3.73 g) on 120 g of silica gel, eluting with ethyl acetate and acetone (4:1) yields 2.07 g of formula XXIII product: 2-decarboxy-5-despropyl-6-dimethylphosphonomethyl-5-keto-PGE$_1$, 11,15-bis(tetrahydropyranyl ether). Characteristic infrared absorptions are observed at 1740 and 1715 cm$^{-1}$.

Characteristic NMR absorptions are observed at 3.1 (doublet, J=23 Hz) and 3.8 (doublet, J=11 Hz)$\delta$.

C. A suspension of 12 mg of 50% sodium hydride in mineral oil and 3 ml of diglyme is stirred at 0° C. under an argon atmosphere. The suspension is then treated with 150 mg of the product of Part B in 3 ml of diglyme. After 1 hr, the cooled bath is removed and the resulting solution is stirred at ambient temperature under argon. After a total of 20 hr from addition of the formula XXIII reactant, the resulting solution is then added to 30 ml of water and extracted with 90 ml of diethyl ether. The ethereal extract is washed with brine (30 ml), dried over anhydrous sodium sulfate, concentrated under reduced pressure to a brown oil (110 mg) and chromatographed on 10 g of silica gel eluting with hexane and ethyl acetate (1:1). There is accordingly prepared 15 mg of formula XXIV compound: 3-oxo-8$\alpha$-tetrahydropyran-2-yloxy-7$\beta$-[(3'S)-3'-tetrahydropyran-2-yloxy-trans-1'-octenyl]bicyclo[4.3.0]non-1-ene. NMR absorptions are observed at 4.7 (broad singlet) and 5.3-6.0 (multiplet)$\delta$. IR absorption is observed at 1670 cm$^{-1}$.

Alternatively, the formula XXIV compound above is prepared as follows:

A solution of 150 mg of the product of Part B and 5 ml of dry tetrahydrofuran at 0° C. under an argon atmosphere is treated dropwise with 0.5 ml of 0.52 M potassium hydride and 18-crown-6 ether (Aldrich Chemical Co. Catalog Handbook of Fine Chemicals 1979-1980, Milwaukee, Wis., p. 133; Pedersen, J. C., JACS 92:386 (1970)) in tetrahydrofuran (prepared from 800 mg potassium hydride and 1.0 g 18-crown-6 ether in 8.7 ml of dry tetrahydrofuran). After stirring for one hr at 0° C. under argon, the mixture is added to 30 ml of water, extracted with 90 mg of diethyl ether and the ethereal extract is washed with brine, dried over anhydrous sodium sulfate, concentrated under reduced pressure, and chromatographed on 9 g of silica gel eluting with ethyl acetate and hexane. Formula XXIV product (40 mg) is thereby obtained. Silica gel TLC $R_f$ is 0.30 in ethyl acetate and hexane (1:1).

EXAMPLE 3

1$\beta$-Methyl-3-oxo-7$\alpha$-tetrahydropyran-2-yl-oxy-6$\beta$-[(3'S)-3'-tetrahydropyran-2-yloxy-trans-1'-octenyl]-bicyclo-[3.3.0]octane (Formula XXV: R$_{18}$, Y$_1$, M$_6$, n, L$_1$, R$_7$ are as defined in Example 1, R$_{16}$ is hydrogen and R$_{37}$ is methyl)

Refer to Chart A.

A suspension of 2.70 g of anhydrous copper iodide is stirred in 100 ml of anhydrous diethyl ether at $-20°$ C. under an argon atmosphere and is treated dropwise with 20.0 ml of 1.4 M ethereal methyllithium. The resulting solution is then stirred for 15 min at $-20°$ C. and treated over 2.5 hr at $-20°$ C. with a solution of 2.00 g of the title product of Example 1 in 100 ml of anhydrous diethyl ether. Stirring is continued for an additional 1.5 hr at $-20°$ C. and the resulting mixture added to 200 ml of 1 M aqueous ammonium chloride. The aqueous and organic layers are then separated and the aqueous layer extracted with diethylether (400 ml). The combined organic extracts are then washed with 200 ml of brine, dried over anhydrous sodium sulfate, concentrated under reduced pressure to yield 2.4 g of the title product as a pale green oil. Chromatography on 25 g of silica gel eluting with hexane in ethyl acetate (3:1) yields 2.0 g of title product as a colorless oil. Characteristic NMR absorptions (CDCl$_3$) are observed at 1.18, 3.20-4.43, 4.70, and 5.2-5.9$\delta$. Characteristic infrared absorptions are observed at 1745, 1665, 1200, 1130, 1110, 1075, 1035, 1020, 980, and 870 cm$^{-1}$. Silica gel R$_f$ is 0.26 in ethyl acetate and hexane (1:3).

By procedures known in the art, each of the various novel formula XXV intermediates is transformed to a 9$\beta$-methyl-CBA$_2$ or CBA$_1$ compound by methods exemplified hereinafter or known from British Published Specifications Nos. 2,013,661, 2,014,143, and 2,017,699.

EXAMPLE 4

5-Carboxypentanol, t-butyldimethylsilyl ether

A solution of 4 g of sodium hydroxide in 100 ml of methanol and water (4:1) is treated with 10 ml of caprolactone and stirred at ambient temperature under a nitrogen atmosphere. After 20 hr, solvent is evaporated following addition of toluene, yielding 15 g of solid, crude 5-carboxypentanol.

The above solid is suspended in 300 ml of dimethylformamide under a nitrogen atmosphere, cooled to 0° C., treated with 35 g of imidazole, stirred for 15 min at 0° C. and 15 min at ambient temperature, cooled to 0° C. and treated with 39 g of t-butyldimethyl silylchloride. The resulting solution is then allowed to warm to ambient temperature under a nitrogen atmosphere. After 26 hr, the resulting solution is treated with 8 g of sodium hydroxide in 40 ml of water and 40 ml of methanol, with stirring maintained under a nitrogen atmosphere. After 13 hr, the suspension is acidified to pH 4 with 500 ml of 1 N aqueous hydrogen chloride, then saturated with sodium chloride and extracted with ethyl acetate. The ethyl acetate extracts are then washed with 1 N aqueous sodium hydroxide. The basic extracts are then acidified to pH 4 with concentrated hydrochloric acid, saturated with brine, and extracted with ethyl acetate. The ethyl acetate extracts are then washed with brine, dried over sodium sulfate, and concentrated under reduced pressure to yield 22.6 g of a yellow liquid, 5-carboxypentanol, t-butyldimethylsilyl ether. Chromatography on 800 g of silica gel eluting with ethyl acetate and hexane (1:9 to 1:1) yields 14.8 g of 5-carboxypentanol, t-butyldimethylsilyl ether. NMR absorptions are observed at 0.05 (singlet) and 0.90 (singlet)δ. Infrared absorptions are observed at 3000 (broad) and 1700 cm$^{-1}$.

Following the procedure of Example 4, but employing each of the various lactones corresponding to the ω-carboxyalkanol compounds of formula XXXII there are prepared each of the various formula XXXII products.

EXAMPLE 5

2-Decarboxy-2-(t-butyldimethylsilyloxy)methyl-5-carboxy-6-hydroxy-9β-methyl-CBA$_1$, 11,15-bis(tetrahydropyran)ether (Formula XXXIII: $R_{28}$ is t-butyldimethylsilyl, $Z_2$ is —$(CH_2)_3$—, n is 1, and $R_{16}$, $R_{18}$, $R_{37}$, $M_6$, $L_1$, and $R_4$ are as defined in Example 3)

Refer to Chart B.

A solution of 0.58 ml of dry diisopropylamine and 20 ml of dry tetrahydrofuran at 0° C. under an argon atmosphere is treated with 2.6 ml of 1.56 M n-butyllithium in hexane, stirred for 5 to 10 min at 0° C., treated with 0.50 g of the title product of Example 4 in 5 ml of tetrahydrofuran, stirred for 15 min at 0° C. and 1 hr at ambient temperature, cooled to 0° C., treated with 0.91 g of the title product of Example 3 in 5 ml of tetrahydrofuran, and allowed to slowly warm to ambient temperature under an argon atmosphere. Thereafter, 130 ml of water and 20 ml of brine are added and the mixture extracted with diethyl ether. The ethereal extracts are then washed with 4 ml of 1 N aqueous hydrochloric acid and 150 ml of brine and dried over sodium sulfate, and concentrated under reduced pressure to yield title product.

Following the procedure of Example 5, but employing each of the various formula XXXI compounds described following Example 1, there are prepared each of the various formula XXXIII compounds wherein $R_{28}$ is t-butyldimethylsilyl and $Z_2$ is —$(CH_2)_3$—.

EXAMPLE 6

2-Decarboxy-2-(t-butyldimethylsilyloxy)methyl-]β-methyl-CBA$_2$, 11,15-bis-(tetrahydropyranylether) (Formula XXXIV: $R_{28}$, $Z_2$, $R_{18}$, $Y_1$, $M_6$, $L_1$ and $R_7$ are as defined for Examples 1 and 5)

The reaction product of Example 5 (1.37 g) and 16 ml of methylene chloride is treated with 2.9 ml of dimethylformamide dineopentyl acetal, stirred for 3 hr at ambient temperature under nitrogen, added to 160 ml of ice water and 40 ml of brine, and extracted with diethyl ether. The ethereal extracts are then washed with 150 ml of sodium bicarbonate and 150 ml of brine, dried over sodium sulfate, and concentrated under reduced pressure to yield crude title product. Chromatography on 100 g of silica gel eluting with 10% ethyl acetate in hexane yields pure title product.

Following the procedure of Example 6, but employing each of the various formula XXXIII compounds described following Example 5, there are prepared each of the various corresponding formula XXXIV products wherein $R_{28}$ is t-butyldimethylsilyl and $Z_2$ is —$(CH_2)_3$—.

EXAMPLE 7

2-Decarboxy-2-hydroxymethyl-9β-methyl-CBA$_2$, 11,15-bis(tetrahydropyranyl)ether (Formula XXXV: $Z_2$, n, $R_{16}$, $R_{37}$, $R_{18}$, $Y_1$, $M_6$, $L_1$, and $R_7$ are as defined in Examples 1 and 5)

Refer to Chart B.

A solution of 0.71 g of the title product of Example 6 and 16 ml of dry tetrahydrofuran at 0° C. under a nitrogen atmosphere is treated with 3.2 ml of 0.75 molar tetra-n-butylammoniumfluoride and tetrahydrofuran. After allowing the reaction mixture to slowly warm to ambient temperature overnight with stirring, 150 ml of brine is added and the resulting mixture extracted with ethyl acetate. The ethyl acetate extracts are then washed with 0.5 N aqueous potassium bisulfate, 100 ml of sodium bicarbonate, and 100 ml of brine, dried over sodium sulfate, and concentrated under reduced pressure to yield crude title product. Filtering through 25 g of silica gel with 200 ml of ethyl acetate and hexane yields 0.61 g of further purified product. Chromatography on silica gel eluting with 35% ethyl acetate in hexane yields pure title product.

Following the procedure of Example 7, but employing each of the various formula XXXIV compounds described in and following Example 6, there are prepared each of the various Formula XXXV compounds wherein $Z_2$ is —$(CH_2)_3$—.

Following the procedure of Examples 5, 6, and 7, and employing the various starting materials described in and following these examples and each of the various formula XXXII compounds described in and following Example 4, there are prepared each of the various formula XXXV compounds.

EXAMPLE 8

2-Decarboxy-2-hydroxymethyl-9β-methyl-CBA$_2$ (Formula XXXVI: $X_1$ is —$CH_2OH$, $Z_2$ is —$(CH_2)_3$—, $R_8$ is hydroxy, $Y_1$ is trans—CH=CH—, $M_1$ is α-OH:β-H, $L_1$ is α-H:β-H and $R_7$ is n-butyl)

Refer to Chart B.

The title product of Example 7 (0.25 g) is combined with 9 ml of acetic acid, water and tetrahydrofuran (6:3:1) and heated to 37°–40° C. for two hr. Thereafter the resulting mixture is cooled and extracted with diethyl ether. The ethereal extracts are then washed with brine, dried over sodium sulfate and concentrated to yield crude title product. Chromatography on silica gel yields pure title product.

Following the procedure of Example 7, but employing each of the various formula XXXV primary alcohols described in and following Example 7 there are prepared of the various corresponding formula XXXVI products wherein $X_1$ is —$CH_2OH$.

EXAMPLE 9 o-(t-Butyldimethylsilyloxyethyl)benzaldehyde (Formula XLIV: $R_{28}$ is t-butyldimethylsilyloxy and g is one)

Refer to Chart C.

A. To a mixture of 7.6 g of lithium aluminum hydride and 400 ml of dry tetrahydrofuran under a nitrogen atmosphere is added dropwise with stirring 18 g of homophthalic acid (Aldrich Chemical Company) in 250 ml of dry tetrahydrofuran. Dropwise addition rate is adjusted such that mild reflux is maintained during the course of the exothermic reaction. The resulting mixture is then heated at reflux for 5 hr, cooled to 0° C., and 7.6 g of water in 50 ml of tetrahydrofuran is added dropwise with stirring. Thereafter 27 ml of 10% aqueous sodium hydroxide is added and the resulting mixture is stirred at ambient temperature for 20 min, filtered, and the filter solids washed with 150 ml of tetrahydrofuran. The filtrate and tetrahydrofuran wash are then concentrated under reduced pressure to yield 14.0 g of crude formula XXXII diol, 2-(o-hydroxymethyl-phenyl)ethanol. Chromatography on 1.2 kg of silica gel, deactivated by addition of 240 ml of ethyl acetate, eluting with ethyl acetate, yields 13.5 g of formula XLII product. Melting range is 41.5°–43° C.

B. To a solution of 13.5 g of the reaction product of Part A in 50 ml of dry tetrahydrofuran under a nitrogen atmosphere is added with stirring 9.05 g of imidazole. The resulting solution is then cooled to −5° C. and 13.9 g of t-butyldimethylsilyl chloride is added. The resulting mixture is then maintained for 20 min and thereafter allowed to warm to ambient temperature. After 1 hr, the resulting mixture is then shaken with 500 ml of hexane and diethylether (2:1) and 250 ml of water and brine (1:1). The organic layer is then washed with water and brine, dried over magnesium sulfate, and concentrated under reduced pressure to yield a crude mixture of mono- and bis-silyl ethers corresponding to the starting material of Part A. This mixture of products is then chromatographed on 2 kg of silica gel, deactivated with 400 ml of ethyl acetate and eluted with 25% ethyl acetate and Skellysolve B to yield 6.82 g of formula XLIII product, o-(t-butyldimethylsilyloxyethyl)phenylmethanol. NMR absorptions are observed at 7.20–7.52, 4.57, 3.91 (t, J G.1), 2.93 (t, J 6.1), 0.82, and −0.08$\delta$. Silica gel TLC $R_f$ is 0.54 in 25% ethyl acetate and hexane.

C. A mixture of 5.0 g of the reaction product of Part B, 100 ml of trichloromethane, and 25 g of activated manganese dioxide ($MnO_2$) is stirred at ambient temperature for 4 hr. Chloroform (100 ml) is then added and the resulting mixture filtered through diatomaceous earth. After washing filter solids with 200 ml of trichloromethane, the resulting filtrate and wash is then concentrated under reduced pressure to yield a residue containing title product. Chromatography on 400 g of silica gel, deactivated with 80 ml of ethyl acetate and elution with 25% ethyl acetate and hexane yields 2.93 g of pure title product. Silica gel TLC $R_f$ is 0.74 in 25% ethyl acetate and hexane. NMR absorptions are observed at 10.34, 7.25–8.00, 3.89 (t, J 6.0), 3.27 (t, J 6.0), 0.83 and −0.09$\delta$. The mass spectrum exhibits a peak at 265 (M+1) and other peaks of decreasing intensity at m/e 75, 207, 73, 133, 223, 208, 77, 177, 76 and 105.

Following the procedure described in Chart C, but employing each of the various formula XLI acids, there is prepared each of the various corresponding formula XLIV aldehydes wherein $R_{28}$ is t-butyldimethylsilyl.

EXAMPLE 10 m-(t-butyldimethylsilyloxymethyl)benzaldehyde (Formula XLIV: g is zero and $R_{28}$ is t-butyldimethylsilyl)

Refer to Chart C.

A. To a solution of 10.0 g of m-(hydroxymethyl)-phenylmethanol in 40 ml of dry tetrahydrofuran under a nitrogen atmosphere is added with stirring 7.35 g imidazole. The resulting solution is then cooled to 0° C. and 11.3 g of t-butyldimethylsilyl is added. The resulting mixture is then stirred with cooling for 15 min and thereafter allowed to warm to ambient temperature. After 90 min, the resulting mixture is then shaken in 400 ml of hexane and diethyl ether (2:1) and 200 ml of water and brine (1:1). The organic layer is then washed successively with water and brine (1:1, 300 ml) and brine (150 ml), dried over magnesium sulfate and concentrated under reduced pressure to yield a mixture of mono- and bis-t-butyldimethylsilyloxy ether corresponding to the formula XXXII compound. This mixture of products is then chromatographed on 1.4 kg of silica gel, deactivated by addition of 280 ml of ethyl acetate and eluted with 25–40% ethyl acetate in hexane to yield 7.65 g of pure formula XLIII product, m-(t-butyldimethylsilyloxymethyl)phenylmethanol. Silica gel TLC $R_f$ is 0.46 in 25% ethyl acetate and hexane. NMR absorptions are observed at 7.25, 4.72, 4.60, 2.23, 0.92, and 0.09$\delta$. The mass spectrum exhibits a peak at 251 (M+-1) and other peaks of decreasing intensity at m/e 235, 121, 195, 237, 105, 133, 75, 89, 236, and 119.

B. A mixture of 5.0 g of the reaction product of Part A and 100 ml of trichloromethane and 25 g of activated manganese dioxide ($MnO_2$) is stirred at ambient temperature for 4 hr. Chloroform (100 ml) is then added and the resulting mixture filtered through diatomaceous earth. The filter solids are washed with 200 ml of trichloromethane and the filtrate and trichloromethane wash are then concentrated under reduced pressure to yield 5.2 g of crude title product. Chromatography on 400 g of silica gel, deactivated with 80 ml of ethyl acetate and elution with ethyl acetate and hexane (1:3) yields 3.65 g of pure title product. Silica gel TLC $R_f$ is 0.46 in 10% ethyl acetate and hexane. NMR absorptions are observed at 10.00, 7.26–7.86, 4.81, 0.95, and 0.11$\delta$.

EXAMPLE 11

3-Phenylsulfonyl-7α-tetrahydrofuran-2-yloxy-6β-[(3'S)-3'-tetrahydropyran-2-yloxy-trans-1'-octenyl]-bicyclo[3.3.0]octane (Formula LV: n is the integer one, $R_{18}$ is tetrahydropyranyloxy, $Y_1$ is trans—CH=CH—, $M_6$ is α-tetrahydropyranyloxy:β-hydrogen, $L_1$ is α-hydrogen:β-hydrogen, $R_{16}$ and $R_{17}$ are both hydrogen, and $R_{27}$ is n-butyl)

Refer to Chart D.

A. Sodium borohydride (0.38 g) is added with stirring to a solution of 2.90 g of 3-oxo-7α-tetrahydrofuran-2-yloxy-6β-[(3'S)-3'-tetrahydropyran-2-yloxy-trans-1'-octenyl]-bicyclo[3.3.0]octane in 25 ml of 95% aqueous ethanol. The resulting mixture is then stirred at ambient temperature for 20 min. Thereafter the resulting mixture is shaken in 100 ml of brine and 200 ml of ethyl acetate. The organic layer is then immediately washed in brine, dried over magnesium sulfate, and concentrated under reduced pressure to yield 2.94 g of formula LII alcohol: (3RS)-3-hydroxy-7α-tetrahydropyran-2-yloxy-6β-[(3'S)-3'-tetrahydropyran-2-yloxy-trans-1'-octenyl]bicyclo[3.3.0]octane. Infrared absorptions are observed at 3600 and 3450 cm$^{-1}$ and no carbonyl absorption. Silica gel TLC $R_f$ is 0.63 and 0.67 in ethyl acetate and hexane (1:1).

B. To a solution of 2.9 g of the reaction product of Part A in 25 ml of dry dichloromethane and 1.4 ml (1.02 g) of triethylamine at 0° C. is added with stirring 0.57 ml (0.848 g) of methanesulfonyl chloride over 5 min. The resulting mixture is then stirred an additional 20 min and shaken with 160 ml of diethyl ether and 80 ml of cold (0° C.) dilute aqueous hydrochloric acid. The organic layer is then washed successively in brine, dilute aqueous potassium bicarbonate, and brine, dried over sodium sulfate, and concentrated under reduced pressure to yield 3.5 g of crude formula LIII compound: (3RS)-3-hydroxy-7α-tetrahydropyran-2-yloxy-6β-[(3′S)-3′-tetrahydropyran-2-yloxy-trans-1′-octenyl]bicyclo[3.3.0]octane, 3-methylsulfonate.

C. Thiophenol (1.13 ml, 1.21 g) is added to a mixture of 1.12 g of potassium t-butoxide in 15 ml of dry dimethylsulfoxide (DMSO) under a nitrogen atmosphere. To the solution of potassium thiophenoxide thus prepared is added 3.5 g of the reaction product of Part B in 8 ml of dimethylsulfoxide. The resulting mixture is then stirred at ambient temperature for 16 hr, whereupon additional potassium t-butoxide is added so as to transform the solution to a distinct yellow color. The resulting mixture is then stirred an additional 4 hr at ambient temperature, diluted with 100 ml of diethyl ether and 100 ml of hexane, washed with 5% aqueous potassium hydroxide (200 ml) and brine (200 ml), dried over magnesium sulfate, and concentrated under reduced pressure to yield 5 g of a residue of crude formula LIV compound: 3-phenylthio-7-α-tetrahydropyran-2-yloxy-6β-[(3′S)-3′-tetrahydropyran-2-yloxy-trans-1′-octenyl]-bicyclo[3.3.0]octane. Chromatography on 300 g of silica gel, deactivated with 40 ml of diethyl ether and 40 ml of trichloromethane and eluted with 5% diethyl ether in trichloromethane yields 3.1 g of pure product. Silica gel TLC $R_f$ is 0.75 in 10% ethyl acetate in dichloromethane.

D. To a solution of 3.1 g of the reaction product of Part C and 50 ml of dichloromethane at 0° C. is added with stirring over 10 min 2.43 g of 85% m-chloroperbenzoic acid. The resulting mixture is then stirred at 0° C. for 30 min, diluted with 150 ml of dry ethyl ether, washed with ice cold dilute aqueous potassium hydroxide and brine, dried over magnesium sulfate, and concentrated under reduced pressure to yield 3.4 g of crude title product. Chromatography on 350 g of silica gel, deactivated with 70 ml of ethyl acetate and elution with 500 ml of 30-50% ethyl acetate in hexane yields 2.90 g of pure title product as a mixture of C-6 isomers. Silica gel TLC $R_f$'s are 0.41, 0.45 and 0.48 in 30% acetate in hexane (stereoisomers). NMR absorptions are observed at 7.52–8.02, 5.30–5.67, 4.70, and 3.30–4.13δ.

Following the procedure of Example 11, each of the formula LI compounds is transformed to the corresponding formula LV 3-phenylsulfonyl compound.

EXAMPLE 12

(5E)-2,5-inter-o-phenylene-3,4-dinor-CBA$_2$ (Formula LX: $X_1$ is —COOH, g is one, n is one, $R_{16}$ and $R_{17}$ are hydrogen, $R_8$ is hydroxy, $Y_1$ is trans—CH=CH—, $M_1$ is α-OH:β-H, $L_1$ is α-H:b-H, and $R_7$ is n-butyl), its methyl ester and the corresponding (5Z) isomers thereof.

Refer to Chart C.

A. To a solution of 1.26 g of the title product of Example 11 in 15 ml of dry tetrahydrofuran at −78° C. under a nitrogen atmosphere is added dropwise with stirring 1.48 ml of 1.6 M n-butyllithium in hexane over 1 min. After 10 min 0.66 g of title product of Example 9 in 5 ml of dry tetrahydrofuran is added. After 45 min 0.26 ml of distilled acetic anhydride is added. Stirring is then continued at −78° C. for 3 hr and at ambient temperature for an additional 2 hr. The resulting mixture is then shaken with 120 ml of diethyl ether and 80 ml of saturated aqueous ammonium chloride. The organic layer is then washed with 15 ml of brine, dried over magnesium sulfate, and concentrated under reduced pressure to yield 2.21 g of formula LVI product as a mixture of isomers: 3-[α-acetoxy-o-(t-butyldimethylsilyloxyethyl)-α-tolyl]-3-phenylsulfonyl-7α-(tetrahydropyran-2-yl)oxy-6β-[(3′S)-3′-(tetrahydropyran-2-yl)oxy-trans-1′-octenyl]bicyclo[3.3.0]octane. $R_{28}$, g, $R_{17}$, n, $R_{18}$, $Y_1$, $M_6$, $L_1$, and $R_{27}$ are defined in Examples 9 and 11. Silica gel TLC $R_f$ range is 0.30–0.53 (8 spots) (stereoisomers) in 25% ethyl acetate and hexane.

B. The mixture of isomeric products of Part A (2.21 g) and 40 ml of methanol and 20 ml of ethyl acetate is stirred at −20° C. with chips of 5.6% sodium amalgam for 60 min. After decanting liquid, excess amalgam and solids are rinsed by decantation employing 200 ml of diethyl ether. The organic solutions are then combined, washed with brine, dried, and concentrated under reduced pressure to yield 1.8 g of crude 2-decarboxy-2-(t-butyldimethylsilyloxymethyl)-2,5-inter-o-phenylene-3,4-dinor-CBA$_2$, 11,15-bis(tetrahydropyranyl ether). Chromatography on 250 g of silica gel, deactivated with 50 ml of diethyl ether and eluted with 30% diethyl ether in hexane yields 1.06 g of pure product. Silica gel TLC $R_f$'s are 0.49, 0.56, and 0.62 (stereoisomers) in 30% diethyl ether and hexane. NMR absorptions are observed at 7.20, 6.54, 5.22–5.80, 4.72, 3.38–4.16 and 2.74–3.00δ.

C. A solution of 1.06 g of the reaction product of Part B in 10 ml of dry tetrahydrofuran is treated with 3.2 ml of 0.75 N tetra-n-butylammonium fluoride in tetrahydrofuran at ambient temperature for 40 min. The resulting mixture is then diluted with 125 ml of diethyl ether. The resulting solution is then washed with brine, dried over magnesium sulfate, and concentrated under reduced pressure to yield a residue of isomeric formula LVIII products: (5E)- and (5Z)-2-decarboxy-2-hydroxymethyl-2,5-inter-o-phenylene-3,4-dinor-CBA$_2$, 11,15-bis-(tetrahydropyranyl ether). Chromatography on 100 g of silica gel, deactivated with 20 ml of ethyl acetate and eluted with 25–50% ethyl acetate in hexane yields 0.40 g of (5Z) isomer and 0.51 g of (5E) isomer. For the (5Z) isomer silica gel TLC $R_f$'s are 0.31 and 0.35 (stereoisomers) in 25% ethyl acetate and hexane. NMR absorptions are observed at 7.20, 6.51, 5.10–5.72, 4.69, 3.32–4.16, and 2.76–3.00δ. For the (5E) isomer silica gel TLC $R_f$'s are 0.20 and 0.24 (stereoisomers) in 25% ethyl acetate and hexane. NMR absorptions are observed at 7.19, 6.50, 5.10–4.64, 4.70, 3.32–4.10, and 2.88–3.01δ.

D. To a solution of 400 mg of the (5Z) reaction product of Part C in 20 ml of dry acetone at −50° C. is added with stirring 1.0 ml of Jones reagent (prepared as follows: 26.72 g of chromium trioxide in 23 ml of concentrated sulfuric acid diluted with water to a volume of 100 ml). The resulting mixture is then allowed to warm to −20° C. over a 20 min period and stirred at −20° C. for 30 min. Excess Jones reagent is then destroyed by addition of 0.5 ml of isopropanol. After 5 min the reaction mixture is then shaken in 100 ml of ethyl acetate and 80 ml of brine containing 0.5 ml of concentrated hydrochloric acid. The organic layer is then washed twice in 50 ml of water containing a trace (10 drops) of concentrated hydrochloric acid, twice in 50 ml of water and in brine. The organic layer is then dried over magnesium sulfate and concentrated under reduced pressure to yield 360 mg of crude (5Z)-2,5-inter-o-phenylene-3,4-dinor-CBA$_2$, 11,15-bis(tetrahydropyranyl ether), a formula LIX compound. Crude formula LIX compound is then taken up in 30 ml of diethyl ether and extracted in the mixture of 15 ml of water and 5 ml of methanol containing a trace amount (10 drops) of 45% aqueous potassium hydroxide. The extraction is repeated 6 times, until the acid is completely extracted from the ethereal solution. The aqueous extracts are then acidified to pH2 and extracted with ethyl acetate. The organic extract is then washed with brine, dried over magnesium sulfate, and concentrated under reduced pressure to yield a residue of pure title product. Silica gel TLC is a streak of about $R_f$ 0.50 in ethyl acetate and hexane (1:1). Purified acid is then converted to the corresponding ethyl ester by treatment with excess ethereal diazomethane for 10 min. Following esterification, the resulting reaction mixture is treated with ethyl acetate and washed with dilute aqueous potassium hydroxide and brine. After drying and concentrating to a residue, chromatography on 20 g of silica gel deactivated with 4 ml of ethyl acetate and elution with 10% ethyl acetate in trichloromethane yields 210 mg of (5Z)-2,5-inter-o-phenylene-3,4-dinor-$CBA_2$, methyl ester, 11,15-bis(tetrahydropyranyl ether). Silica gel TLC $R_f$'s are 0.52, 0.56, and 0.60 (stereoisomers) in 25% ethyl acetate and hexane. NMR absorptions are observed at 7.20, 6.45, 5.34–5.78, 4.70, 3.68, and 3.30–4.28$\delta$.

E. A mixture of 200 mg of methyl ester of Part D, 5 ml of acetic acid, 2.5 ml of water, and 1 ml of tetrahydrofuran is heated to 40° C. and stirred for 4 hr. The resulting mixture is then diluted with 100 ml of ethyl acetate and washed with a mixture of 6 g of 85% aqueous potassium hydroxide in 20 ml of water and 30 g of ice, washed with brine (40 ml), dried over magnesium sulfate, and concentrated under reduced pressure to yield 180 mg of crude (5Z)-2,5-inter-o-phenylene-3,4-dinor-$CBA_2$, methyl ester. Chromatography on 20 g of silica gel deactivated with 4 ml of ethyl acetate and elution with 100 ml of 50% ethyl acetate in trichloromethane and 100 ml of 50% acetone in trichloromethane yields 105 mg of pure product. Silica gel TLC $R_f$ is 0.57 in 40% acetone and trichloromethane and 0.52 in ethyl acetate. NMR absorptions are observed at 7.20, 6.43, 5.45–5.59, 3.65, 3.40–4.20, and 3.18$\delta$. The mass spectrum of the bis TMS derivative exhibits peaks of decreasing intensity at m/e 73, 75, 74, 147, 43, 129, 41, 45, 167, 59, and an $M^+$-$C_5H_{11}$ peak at 485.2513.

F. To a solution of 105 mg of the reaction product of Part E in 5 ml of methanol and 2.5 ml of water under a nitrogen atmosphere is added 0.33 g of potassium carbonate. The resulting mixture is stirred at ambient temperature for 20 hr whereupon a small quantity (5 drops) of 45% aqueous potassium hydroxide is added. The resulting mixture is stirred for an additional 4 hr at ambient temperature. Thereupon the mixture is shaken with 100 ml of ethyl acetate and excess cold dilute aqueous hydrochloric acid. The organic layer is then washed with brine, dried, and concentrated under reduced pressure to yield 100 mg of pure (5Z)-2,5-inter-o-phenylene-3,4-dinor-$CBA_2$. Silica gel TLC $R_f$ is 0.56 in the A-IX solvent system (the organic phase of an equilibrated mixture of ethyl acetate, acetic acid, cyclohexane, and water, 9:2:9:10). The mass spectrum of the tris TMS derivative exhibits peaks of decreasing intensity at m/e 73, 75, 129, 167, 74, 55, 69, 57, 147, and 45 and an $M^+$-$CH_3$ peak at 599.3418.

G. Following the procedure of Part D, 510 mg of the (5E) reaction product of Part C is transformed to 310 mg of (5E)-2,5-inter-o-phenylene-3,4-dinor-$CBA_2$, 11,15-bis(tetrahydropyranyl ether). Silica gel TLC $R_f$ is 0.41 in 25% ethyl acetate and hexane con-taining 1% acetic acid, and 220 mg of (5E)-2,5-inter-o-phenylene-3,4-dinor-$CBA_2$, 11,15-bis(tetrahydropyranyl ether)-methyl ester. Silica gel TLC $R_f$'s are 0.48, 0.51, and 0.56 (stereoisomers) in 25% ethyl acetate and hexane. NMR absorptions are observed at 7.20, 6.43, 5.26–5.64, 4.70, 3.65, and 3.30–4.10$\delta$.

H. Following the procedure of Part E, the reaction product of Part G (210 mg) is transformed to 110 mg of (5E)-2,5-inter-o-phenylene-3,4-dinor-$CBA_2$, methyl ester. Silica gel TLC $R_f$ is 0.57 in 40% acetone and trichloromethane and 0.46 in ethyl acetate. NMR absorptions are observed at 7.22, 6.44, 5.32–5.47, 3.68, 3.50–4.08, and 3.10$\delta$. The mass spectrum of the bis TMS derivative exhibits peaks of decreasing intensity at m/e 73, 75, 129, 227, 167, 55, 57, 173, 74, 466 and an $M^+$-$CH_3$ peak at 541.3198.

I. Following the procedure of Part F, the reaction product of Part H (110 mg) is transformed to 102 mg of (5E)-2,5-inter-o-phenylene-3,4-dinor-$CBA_2$. Silica gel TLC Rf is 0.50 in the A-IX solvent system. The mass spectrum of the tris TMS derivative exhibits peaks of decreasing intensity at m/e 73, 75, 167, 129, 524, 453, 285, 147, 434, 213, and an $M^+$-$CH_3$ peak at 599.3424.

EXAMPLE 13

(5E)-1,5-inter-m-phenylene-2,3,4-trinor-$CBA_2$, its methyl ester, and the corresponding (5Z) isomers Refer to Chart D.

A. Following the procedure of Example 12, Part A, a solution of 1.26 g of the title product of Example 11 and 0.62 g of the title product of Example 10 are transformed to 2.3 g of formula LVI compound. Silica gel TLC $R_f$ range is 0.37–0.56 (7 spots) (stereoisomers) in 25% ethyl acetate in hexane.

B. Following the procedure of Example 12, Part B, the reaction product of Part A (2.3 g) is transformed to 1.0 g of isomeric formula LVII compounds: (5E)- and (5Z)-2-decarboxy-2-(t-butyldimethylsilyloxymethyl)-1,5-inter-m-phenylene-2,3,4-trinor-$CBA_2$, 11,15-bis(tetrahydropyranyl ether). Silica gel TLC $R_f$'s are 0.47, 0.54 and 0.58 (stereoisomers) in 30% diethyl ether and hexane.

C. Following the procedure of Example 12, Part C, 1.0 g of the isomerically mixed reaction product of Part B is transformed to 0.51 g of (5Z)-2-decarboxy-2-hydroxymethyl-1,5-inter-m-phenylene-2,3,4-trinor-$CBA_2$, 11,15-bis(tetrahydropyranyl ether) and 0.40 g of (5E)-2-decarboxy-2-hydroxymethyl-1,5-inter-m-phenylene-2,3,4-trinor-$CBA_2$, 11,15-bis(tetrahydropyranyl ether). For the (5Z)-isomer, silica gel TLC $R_f$'s are 0.31 and 0.35 (stereoisomers) in 25% ethyl acetate and hexane. NMR absorptions are observed at 7.18, 6.36, 5.19–5.65, 4.63, 4.58, 3.31–4.08, and 2.92$\delta$. For the (5E)-isomer, silica gel TLC $R_f$'s are 0.23 and 0.27 (stereoisomers) in 25% ethyl acetate and hexane. NMR absorptions are observed at 7.19, 6.37, 5.29–5.72, 4.67, 4.60, 3.30–4.17, and 2.78$\delta$.

D. Following the procedure of Example 12, Part D, 510 mg of the (5Z) reaction product of Part C is transformed to 310 mg of (5Z)-1,5-inter-m-phenylene-2,3,4-trinor-$CBA_2$, 11,15-bis(tetrahydropyranyl ether) and 240 mg of (5Z)-1,5-inter-m-phenylene-2,3,4-trinor-$CBA_2$, methyl ester, 11,15-bis(tetrahydropyranyl ether). For the acid, silica gel TLC streak to about $R_f$ 0.54 in 50% ethyl acetate and hexane. For the methyl ester, silica gel TLC $R_f$'s are 0.58, 0.63, and 0.68 (stereoisomers) in 25% ethyl acetate and hexane. NMR absorptions are observed at 7.28–8.00, 6.40, 5.13–5.73, 4.71, 3.89, and 3.28–4.08δ.

E. Following the procedure of Example 12, Part E, 240 mg of the methyl ester product of Part D is transformed to 140 mg of (5Z)-1,5-inter-m-phenylene-2,3,4-trinor-CBA$_2$, methyl ester. Silica gel TLC R$_f$ is 0.49 in ethyl acetate. NMR absorptions are observed at 7.28–7.93, 6.40, 5.34–5.48, 3.88, and 3.32δ. The mass spectrum of the bis TMS derivative exhibits peaks of decreasing intensity at m/e 83, 85, 73, 47, 213, 75, 129, 48, 87, 77, and an M+-CH$_3$ peak at 527.2996.

F. To a solution of 140 mg of the reaction product of Part E in 6 ml of methanol under a nitrogen atmosphere is added a solution of 0.20 g of 85% potassium hydroxide in 2 ml of water. The resulting mixture is then stirred at ambient temperature for 7 hr, shaken with 200 ml of ethyl acetate and excess cold dilute aqueous hydrochloric acid. The organic layer is then washed with brine, dried over magnesium sulfate, concentrated under reduced pressure to yield 110 g of pure (5Z)-1,5-inter-m-phenylene-2,3,4-trinor-CBA$_2$. Silica gel TLC R$_f$ is 0.60 in the A-IX solvent system. The mass spectrum of the tris TMS derivative exhibits peaks of decreasing intensity at m/e 73, 271, 394, 129, 420, 510, 75, 147, 32, 74, and an M+-CH$_3$ peak at 585.3234.

G. Following the procedure of Example 12, Part D, 400 mg of the (5E) reaction product of Part C is transformed to 260 mg of (5E)-1,5-inter-m-phenylene-2,3,4-trinor-CBA$_2$, 11,15-bis(tetrahydropyranyl ether) and 190 mg of (5E)-1,5-inter-m-phenylene-2,3,4-trinor-CBA$_2$, methyl ester, 11,15-bis(tetrahydropyranyl ether). For the acid silica gel TLC streak to about R$_f$ 0.36 in 50% ethyl acetate and hexane. For the methyl ester, silica gel TLC R$_f$'s are 0.50, 0.53, and 0.57 (stereoisomers) in 25% ethyl acetate and hexane. NMR absorptions are observed at 7.38–7.95, 6.42, 5.13–5.75, 4.68, 3.89, and 3.30–4.09δ.

H. Following the procedure of Example 12, Part E, 190 mg of the reaction product of Part G is transformed to 81 mg of (5E)-1,5-inter-m-phenylene-2,3,4-trinor-CBA$_2$, methyl ester. Silica gel TLC R$_f$ is 0.51 in ethyl acetate. NMR absorptions are observed at 7.30–7.93, 6.43, 5.45–5.59, 3.89, 3.50–4.14, and 3.09δ. The mass spectrum of the bis TMS derivative exhibits peaks of decreasing intensity at m/e 73, 213, 129, 75, 83, 452, 173, 85, 262, 362, and an M+-CH$_3$ peak at 527.2996.

I. Following the procedure of Example 13, Part F, 81 mg of the reaction product of Part H is transformed to 65 mg of (5E)-1,5-inter-m-phenylene-2,3,4-trinor-CBA$_2$. Silica gel TLC R$_f$ is 0.60 in the A-IX solvent system. The mass spectrum of the tris TMS derivative exhibits peaks of decreasing intensity at m/e 73, 271, 394, 75, 510, 129, 420, 147, 173, 395, and an M+-CH$_3$ peak at 585.3227.

Following the procedure of Examples 12–13, but employing each of the various formula LV compounds described in and following Example 11 in each of the various formula XLIV described in and following Examples 9 and 10, there are prepared each of the various formula L compounds in free acid or methyl ester form.

EXAMPLE 14

9β-methyl-CBA$_2$, methyl ester, 11,15-bis(tetrahydropyranyl ether) (Formula LXXXIV: R$_{16}$ is hydrogen, R$_{37}$ is methyl, Z$_2$ is —(CH$_2$)$_3$— and R$_{18}$, Y$_1$, M$_6$, L$_1$, and R$_7$ are as defined in Example 3) and the corresponding (5E) and (5Z) free acids (formula LXXXIII)

Refer to Chart G.

A. A suspension of 57% sodium hydride in mineral oil (1.90 g) is washed with hexane and treated with 130 ml of dry dimethyl sulfoxide (DMSO). The resulting suspension is heated at 65° C. for 1 hr under a nitrogen atmosphere and the resulting solution cooled to 15° C. and treated dropwise over 15 min with 10.0 g of 4-carboxybutyltriphenylphosphonium bromide. The resulting orange solution is stirred for 15 min at 10° C. and then treated dropwise over 15 min with a solution of 2.12 g of the title product of Example 3 in 20 ml of dry DMSO. The resulting solution is then stirred at ambient temperature under a nitrogen atmosphere for 60 hr, treated with 15 ml of water, stirred for 30 min at ambient temperature, added to 200 ml of ice water and 100 ml of brine, acidified with 1 N aqueous hydrochloric acid, and extracted with 900 ml of diethyl ether. The ethereal extracts are then washed with 1 l of water and 200 ml of brine, dried over sodium sulfate, and concentrated under reduced pressure to yield 4.8 g of a yellow oil, the formula LXXXIII carboxylic acid.

B. The formula LXXXIII product and 42 ml of diisopropylethylamine in 120 ml of acetonitrile at 10° C. under a nitrogen atmosphere is treated with 15 ml of methyl iodide and allowed to warm slowly to ambient temperature. The resulting suspension is then stirred for 16 hr, treated with 3.0 ml of methyl iodide, stirred for an additional 2 hr, added to 500 ml of brine, and extracted with 1 l of ethyl acetate. The organic extracts are then washed with 250 ml of 0.5 N potassium bisulfate, 250 ml of saturated aqueous sodium bicarbonate, 250 ml of brine, dried over anhydrous sodium sulfate, and concentrated under reduced pressure to yield a solid residue. The residue is then chromatographed on 500 g silica gel, eluting with 8% acetone in hexane to yield 2.25 g of title formula LXXXIV product. NMR absorptions (CDCl$_3$) are observed at 0.9, 1.05, 1.08, 3.66, 3.02–4.35, 4.70, and 4.95δ. Infrared absorptions are observed at 1730, 1670, 1645, 1200, 1165, 1135, 1080, 1035, 1020, 980, and 870 cm$^{-1}$. Silica gel TLC R$_f$ is 0.46 in ethyl acetate and hexane (1.3) and 0.26 in ethyl acetate and hexane (1:6).

C. Alternatively the isomeric formula LXXXIII reaction products of Part A are separated into the (5E) and (5Z) title free acid products by chromatography on acid washed silica gel eluting with 10–30% ethyl acetate in hexane.

Following the procedure of Example 9, but employing each of the various formula LXXXI ketones in place of the Example 3 product, there are prepared each of the various formula LXXXIV methyl esters wherein Z$_2$ is —(CH$_2$)$_3$—.

Further following the procedure of Example 14, but employing a formula LXXXII ω-carboxytriphenylphosphonium compound wherein Z$_2$ is other than —(CH$_2$)$_3$—, each of the various formula LXXXI ketones is transformed to corresponding formula LXXXIV ester wherein Z$_2$ is other than —(CH$_2$)$_3$—.

EXAMPLE 15

(5Z)-2-Decarboxy-2-hydroxymethyl-9β-methyl-CBA$_2$, 11,15-bis(tetrahydropyranyl ether) (Formula LXXXVI: $R_{16}$, $R_{37}$, $Z_2$, $R_{18}$, $M_6$, $L_1$, and $R_7$ are as defined in Example 14) and its (5E) isomer (formula LXXXVII)

Refer to Chart G.

A suspension of 0.16 g of lithium aluminum hydride in 45 ml of dry tetrahydrofuran at 0° C. under a nitrogen atmosphere is treated dropwise with 1.98 g of the title product of Example 14 is 15 ml of dry tetrahydrofuran. The resulting suspension is stirred for 1 hr at 0° C. and thereafter for 1 hr at ambient temperature. The resulting mixture is then cooled to 0° C., quenched by addition of 0.16 ml of water, 0.16 ml of 15% aqueous sodium hydroxide. After stirring for 1 hr at ambient temperature, treatment with magnesium sulfate and filtration with diatomaceous earth, rinsing with diethyl ether, yields a mixture which is concentrated under reduced pressure. The resulting product, 0.25 g, is chromatographed on 180 g of silica gel, eluting with 30% ethyl acetate in hexane to yield 1.03 g of the formula LXXXVII product and 1.06 g of formula LXXXVI product. For the formula LXXXVI product NMR absorptions (CDCl$_3$) are observed at 0.90, 1.09, 3.2–4.4, 4.72, 5.0–5.9δ. Infrared absorptions are observed at 3470, 1760, 1200, 1135, 1120, 1075, 1035, 1020, and 980 cm$^{-1}$. Silica gel TLC R$_f$ is 0.29 in ethyl acetate and hexane (35:65). For the formula LXXXVII product NMR absorptions (CDCl$_3$) are observed at 0.90, 1.05, 3.2–4.4, 4.6–4.95, 5.05–5.97δ. Infrared absorptions are observed at 3470, 1670, 1200, 1125, 1110, 1080, 1035, 1020, and 985 cm$^{-1}$. Silica gel TLC R$_f$ is 0.36 in ethyl acetate and hexane (35.65).

Following the procedure of Example 15, but employing each of the various formula LXXXIV esters described following Example 14, there are prepared each of the respective formula LXXXVI and formula LXXXVII primary alcohols.

EXAMPLE 16

(5Z)-9β-methyl-CBA$_2$, methyl ester (Formula LXXXVIII: $X_1$ is —COOCH$_3$, $R_8$ is hydroxy, $M_1$ is α-OH:β-H, and $R_{16}$, $R_{17}$, $L_1$, $R_7$, $Y_1$, and $Z_2$ are as defined in Example 15)

Refer to Chart G.

A. A solution of the formula LXXXVI title product of Example 15 in 38 ml of acetone at −20° C. under a nitrogen atmosphere is treated over 5 min with 1.9 ml of Jones reagent (prepared by dissolving 133.6 g of chromium trioxide in 115 ml concentrated sulfuric acid and diluting with water to a volume of 500 ml), stirred for 2 hr at −20° C., quenched by addition of 2.3 ml of isopropanol, stirred for 40 min at −20° C., diluted with 200 ml of brine, extracted with 400 ml of ethyl acetate, washed with 600 ml of brine, dried over sodium sulfate, and concentrated under reduced pressure to yield 1.01 g carboxylic acid corresponding to the formula LXXXVI primary alcohol as a pale green oil.

B. A solution of the product of Part A in 11 ml of acetonitrile at 15° C. under a nitrogen atmosphere is treated with 4.1 ml of diisopropylethylamine and 1.5 ml of methyl iodide. The resulting suspension is then stirred at ambient temperature for 17 hr, treated with 0.3 ml of methyl iodide, stirred for 2 hr at ambient temperature, diluted with 50 ml of brine, extracted with 100 ml of ethyl acetate, washed with 50 ml of 0.5 M potassium bisulfate, 50 ml of aqueous sodium bicarbonate and 50 ml of brine, dried over anhydrous sodium sulfate, and concentrated under reduced pressure to yield 1.02 g of the methyl ester corresponding to the carboxylic acid product of Part A.

C. A solution of the product of Part B in 56 ml of a mixture of tetrahydrofuran, water, and acetic acid (1:2:4) is heated to 45° C. under a nitrogen atmosphere for 3 hr, cooled, diluted with 200 ml of brine, and extracted with 400 ml of diethyl acetate. The organic extracts are then washed with 600 ml of saturated acqueous sodium bicarbonate and 400 ml of brine, dried over anhydrous sodium sulfate, and concentrated under reduced pressure to yield 0.9 g of crude title product as a yellow oil. Chromatographing on 100 g of silica gel, eluting with hexane and ethyl acetate (3:7) yields 0.39 g of pure title product as a colorless oil. NMR absorptions (CDCl$_3$) are observed at 0.89, 1.08, 3.5–4.35, 3.66, 5.0–5.7δ. Infrared absorptions are observed at 3360, 1740, 1670, 1455, 1435, 1370, 1240, 1225, 1195, 1170, 1075, 1020, and 970 cm$^{-1}$. Silica gel TLC R$_f$ is 0.22 in ethyl acetate and hexane (7:3).

Following the procedure of Example 16, but employing each of the various formula LXXXVI compounds described following Example 15, there are prepared each of the various formula LXXXVIII 9β-methyl-CBA$_2$ compounds wherein $X_1$ is —COOR$_1$.

EXAMPLE 17

(5E)-9β-methyl-CBA$_2$, methyl ester (Formula LXXXIX: $R_{16}$, $R_{17}$, $X_1$, $Z_2$, $R_8$, $R_1$, $M_1$, $L_1$, $R_7$ are as defined in Example 16)

Refer to Chart G.

A. Following the procedure of Example 16, Part A, 0.60 g of the formula LXXXVII product of Example 15 is transformed to the carboxylic acid corresponding to the formula LXXXVII primary alcohol, yielding 0.66 g of a green oil.

B. Following the procedure of Example 16, Part B, the product of Part A above (0.66 g) is transformed to the methyl ester corresponding to the carboxylic acid product of Part A, yielding 0.58 g of a yellow oil.

C. Following the procedure of Example 16, Part C, the product of Part B above (0.58 g) is transformed to 0.25 g of title product as a colorless oil. NMR absorptions (CDCl$_3$) are observed at 0.90, 1.05, 3.30, 3.66, 3.75–4.25, 5.0–5.7δ. Infrared absorptions are observed at 3360, 1740, 1670, 1455, 1435, 1250, 1225, 1195, 1170, 1075, 1020, and 970 cm$^{-1}$. Silica gel TLC R$_f$ is 0.22 in ethyl acetate and hexane (3:7).

Following the procedure of Example 17, but employing each of the various formula LXXXVII compounds described following Example 15, there are prepared each of the various formula LXXXIX products wherein $X_1$ is —COOCH$_3$.

EXAMPLE 18

(5Z)-9β-methyl-CBA$_2$

A solution of 0.28 g of the title product of Example 16 in 8 ml of methanol is stirred at ambient temperature under a nitrogen atmosphere and treated with 1 ml of 8 M aqueous sodium hydroxide. The resulting yellow solution is then stirred for 5 hr at ambient temperature under a nitrogen atmosphere, diluted with 90 ml of ice and brine, acidified to pH2 with 1 N hydrochloric acid, extracted with 360 ml of ethyl acetate, washed with 120 ml of brine, dried over anhydrous sodium sulfate, and concentrated under reduced pressure to yield 0.25 g of crude title product. Chromatography on 30 g of silica gel, eluting with the A-IX solvent system (the organic phase of an equillibrated mixture of ethyl acetate, acetic acid, cyclohexane, and water, 9:2:5:10), yields 0.235 g of pure title product as a colorless oil. NMR absorptions (CDCl$_3$) are observed at 0.89, 1.08, 3.5-4.35, 5.0-5.7, 6.05$\delta$. Infrared absorptions are observed at 3340, 2660, 1710, 1240, 1205, 1175, 1130, 1075, 1055, 1020, and 970 cm$^{-1}$. Silica gel TLC R$_f$ is 0.25 in the A-IX solvent system.

Following the procedure of Example 18 each of the various methyl esters prepared following Example 16 is transformed to the corresponding carboxylic acid.

EXAMPLE 19

(5E)-9$\beta$-methyl-CBA$_2$

Following the procedure of Example 18, 0.25 g of the title product of Example 17 is transformed to 0.21 g of title product as a colorless oil. NMR absorptions (CDCl$_3$) are observed at 0.90, 1.06, 3.5-4.3, 5.0-5.7, and 4.93$\delta$. Infrared absorptions are observed at 3340, 2660, 1710, 1300, 1240, 1175, 1130, 1075, 1055, 1020, and 970 cm$^{-1}$. Silica gel TLC R$_f$ is 0.27 in the A-IX solvent system.

Each of the varous carboxylic acids corresponding to LXXXVIII and LXXXIX wherein X$_1$ is —COOH— can be prepared from the corresponding formula LXXXIII reaction products by acid hydrolysis of the tetrahydropyranyl ether protecting groups of C-11 and C-15. [The (5Z) LXXXIII reaction products from Example 14, Part C go to formula LXXXVIII products; and the (5E) LXXXIII reaction products from Example 14, part C go to formula LXXXIX products.]

Following the procedure of Example 19, but employing each of the various formula LXXXIX methyl esters described following Example 17, there are prepared each of the various corresponding carboxylic acids.

EXAMPLE 20

2$\beta$-(t-butyldimethylsilyloxymethyl)-5$\beta$-methyl-7-oxo-3$\alpha$-tetrahydropyran-2-yl-oxy-bicyclo[3.3.0]octane (Formula LXII: n is the integer one, R$_{31}$ is t-butyldimethylsilyl, and R$_{38}$ is tetrahydropyranyloxy).

Refer to Chart E.

A. A solution of 40.6 g of 3$\alpha$-benzoyloxy-5$\alpha$-hydroxy-2$\beta$-hydroxymethyl-1$\alpha$-cyclopentaneacetic acid, $\omega$-lactone in 250 ml of dimethylformamide, stirring at 0° C. under a nitrogen atmosphere, is treated with 25 g of imidazole in 28 g of t-butyldimethylsilyl chloride. The resulting solution is then stirred for 67 hr at ambient temperature, added to 500 ml of water, extracted with three 500 ml portions of diethyl ether, washed with 500 ml of 10% aqueous potassium bisulfate, 500 ml of aqueous sodium bicarbonate and 500 ml of brine, dried over sodium sulfate, and concentrated under reduced pressure to yield 59.9 g of 3$\alpha$-benzoyloxy-5$\alpha$-hydroxy-2$\beta$-(t-butyldimethylsilyloxymethyl)-1$\alpha$-cyclopentaneacetic acid, $\omega$ lactone as a white solid. NMR absorptions (CDCl$_3$) are observed at 0.06, 0.91, 2.1-3.12, 3.74, 4.94-5.54, 7.24-7.67, and 7.9-8.2$\delta$. Infrared absorptions are observed at 1780, 1720, 1600, 1585, 1490, 1270, 1255, 1180, 1115, 1100, 1070, 1050, 830, 790, and 710 cm$^{-1}$. Silica gel TLC R$_f$ is 0.20 in ethyl acetate and hexane (1:4).

B. A solution of 59.1 g of the reaction product of Part A and 500 of absolute methanol, stirring at ambient temperature under a nitrogen atmosphere, is treated with 35 ml of a 25% solution of sodium methoxide and methanol. The resulting reaction mixture is then stirred for 90 min at ambient temperature and quenched by addition of 9.5 ml of glacial acetic acid. Methanol is removed under reduced pressure and the resulting residue diluted with 500 ml of saturated aqueous sodium bicarbonate. The resulting mixture is then extracted with two 500 ml portions of ethyl acetate, washed with 300 ml of saturated aqueous sodium bicarbonate in 200 ml of brine, dried over sodium sulfate, and concentrated under reduced pressure to yield 58 g of an oily solid, crude 3$\alpha$,5$\alpha$-dihydroxy-2$\beta$-(t-butyldimethylsilyloxymethyl)-1$\alpha$-cyclopentaneacetic acid, $\omega$ lactone. This crude product is then chromatographed in 800 g of silica gel, eluting with 20-75% ethyl acetate in hexane to yield pure title product as a white crystal solid. Melting range is 60.5° C. to 62° C. NMR absorptions (CDCl$_3$) are observed at 0.06, 0.90, 1.7-3.0, 3.67, 3.9-4.4, and 4.7-5.13$\delta$. Silica ge TLC R$_f$ is 0.3 in 50% ethyl acetate in hexane.

C. A solution of 37.3 g of reaction product of Part B in 400 ml of methylene chloride, stirring at 0° C. under a nitrogen atmosphere, is treated with 18 ml of dihydropyran and 0.14 g of pyridine hydrochloride. The resulting solution is stirred at ambient temperature for 13 hr, treated with an additional 3 ml of dihydropyran and 30 mg of pyridine hydrochloride, stirred for an additional 4 hr, washed with two 400 ml portions of saturated aqueous sodium bicarbonate and 400 ml of brine, dried over anhydrous sodium sulfate, and concentrated under reduced pressure to yield 49 g of a pale yellow oil, crude 5$\alpha$-hydroxy-3$\alpha$-tetrahydropyran-2-yloxy-2$\beta$-(t-butyldimethylsilyloxymethyl)-1$\alpha$-cyclopentaneacetic acid, $\omega$ lactone. Chromatography on 800 g of silica gel, eluting with 0-75% ethyl acetate in hexane yields 37 g of pure product as a colorless oil. NMR absorptions (CDCl$_3$) are observed at 0.05, 0.90, 1.62, 2.0-3.0, 3.6, 3.2-4.4, 4.67, and 4.8-5.2$\delta$. Infrared absorptions are observed at 1780, 1255, 1175, 1160, 1116, 1080, 1035, 1020, 1005, 975, 835, and 775 cm$^{-1}$. Silica gel TLC R$_f$ is 0.25 in hexane and ethyl acetate (2:1).

D. A solution of 28 ml of dimethyl methylphosphonate in 800 ml of dry tetrahydrofuran at $-70°$ C. under a nitrogen atmosphere is treated with 160 ml of 1.56 M n-butyllithium in hexane, stirred for 30 min at $-70°$ C. The resulting mixture, maintained at $-70°$ C., is then treated dropwise over 30 min with 41.7 g of reaction product of Part C in 200 ml of tetrahydrofuran. The resulting solution is then stirred at $-70°$ C. for 1 hr, allowed to warm, stirred for an additional 2.5 hr at ambient temperature, quenched by addition of 14 ml of glacial acetic acid, added to 1 l of brine, extracted with three 700 ml portions of diethyl ether, washed with 500 ml of brine, dried over anhydrous sodium sulfate, and concentrated under reduced pressure to yield 63 g of a yellow oil, crude 6$\beta$-(t-butyldimethylsilyloxymethyl)-3-dimethylphosphonomethyl-3-hydroxy-2-oxa-7$\alpha$-tetrahydropyranyloxy-bicyclo[3.3.0]octane. Chromatography on 800 g of silica gel eluting with 50-75% ethyl acetate in hexane yields 44.2 g of pure title product as a colorless oil. NMR absorptions (CDCl$^3$) are observed at 0.05, 0.89, 1.23-3.02, 2.2-4.37, 4.70, and 4.99$\delta$. Infrared absorptions are observed at 3380, 1255, 2235, 1120, 1050, 1035, 835, and 775 cm$^{-1}$. Silica gel TlC R$_f$ is 0.25 in ethyl acetate.

E. A suspension of 29.2 g of chromium trioxide in 700 ml of methylene chloride, stirring at ambient temperature under a nitrogen atmosphere, is treated rapidly with 50 ml of pyridine, treated with dry diatomaceous earth, stirred for 5 min, and then treated with 23.8 g of title product of Part D in 60 ml of methylene chloride. The resulting suspension is then stirred for 45 min at ambient temperature under a nitrogen atmosphere and filtered through 300 g of silica gel, eluting with 2 l of ethyl acetate in acetone (2:1). Concentration under reduced pressure yields 24 g of a brown yellow oil, crude 3$\beta$-(t-butyldimethylsilyloxymethyl)-2$\alpha$-(2'-dimethylphosphonomethyl-2'-oxoethyl)-4$\alpha$-tetrahydropyranyloxy-pentanone. High pressure liquid chromatography of 12 g of the crude product on silica gel eluting with 20% acetone in methylene chloride yields 4.54 g of pure product as a colorless oil. NMR absorptions (CDCl$_3$) are observed at 0.05, 0.88, 2.8–4.5, 3.77, and 4.86$\delta$. Infrared absorptions are observed at 1745, 1715, 1255, 1130, 1115, 1060, 1025, 835, 810, and 775 cm$^{-1}$. Silica gel TLC R$_f$ is 0.27 in 20% acetone in methylene chloride and 0.3 in ethyl acetate.

F. A degassed suspension of 0.52 g reaction product of Part E, 0.15 g anhydrous potassium carbonate, and 0.59 g 18-crown-6 ether in 20 ml toluene are stirred at 75° C. for 6 hr under a nitrogen atmosphere and thereafter cooled to 0° C. The resulting solution is then washed successively with 20 ml brine, a solution of 15 ml water and 5 ml brine, and 20 ml brine, dried over anhydrous sodium sulfate, and concentrated to yield a brown residue crude 6$\beta$-t-butyldimethylsilyloxymethyl-7$\alpha$-tetrahydropyran-2-yl-oxybicyclo[3.3.0]oct-1-en-2-one, filtering through 7 g of silica gel and eluting with hexane and ethyl acetate (70 ml, 1:1) yields 0.31 g of product as an oil. High pressure liquid chromatography (10 ml fractions, 3.8 ml/minute flow rate) on silica gel, eluting with hexane and ethyl acetate (3:1) yields 0.20 g of pure product as a colorless oil. NMR absorption (CDCl$_3$) of the trimethylsilyl derivative are observed at 0.06, 0.90, 1.20–3.20, 3.20–4.85, and 5.85–6.0$\delta$. Infrared absorptions are observed at 1710, 1630, 1250, 1130, 1115, 1075, 1030, 965, 870, 835, 810, 775 cm$^{-1}$. Silica gel TLC R$_f$ is 0.34 in hexane and ethyl acetate (2:1).

G. A suspension of 0.35 g of anhydrous copper iodide in 12 ml of anhydrous diethyl ether at −20° C. under an argon atmosphere is treated dropwise with 2.0 ml of 1.4 M methyllithium. The resulting solution is then stirred at −20° C. for 15 min, treated at −20° C. dropwise over 1.5 hr with a solution of 0.22 g of the reaction product of Part F in 12 ml of anhydrous diethyl ether. The resulting suspension is then stirred at −20° C. for 2 hr, added to 50 ml of 1 M aqueous ammonium chloride, extracted with 150 ml of diethyl ether, washed with 50 ml of brine, dried over anhydrous sodium sulfate, and concentrated under reduced pressure to yield 0.23 g of crude title product as a pale yellow oil. Chromatography on 30 g of silica gel, eluting with ethyl acetate and hexane (1:4) yields 0.22 g of pure title product as a colorless oil. NMR absorptions (CDCl$_3$) are observed at 0.05, 0.90, 1.16, 1.3–2.9, 3.3–4.4, and 4.63$\delta$. Infrared absorptions are observed at 1745, 1255, 1135, 1110, 1095, 1075, 1035, 1029, 835, and 775 cm$^{-1}$. Silica gel TLC R$_f$ is 0.32 in ethyl acetate and hexane (1:4).

EXAMPLE 21

N-methyl-(1-fluoro-5-tetrahydropyranyloxypentyl)-phenylsulfoximine (Formula XCII: Z$_2$ is —(CH$_2$)$_3$— and R$_{10}$ is tetrahydropyranyl Refer to Chart H.

Diisopropylamine (0.59 g) is dissolved in 21 ml of tetrahydrofuran and the resulting mixture cooled to −78° C. with stirring under an argon atmosphere. Thereafter triphenylmethane is added, for use as an indicator, and a solution of n-butyllithium and hexane is added dropwise until the resulting mixture attains a pink color. After stirring for an additional 75 min, the resulting mixture is treated with 1.50 g of N-methyl-(5-tetrahydropyranyloxypentyl)-phenylsulfoximine dissolved in 6 ml of dry tetrahydrofuran. The resulting mixture is then stirred for an additional 30 min at −78° C. Thereafter excess perchloryl fluoride (FClO$_3$) is bubbled through the solution for 4–5 min, during which time a stream of argon is also bubbled through the mixture for safety reasons. The resulting mixture is then stirred at additional 90 min at −78° C. and then the reaction is quenched by addition of 5% aqueous sodium bicarbonate. After equilibration of the reaction mixture to ambient temperature, the mixture is diluted with additional 5% aqueous sodium bicarbonate and extracted with methylene chloride. The organic extracts are then washed with brine, dried over magnesium sulfate, and concentrated under reduced pressure to yield 1.64 g of a yellow oil. Chromatography on silica gel columns in a series, eluting with ethyl acetate and hexane (1:1) yields 0.18 g of the formula XCII title product as a mixture of diastereomers. Silica gel TLC R$_f$ in ethyl acetate and hexane (1:1) are 0.54 (less polar isomer) and 0.45 (more polar isomer). NMR absorptions (CDCl$_3$) for the less polar isomer are 1.2–2.15, 3.65, 3.68, 3.1–4.1, 4.4–4.8, 5.5, and 7.4–8.1$\delta$. NMR absorptions (CDCl$_3$) for the more polar isomer are 1.15–2.20, 3.63, 3.1–4.1, 4.45–4.65, 5.27, and 7.4–8.1$\delta$.

Following the procedure of Example 21, but employing each of the various formula XCI phenylsulfoxamines, there are prepared each of the various corresponding formula XCII fluorinated phenylsulfoxamines.

EXAMPLE 22

5-Fluoro-2-decarboxy-2-hydroxymethyl-CBA$_2$, 1,11,15-tris(tetrahydropyranyl ether). (Formula XCIV: R$_{16}$ and R$_{17}$ are both hydrogen, R$_{10}$ is tetrahydropyranyl, Z$_2$ is —(CH$_2$)$_3$—, n is the integer one, R$_{18}$ is tetrahydropyranyloxy, Y$_1$ is trans-CH=CH—, M$_6$ is $\alpha$-tetrahydropyranyloxy:$\beta$-hydrogen, R$_3$ and R$_4$ of the L$_1$ moiety are both hydrogen, and R$_7$ is n-butyl)

Refer to Chart H.

Diisopropylamine (164 mg) and triphenylmethane (1.5 mg) are dissolved in 4 ml of dry tetrahydrofuran and the resulting solution is cooled to −78° C. under a nitrogen atmosphere. A solution of n-butyllithium and hexane is added until a faint pink color is attained. This solution is then stirred an additional 80 min. Thereafter, 0.488 g of the title product of Example 21 in 4 ml of dry tetrahydrofuran is added dropwise. Thereafter 608 mg of 7-oxo-3$\alpha$-tetrahydropyran-2-yl-oxy-2$\beta$-[(3'S)-3'-tetrahydropyran-2-yloxy-trans-1'-octenyl] bicyclo[3.3.-0]octane (Formula XCIII: R$_{16}$, R$_{17}$, n, R$_{18}$, Y$_1$, M$_6$, L$_1$, and R$_7$ are as defined for the title product) in 4 ml of tetrahydrofuran is added to the reaction mixture. After 4 min, the resulting mixture is quenched by addition of saturated aqueous ammonium chloride and ethyl acetate is thereafter added to the reaction mixture, which is maintained at −78° C. The resulting mixture is then allowed to warm until solids separate. Thereupon additional ethyl acetate is added, the reaction extracted with brine. The ethyl acetate layer is then dried over sodium sulfate and concentrated under reduced pressure.

An aluminum amalgam is then prepared by reacting 0.31 g of 20 mesh aluminum with 2.5 ml of aqueous mercuric chloride followed by washing with ethyl acetate and diethyl ether. The residue from the ethyl acetate layer (described in the preceeding paragraph) is dissolved in 5 ml of tetrahydrofuran and the solution cooled to 0° C. This cooled solution is then treated with aluminum amalgam, 2 ml of water, and 1 ml of glacial acetic acid. The resulting mixture is then stirred for 2 hr at 0° C. and 16 hr at 20° C. The reaction is then diluted with ethyl acetate and filtered with diatomaceous earth. The ethyl acetate layer is then washed with 5% aqueous sodium bicarbanate and saturated brine, dried over sodium sulfate, and concentrated under reduced pressure to yield 0.96 g as an oily residue. Chromatographing over 100 g of silica gel and eluting with 500 ml of 15% ethyl acetate in mixed hexanes, 500 ml of 25% ethyl acetate in mixed hexanes, 300 ml of 50% ethyl acetate in mixed hexanes, and 800 ml of 50% acetone in methylene chloride, taking 20 ml fractions, yields a less polar isomer in fractions 22–26 (80 mg) and a more polar isomer in fractions 30–36 (74 mg). These isomers represent the C-5 diastereomers of the formula XCIV product. For the less polar isomer, NMR absorptions (CDCl$_3$) are observed at 0.65–2.65, 3.15–4.15, 4.35–4.75, and 5.25–5.75$\delta$. For the more polar isomer, NMR absorptions (CDCl$_3$) are observed at 0.6–2.65, 3.10–4.15, 4.40–4.7, and 5.2–5.7$\delta$. Silica gel TLC R$_f$ for the less polar isomer is 0.66 and for the more polar isomer is 0.57 in ethyl acetate and mixed hexanes (3:7).

Following the procedure of Example 22, but employing each of the various formula XCIII ketones, there are obtained each of the various formula XCIV intermediates wherein Z$_2$ is —(CH$_2$)$_3$—.

Further following the procedure of Example 22, but substituting each of the various fluorinated phenylsulfoximines described following Example 21, there are prepared from the various formula XCIII ketones each of the various formula XCIV products wherein Z$_2$ is other than —(CH$_2$)$_3$—.

EXAMPLE 23

5-Fluoro-2-Decarboxy-2-hydroxymethyl-CBA$_2$ (more polar isomer) (Formula XCV: R$_{16}$, R$_{17}$, Z$_2$, n, R$_8$, M$_1$, L$_1$, and R$_7$ are as defined in Example 17)

Refer to Chart H.

The title product of Example 22 (74 mg) is dissolved in 2 ml of a mixture of tetrahydrofuran, water, and glacial acetic acid (2:2:1) and the resulting mixture stirred under a nitrogen atmosphere. The reaction mixture is maintained at ambient temperature for 17 hr, thereafter at 40° C. for 7 hr, and finally at 23° C. for an additional 24 hr. The resulting mixture is then diluted with ethyl acetate, washed with 5% aqueous sodium bicarbonate and saturated brine, dried over sodium sulfate, and concentrated under reduced pressure to yield 52 mg of crude title product. Chromatography over silica gel, eluting with acetone and methylene chloride (60:40) yields 19 mg of pure title product. NMR absorptions (CDCl$_3$) are observed at 0.6–2.60, 2.60–3.30, 3.30–4.15, 5.1–5.9$\delta$. $^{13}$C-NMR absorptions (CDCl$_3$) are observed at 135.8, 133.0, 117.5 (d J=18 Hz), 77.4, 73.3, 62.6, 57.6, 46.4, 44.1, 38.0, 37.2, 36.2 (d J=5 Hz), 31.9, 31.8, 31.2, 29.5 (d J=29 Hz), 25.2, 22.5, 14.0$\delta$. Silica gel TLC R$_f$ is 0.280 in acetone and methylene chloride (1:1).

EXAMPLE 24

5-Fluoro-2-decarboxy-2-hydroxymethyl-CBA$_2$ (less polar isomer)

Following the procedure of Example 23, 85 mg of less polar title product of Example 22 are transformed to 25 mg of pure title product. NMR absorptions (CDCl$_3$) are observed at 0.5–2.5, 3.1–4.75, and 5.05–5.8$\delta$. $^{13}$C-NMR absorptions (CDCl$_3$) are observed at 137.0, 132.6, 77.0, 73.6, 62.3, 57.4, 45.5, 41.6, 36.9, 36.5, 34.4 (d J=3.1 Hz), 32.5 (d J=5.4 Hz), 31.8, 31.7, 29.2 (d J=28.9 Hz), 25.4, 22.6, 22.4, and 14.0$\delta$. Silica gel TLC R$_f$ is 0.33 in acetone and methylene chloride.

Following the procedure of Examples 23 and 24, but employing the various diastereomeric products described following Example 22, there are prepared each of the various diastereomers corresponding to formula XCV.

EXAMPLE 25

5-fluoro-CBA$_2$ (more polar isomer) (Formula LXXVI: Z$_2$, n, R$_8$, Y$_1$, M$_1$, L$_1$, and R$_7$ are as defined in Example 23)

Refer to Chart H.

The platinum oxide catalyst is prepared by suspending 46 mg of 85% platinum oxide in 9 ml of water and hydrogenating the resulting mixture at ambient temperature and pressure for 34 min. To this suspension is added 58 mg of sodium bicarbonate and 18 mg of the title product of Example 23 dissolved in 2 ml of acetone. The resulting mixture is then warmed to 60° C. and oxygen bubbled therethrough for 80 min. The reaction mixture is then filtered through diatomaceous earth and the filter cake washed in water. The filtrate is then acidified to pH4 with 5% aqueous sodium hydrogen sulfate and extracted with ethyl acetate. The organic extracts are then dried over magnesium sulfate and concentrated under reduced pressure to yield 21 mg of pure title product. NMR absorptions (CDCl$_3$) are observed at 0.6–2.8, 3.0–4.2, and 4.65–5.8$\delta$. $^{13}$C-NMR absorptions (CDCl$_3$) are observed at 176.9, 135.5, 133.2, 118.5 (d J=17.5 Hz), 77.7, 73.5, 57.3, 46.5, 41.0, 38.2, 37.0, 36.2 (d J=4.8 Hz), 32.3, 31.7, 31.1 (d J=13.5 Hz), 28.5 (d J=28.3 Hz), 25.2, 22.6, 21.0, and 14.0$\delta$. Silica gel TLC R$_f$ is 0.39 in the A-IX solvent system.

EXAMPLE 26

5-Fluoro-CBA$_2$ (less polar isomer)

Following the procedure of Example 25, 24 mg of the title product of Example 24 yields 23 mg of pure title product. NMR absorptions (CDCl$_3$) are observed at 0.6–2.9, 3.3–4.2, 5.0–6.0$\delta$. $^{13}$C-NMR absorptions (CDCl$_3$) are observed at 176.8, 135.4, 132.9, 118.3 (d J=18.2 Hz), 77.6, 73.4, 57.2, 46.3, 41.2, 37.8, 36.8, 34.6 (d J=2.7 Hz), 32.8, 32.4, 31.7, 28.7(d J=28.4 Hz), 25.2, 22.6, 21.1, and 14.0$\delta$. TLC R$_f$ is 0.50 in the A-IX solvent system.

The reaction products of Example 25–26 are obtained as diastereomeric mixtures of (5E) and (5Z) geometric isomers. These geometric isomers are characterized herein as "less polar" and "more polar" isomers based on TLC motilities. The isomers of these 5-fluoro-CBA$_2$ compounds correspond to the (5E) and (5Z) geometric isomers of CBA$_2$ itself. On the basis of relative biological activities, the more polar 5-fluoro-CBA$_2$ isomer yields more potent pharmacological effects and on this basis could be assigned the (5Z) structure based on pharmacological considerations alone. However, the $^{13}C$-NMR data suggests the more polar isomer corresponds to the (5E) structure of the 5-fluoro-CBA$_2$ compound.

Following the procedure of Examples 25–26, there are prepared each of the various formula XCVI 5-fluoro-CBA$_2$ diastereomers from the starting materials described following Example 24.

Further following the procedures known in the art, each of the various 5-fluoro-CBA$_2$ compounds described in and following Examples 24–25 is transformed to the corresponding formula XCVII 5-fluoro-CBA$_2$ analogs.

EXAMPLE 27

(5Z)-9β-methyl-CBA$_2$ adamantylamine salt

The title product of Example 18 (54 mg), (5Z)-9β-methyl-CBA$_2$ in 6 ml of diethyl ether is combined with 23 mg of adamantylamine. After 10 min the precipitate forms which is thereafter stirred for 12 hr, decanted, and concentrated under reduced pressure to yield 68 mg of a solid, pure title product. Melting range is 110°–114° C.

EXAMPLE 28

(5Z)-9β-methyl-CBA$_2$, calcium salt hydrate

The title product of Example 18 (0.95 g), 9β-methyl-(5Z)-CBA$_2$, calcium oxide (0.064 g), freshly boiled water (9.2 ml), and distilled tetrahydrofuran (6 ml), are combined by heating to 50° C. under a nitrogen atmosphere with stirring for 20 min. The resulting mixture is then filtered, washed with tetrahydrofuran, and concentrated under reduced pressure to yield a residue. The residue is then dissolved in tetrahydrofuran (10 ml) and concentrated 8 times to yield a cream-colored foam. This foam is then dissolved in 6 ml of tetrahydrofuran which is dripped into anhydrous diethyl ether (95 ml). The resulting suspension is then stirred for 15 min at ambient temperature under a nitrogen atmosphere and filtered. The filter cake is then washed with anhydrous diethyl ether and dried for 20 hr under reduced pressure at ambient temperature to yield 0.686 g of title product. Melting range is 101°–108° C. Following atmospheric equillibration melting range is 80°–117° C. Infrared absorptions are observed at 3330, 1670, 1555, 1455, 1345, 1310, 1270, 1075, 1020, 970 cm$^{-1}$.

EXAMPLE 29

8α-hydroxy-7β-(3α-hydroxy-trans-1-octenyl)-tricyclo-[4.3.1]nonan-4-one, 8,3'-bis(tetrahydropryanyl ether) (Formula XXV: R$_{18}$, Y$_1$, M$_6$, L$_1$, R$_{27}$, and n are as defined in Example 1, R$_{16}$ and R$_{37}$ taken together are—CH$_2$—).

Refer to Chart A.

A. The formula XXIV title product of Example 1 (4.0 g) and benzophenone (2 g) in one liter of methanol is photolyzed (3500 Å lamp) for 3 hr while argon is bubbled through the solution. The methanol is then removed by concentration under reduced pressure and the residue chromatographed on 600 g of silica gel eluting with a mixture ranging from ethyl acetate in hexane (1:3) to 100% ethyl acetate. Compound XXVI, 1β-hydroxymethyl-7α-hydroxy-6β-(3'α-hydroxy-trans-1'-octenyl)bicyclo[3.3.0]octan-3-one, 7,3'-bis(tetrahydropyranyl ether) is obtained as a white solid (3.45 g). Crystallization from ethyl acetate in hexane yields a white solid with melting range 65°–70° C. NMR absorptions (CDCl$_3$) are observed at 0.89, 1.17–2.90, 2.92–4.40, 4.69, and 5.24–5.77δ. Infrared aborptions are observed at 3420, 1730, 1200, 1125, 1110, 1070, 1040, 1020, and 970 cm$^{-1}$. Silica gel TLC R$_f$ is 0.29 in hexane and ethyl acetate (1:4).

B. A solution of 0.6 g of the reaction product of Part A and 0.49 g of p-toluenesulfonyl chloride in 30 ml of pyridine is cooled to 0° C. under argon for 70 hr, added to 100 ml of ice, diluted with 300 ml of water, and extracted with diethyl ether (800 ml). The ethereal extracts are then washed with brine, dried over magnesium sulfate, concentrated under reduced pressure, and chromatographed eluting with 50% to 80% hexane in ethyl acetate to yield 0.49 g of formula XXVII compound, 3-oxo-7α-tetrahydropyran-2-yloxy-6β-[(3'α-)-3'-tetrahydropyran-2-yloxy-trans-1'-octenyl]-1β-(p-toluenesolfonyl)-oxymethylbicyclo[3.3.0]octane, as a colorless oil. NMR absorptions (CDCl$_3$) are observed at 0.88, 1.06–2.9, 2.45, 3.17–4.35, 4.52–4.83, 5.2–5.8, 7.37, and 7.81δ. Infrared absorptions are observed at 1740, 1600, 1360, 1200, 1190, 1175, 1130, 1110, 1075, 1035, 1020, 970, and 820 cm$^{-1}$. Silica gel TLC R$_f$ is 0.45 or 0.26 in ethyl acetate and hexane (1:1 or 1:2).

C. A degassed solution of 0.49 g of the reaction product of Part B and 1 ml of t-butanol in 50 ml of dry tetrahydrofuran at 0° C. under an argon atmosphere is treated with 0.8 ml of 1.7 M potassium t-butoxide in tetrahydrofuran. After 5 min the reaction is allowed to warm and the resulting brown solution stirred for 3 hr at ambient temperature. Thereafter 90 ml of brine is added and the mixture is extracted with 270 ml of ethyl acetate. The ethyl acetate extracts are then washed with 100 ml of saturated aqueous sodium bicarbonate, 100 ml of brine, dried over anhydrous magnesium sulfate, concentrated under reduced pressure, yielding 0.37 g of a brown oil, and chromatographed on 40 g of silica gel eluting with hexane and ethyl acetate (2:1) to yield 0.32 g of pure formula XXV title product as a colorless oil.

D. Alternatively, a suspension of 207 mg of 5% sodium hydride in mineral oil and 1.08 g of trimethyloxosulfonium iodide is treated dropwise under a nitrogen atmosphere with 6 ml of dimethylsulfoxide. The resulting grey slurry is then stirred at ambient temperature for 20 min, treated with 2.03 g of the title product of Example 1 in 4 ml of dry dimethylsulfoxide and stirred for 2 hr at ambient temperature. Thereafter stirring is continued for 1 hr at 50° C., the reaction mixture is cooled and diluted with 200 ml of water and thereafter extracted with three 100 ml portions of diethyl ether. The combined ethereal extracts are then washed with 200 ml of water, washed with 100 ml brine, dried over anhydrous magnesium sulfate, concentrated under reduced pressure, yielding a brown oil, and chromatographed on 250 g of silica gel eluting with ethyl acetate and hexane (1:2) to yield 453 mg of pure title product.

E. For title product prepared according to Part C or Part D above, NMR absorptions (CDCl$_3$) are observed at 0.25–2.75, 3.15–4.39, 4.68, and 5.2–5.8δ. Infrared absorptions are observed at 1725, 1665, 1135, 1080, 1040, 1020, 980 cm$^{-1}$.

The mass spectrum exhibits a molecular ion at 446 and silica gel TLC R$_f$ is 0.30 in ethyl acetate and hexane.

EXAMPLE 30

(5Z) and (5E)-6α$\beta$,9$\beta$-methano-CBA$_2$ (Formula X: $X_1$ is —COOH, $Z_1$ is —(CH$_2$)$_3$—, $R_{15}$ is hydrogen, $R_{16}$ and $R_{17}$ taken together are methano, n is one, $R_8$ is hydroxy, $Y_1$ is trans-CH=CH—, $M_1$ is α-OH:$\beta$-H, $L_1$ is α-H:$\beta$-H, $R_7$ is n-butyl, and the C-5, C-6 positions are unsaturated).

Refer to Chart G.

A. A suspension of 452 mg of 57% sodium hydride in mineral oil and 30 ml of dimethylsulfoxide is heated to 65° C. for 1 hr under a nitrogen atmosphere, cooled to 17° C. and thereafter treated over 15 min with 2.39 g of 4-carboxybuthyltriphenylphosphonium bromide. The resulting red solution is then stirred for 15 min at 17°–20° C., treated with a solution of 716 mg of the title product of Example 29, 6 ml of dry dimethylsulfoxide, stirred for 43 hr at 40° C., cooled to 0° C., treated with 3.5 ml of water, stirred for 30 min at 0° C., added to 75 ml of water and brine (2:1), acidified with one N aqueous hydrochloric acid, and extracted with 225 ml of diethyl ether. The ethereal extracts are then washed with 375 ml of water and 75 ml of brine, dried over magnesium sulfate, concentrated under reduced pressure, and chromatographed on 150 g of acid-washed silica gel eluting with 10–25% ethyl acetate in hexane to yield 290 mg of (5Z)-6α$\beta$,9$\beta$-methano-CBA$_2$, 11,15-bis(tetrahydropyranyl ether), 70 mg of (5E)-6α$\beta$,9$\beta$-methano-CBA$_2$, 11,15-bis(tetrahydropyranyl ether), and 400 mg of a mixture of (5E) and (5Z) formula LXXXIII isomers. Rechromatographing the isomeric mixture on 150 g of acid-washed silica gel yields an additional 50 mg of (5E) isomer and 180 mg of (5Z) isomer.

For the (5Z) isomer NMR absorptions (CDCl$_3$) are observed at 0.5–2.85, 3.22–4.4, 4.70, 4.9–5.75, and 10.1$\delta$. Infrared absorptions are observed at 3600–3000 (a broad band), 1740, 1710, 1240, 1210, 1135, 1080, 1035, 1020, 980, and 870 cm$^{-1}$. Silica gel TLC R$_f$ is 0.27 in hexane, ethyl acetate, and acetic acid (65:34:1). For the (5E) isomer NMR absorptions are observed at 0.40–2.70, 3.2–4.4, 4.70, 5.0–5.8, and 8.82$\delta$. Infrared absorptions are observed at 3600–3000, 1740, 1710, 1460, 1445, 1200, 1135, 1075, 1035, 1020, and 980 cm$^{-1}$. Silica gel TLC R$_f$ is 0.32 in hexane, ethyl acetate, and acetic acid (65:34:1).

B. A solution of 446 mg of the (5Z) reaction product of Part A in 44 ml of acetic acid, water, and tetrahydrofuran (6:3:2) is heated at 45° C. under a nitrogen atmosphere for 3 hr, cooled, added to 200 ml of brine, extracted with 160 ml of ethyl acetate in hexane (3:2), washed with 500 ml of brine, extracted with 120 ml of ethyl acetate and hexane (3:2) dried over sodium sulfate, concentrated under reduced pressure, yielding 0.38 g of a yellow oil and chromatographed on 60 g of acid washed silica gel eluting with 70% ethyl acetate in hexane to yield 170 mg of pure (5Z) title product as a colorless oil. NMR absorptions are observed at 0.5–2.90, 0.89, 4.05, 4.85–5.8, and 6.13$\delta$. Infrared absorptions are observed at 3360, 2260, 1710, 1245, 1240, 1075, 1025, and 970 cm$^{-1}$. The mass spectrum for the tris-trimethylsilyl derivative exhibits a high resolution peak at 578.3653. Silica gel TLC R$_f$ is 0.30 in the A-IX solvent system (the organic phase of an equilibrated mixture of ethyl acetate, acetic acid, cyclohexane, and water; 9:2:5:10).

C. Following the procedure of Part B above 90 mg of the (5E) reaction product of Part A is converted to 46 mg of (5E) title product as a colorless oil. NMR absorptions are observed at 4.40–2.8, 0.89, 4.06, and 5.0–5.85$\delta$. Infrared absorptions are observed at 3340, 2630, 1710, 1070, 970 cm$^{-1}$. The mass spectrum exhibits a high resolution peak at 578.3664. Silica gel TLC R$_f$ is 0.32 in the A-IX solvent system.

Following the procedure of Examples 27–29, each of the various formula X products is prepared wherein $R_{16}$ and $R_{17}$ are methano from the corresponding formula LXXXI reactants of Chart G.

Accordingly, the above examples provide methods for preparing each of the various formula X CBA analogs of the present invention.

EXAMPLE 31

9-deoxy-2',9α-methano-3-oxa-4,5,6-trinor-3,7-(1',3'-inter-phenylene)-PGF$_{1\alpha}$ (Formula XI: $X_1$ is COOH, $R_{20}$, $R_{21}$, $R_{23}$, and $R_{24}$ are all hydrogen, $Z_4$ is —CH$_2$—, $R_{22}$ is $\beta$-hydrogen, $R_8$, $Y_1$, $M_1$, $L_1$, and $R_7$ are as defined in Example 8) and its corresponding methyl ester ($X_1$ is —COOCH$_3$)

Refer to Chart P.

A. A solution of methyl phenyl-N-methyl sulfoximine (3.39 g) in dry tetrahydrofuran (60 ml), is alternately degassed and flushed with nitrogen, cooled to −78° C. and treated dropwise over 7 min with 2.8 M methyl magnesium chloride (7.16 ml). The resulting solution is stirred at −78° C. for 30 min, then at 0° C. for 15 min. The reaction is cooled to −78° C. and treated with a solution of 3-oxa-1,2,4,5,6-pentanor-3,7-inter-m-phenylene-PGE$_1$, 3-(t-butyldimethylsilyl ether), 11,15-bis(tetrahydropyranyl ether) (6.05 g), a formula CLXXI compound, in dry tetrahydrofuran (35 ml). The resulting mixture is stirred for 1.75 hr while the temperature permitted to go from −78° C. to 0° C. and then stirred for one hr at 0° C. The reaction mixture is then diluted with brine (170 ml) and extracted with diethyl ether. The ethereal extracts are then washed successively with brine (170 ml), 0.5 M aqueous potassium bisulfate (170 ml), saturated aqueous sodium bicarbonate (170 ml) and brine (170 ml), dried over magnesium sulfate, filtered and concentrated to a yellow oil (8.0 g), 9-[(N-methyl)-phenylsulfoximinomethyl]-3-oxa-1,2,4,5,6-pentanor-3,7-inter-m-phenylene-PGF$_1$, 3-(t-butyldimethylsilyl ether), 11,15-bis(tetrahydropyranyl ether). A degassed solution of 9-[(N-methyl)phenylsulfoximinomethyl]-3-oxa-1,2,4,5,6-pentanor-3,7-inter-m-phenylene-PGF$_1$, 3-(t-butyldimethylsilyl ether), 11,15-bis(tetrahydropyranyl ether) (8.0 g) in tetrahydrofuran (150 ml) is cooled to 0° C., treated with 50% acetic acid/water (45 ml) then immediately with aluminum amalgam under nitrogen. (The aluminum amalgam is prepared by washing 20 mesh aluminum, 8.00 g, with diethyl ether, 170 ml, methanol, 340 ml, mercuric chloride, 8.03 g, in water, 275 ml, methanol, 170 ml, and diethyl ether, 170 ml).

The resulting black suspension is stirred for 1.75 hr during which the reaction temperature is permitted to go from 0° to 15° C. (slowly) then cooled to 0°, treated with ethyl acetate (210 ml) and stirred for an additional 30 min at 0° C. The suspension is filtered through diatomaeous earth and the filter cake washed with ethyl acetate. The combined filtrate is then washed with brine (300 ml), 0.5 M aqueous potassium bisulfate (300 ml), saturated aqueous sodium bicarbonate (300 ml) and brine (300 ml), dried, filtered, and concentrated to a yellow oil, crude formula CLXXII compound (6.03 g), 9-deoxy-9-methylene-3-oxa-1,2,3,4,5,6-pentanor-3,7- inter-m-phenylene-PGF₁, 3-(t-butyldimethylsilyl ether), 11,15-bis(tetrahydropyranyl ether). The crude product is combined with that from a repeat preparation to yield 10.1 g of formula CLXXII product which is chromatographed on silica gel eluting with 5% ethyl acetate in Skellysolve B (SSB, isomeric hexanes) to yield 6.93 g of 9-deoxy-9-methylene-3-oxa-1,2,4,5,6-pentanor-3,7-inter-m-phenylene-PGF₁, 3-(t-butyldimethylsilyl ether), 11,15-bis(tetrahydropyranyl ether). NMR absorptions are observed at 4.52–5.12 and 6.53–7.30$\delta$. Infrared absorptions are observed at 1600 and 1655 cm$^{-1}$. Silica gel TLC R$_f$ is 0.39 in 10% ethyl acetate in hexane.

B. A degassed solution of 9-deoxy-9-methylene-3-oxa-1,2,4,5,6-pentanor-3,7-inter-m-phenylene-PGF₁, 3-(t-butyldimethylsilyl ether), 11,15-bis(tetrahydropyranyl ether), the reaction product of Part A, (1.33 g) in dry tetrahydrofuran (70 ml) is cooled to 0° C. and treated under nitrogen with 0.5 M 9-borabicyclo[3.3.1]nonane (14 ml), dropwise over 5 min. The colorless solution is stirred for 4.5 hr at 0° and treated with 30% hydrogen peroxide (6 ml) followed by 3 N potassium hydroxide (6 ml). The resulting suspension is stirred for an additional 30 min at 0° C. and for 75 min while warming to room temperature. The reaction mixture is transferred to a separatory funnel, diluted with brine (300 ml) and ethyl acetate (300 ml). The layers are separated, and the aqueous layer extracted with ethyl acetate (600 ml). The organic extracts are washed with brine (6 ml), dried, filtered, and contrated to formula CLXXIII product, a colorless oil (3.3 g), 9-deoxy-9α-(hydroxymethyl)-3-oxa-1,2,4,5,6-pentanor-3,7-inter-m-phenylene-PGF₁, 3-(t-butyldimethylsilyl ether), 11,15-bis(tetrahydropyranyl ether). The crude formula CLXXIII product is chromatographed on silica gel (300 g) in 35% ethyl acetate in hexane to yield 1.26 g of 9-deoxy-9α-(hydroxymethyl)-3-oxa-1,2,4,5,6-pentanor-3,7-inter-m-phenylene-PGF₁, 3-(t-butyldimethylsilyl ether), 11,15-bis(tetrahydropyranyl ether) as a colorless oil. NMR absorptions are observed at 4.73, 5.12–5.70, 6.52–7.23$\delta$. Infrared absorptions are observed at 3480 and 1670 cm$^{-1}$. Silica gel TLC R$_f$ is 0.21 in 35% ethyl acetate in hexane.

C. A degassed solution of 9-deoxy-9α-hydroxymethyl-3-oxa-1,2,4,5,6-pentanor-3,7-inter-m-phenylene-PGF₁, 3-(t-butyldimethylsilyl ether), 11,15-bis(tetrahydropyranyl ether) (2.01 g), reaction product of Part B, in dry methylene chloride (45 ml) is cooled to $-5°$ C. under nitrogen and treated with triethylamine (0.72 ml), then with methanesulfonyl chloride (0.76 ml). The resulting solution is stirred at $-5°$ C. for 5 min then for 75 min while warming to ambient temperature. The reaction solution is poured over ice, and the resulting mixture swirled for a few minutes then transferred to a separatory funnel and partitioned between diethyl ether and brine. The layers are separated, and the aqueous layer extracted with ether (400 ml). The organic layer is washed with brine (200 ml) and saturated aqueous sodium bicarbonate (400 ml), dried, filtered, and conctrated to a formula CLXXIV product, a colorless oil (2.69 g), 9-deoxy-9α-mesyloxymethyl-3-oxa-1,2,4,5,6-pentanor-3,7-inter-m-phenylene-PGF₁, 3-(t-butyldimethylsilyl ether), 11,15-bis(tetrahydropyranyl ether). This product (2.69 g) is chromatographed on silica gel (185 g) eluting with 25% ethyl acetate in Skellysolve B to yield 1.99 g of 9-deoxy-9α-mesyloxymethyl-3-oxa-1,2,4,5,6-pentanor-3,7-inter-m-phenylene-PGF₁), 11,15-bis(tetrahydropyranyl ether). NMR absorptions are observed at 2.95, 4.70, 5.20–5.70, and 6.52–7.22$\delta$. Silica gel TLC R$_f$ is 0.30 in 35% ethyl acetate in hexane.

D. A degassed solution of 9-deoxy-9α-mesyloxymethyl-3-oxa-1,2,4,5,6-pentanor-3,7-inter-m-phenylene-PGF₁, 3-(t-butyldimethylsilyl ether), 11,15-bis(tetrahydropyranyl ether) (0.971 g), the reaction product of Part C, in dry tetrahydrofuran (35 ml) is cooled to 0° C. and treated under nitrogen with 0.75 M tetrabutylammonium fluoride (2.6 ml). The resulting amber solution is stirred for 2.5 hr at 0°–5° C. and is partitioned between ethyl acetate (150 ml) and brine (150 ml). The layers are separated, and the aqueous layer extracted with ethyl acetate (300 ml). The organic layer is then washed with 0.5 M aqueous ammonium chloride (150 ml), saturated aqueous sodium bicarbonate (300 ml) and brine (150 ml), dried, filtered and concentrated to give 0.82 g of formula CLXXV product, 9-deoxy-9α-mexyloxymethyl-3-oxa-1,2,4,5,6-pentanor-3,7-inter-m-phenylene-PGF₁, 11,15-bis(tetrahydropyranyl ether. Infrared absorptions are observed at 3330 cm$^{-1}$. Silica gel TLC R$_f$ is 0.37 in 50% ethyl acetate in hexane.

E. A degassed solution of 9-deoxy-9α-mesyloxymethyl-3-oxa-1,2,4,5,6-pentanor-3,7-inter-m-phenylene-PGF₁, 11,15-bis(tetrahydropyranyl ether) (0.82 g), reaction product of Part D, is cooled to $-40°$ C. under argon and treated with 57% sodium hydride (0.67 g). The resulting suspension is then stirred for 40 min at $-40°$ C. then 15 min at 0° C. The suspension is stirred for an additional 20 min while warming to room temperature and then stirred for 2.5 hr at reflux. The reaction is then cooled to 10° C., diluted with ice cold brine (200 ml) and extracted with ethyl acetate (450 ml). The ethyl acetate extracts are then washed with brine (300 ml), dried, filtered and concentrated to give 0.72 g of the formula CLXXVI crude product. The crude product is chromatographed in silica gel (175 g) in 25% ethyl acetate in Skellysolve B to yield 0.49 g of 9-deoxy-2',9α-methano-3-oxa-1,2,4,5,6-pentanor-3,7-(1',3'-inter-phenylene)-PGF₁, 11,15-bis(tetrahydropyranyl ether). NMR absorptions are observed at 4.77, 5.32–6.03, and 6.52–7.22$\delta$. Infrared absorptions are observed at 3340 and 1670 cm$^{-1}$. Silica gel TLC R$_f$ is 0.56 in 35% ethyl acetate in hexane.

F. A degassed solution of 9-deoxy-2',9α-methano-3-oxa-1,2,4,5,6-pentanor-3,7-(1',3'-inter-phenylene)-PGF₁, 11,15-bis(tetrahydropyranyl ether) (0.47 g), reaction product of Part E, in dry glyme (15 ml) is cooled to 0° C. and treated under nitrogen with methyl bromoacetate (0.26 ml) followed by 57% sodium hydride suspension (0.136 g). Following vigorous effervescence, a white precipitate is formed. The resulting suspension is stirred for 2.5 hr at 0°–5° C., diluted with ice cold brine (200 ml) and extracted with ethyl acetate (450 ml). The ethyl acetate extracts are washed with brine (300 ml), dried over magnesium sulfate, filtered and concentrated in a pale yellow oil (0.62 g), formula CLXXVII compound, 9-deoxy-2',9α-methano-3-oxa-4,5,6-trinor-3,7-(1',3'-interphenylene)-PGF₁, methyl ester, 11,15-bis(tetrahydropyranyl ether). Infrared absorptions are observed at 1765 and 1740 cm$^{-1}$.

G. A solution of 9-deoxy-2',9α-methano-3-oxa-4,5,6-trinor-3,7-(1',3'-inter-phenylene)-PGF₁, methyl ester, 11,15-bis(tetrahydropyranyl ether) (0.62 g), reaction product of Part F, in acetic acid (15 ml), water (7.5 ml) and tetrahydrofuran (5 ml) is reacted at 45° C. under nitrogen for 2.75 hr, cooled and diluted with ice cold brine (200 ml). The resulting suspension is extracted with ethyl acetate (400 ml), and the organic extracts washed with brine (400 ml), saturated aqueous sodium bicarbonate (600 ml) and brine (200 ml). The ethyl acetate extracts are then dried over magnesium sulfate, filtered and concentrated to give 0.44 g of pale yellow oil.

This crude product is chromatographed on silica gel (60 g) in 50% ethyl acetate in Skellysolve B to yield 0.37 g of product which was crystallized to yield 0.216 g of title product, 9-deoxy-2',9α-methano-3-oxa-4,5,6-trinor-3,7-(1',3'-inter-phenylene)-PGF$_1$, methyl ester. Melting range is 82°-84° C. NMR absorptions are observed at 3.77, 4.62, 5.42-5.63, and 6.53-7.25δ. Infrared absorptions are observed at 3520, 3400, and 1735 cm$^{-1}$. Silica gel TLC R$_f$ is 0.30 in 35% acetone in methylene chloride.

H. A solution of 9-deoxy-2'-9α-methano-3-oxa-4,5,6-trinor-3,7-(1',3'-inter-phenylene)-PGF$_1$, methyl ester (0.15 g), reaction product of Part G, in 5% potassium hydroxide in 9:1 methanol-water (5.5 ml) is stirred at 0° C. under nitrogen. The solution is turbid initially and a precipitate forms within 5 min. The reaction is then stirred for one hr at 0° C. diluted with ice cold brine (90 ml), acidified with 1 N hydrochloric acid, and extracted with ethyl acetate (180 ml). The ethyl acetate extract is then washed with brine (270 ml), dried over magnesium sulfate, and concentrated under reduced pressure to yield a waxy, semi-solid (0.131 g), which is crystallized to yield 0.105 g of title product, 9-deoxy-2',9α-methano-3-oxa-4,5,6-trinor-3,7-(1',3'-inter-phenylene)PGF$_1$. Melting range is 131°-133° C. NMR absorptions are observed at 4.68, 5.48-5.72, 6.68-7.22. Infrared absorptions are observed at 3460, 3280, 1735, 1720, and 1700 cm$^{-1}$.

I. The dosage at which the title compounds should be administered to achieve their effect, chiefly anti-platelet aggregation or blood pressure lowering, will vary according to the potency of the particular compound under study. When given orally, the compounds will show a desired effect in man at a dose from about 0.05 to about 50 mg/kg orally, preferably from about 0.1 to about 5 mg/kg. The compounds 9-deoxy-2',9α-methano-3-oxa-4,5,6-trinor-3,7-(1',3'-inter-phenylene)-PGF$_1$, methyl ester, given to a rat orally at a dose of 1 mg/kg lowered blood pressure 44 mmHg. After 52 min the blood pressure was still lower 14 mm. Intravenous dosages for the desired effect are from about 1 to about 500 ng/kg/min in man, preferably from about 10 to about 100 ng/kg/min.

EXAMPLE 32

9-Deoxy-2',9α-methano-3-oxa-4,5,6-trinor-3,7-(1',3'-inter-phenylene)-16,16-difluoro-PGF$_1$ (Formula XI: X$_1$ is —COOH, L$_1$ is α-fluoro:β-fluoro, R$_{20}$, R$_{20}$, R$_{21}$, R$_{23}$, and R$_{24}$ are all hydrogen, Z$_4$ is —CH$_2$—, R$_{22}$ is β-hydrogen, R$_8$, Y$_1$, M$_1$, and R$_7$ are as defined in Example 8) and its corresponding methyl ester (X$_1$ is —COOCH$_3$).

Refer to Chart P.

A. Diethyl ether (55 ml) tri-n-butylphosphine (2.28 g) and cuprous iodide (2.13 g) are combined with stirring with the resulting mixture being alternately degassed and flushed with nitrogen at 25° C. for 1 hr. The resulting solution is then cooled to —78° C. and is hereafter referred to as solution 32-I. Thereafter 60 ml of anhydrous diethyl ether and 6.47 g of m-bromo-phenol, t-butyldimethylsilyl ether are combined and the resulting solution alternately degassed and flushed with nitrogen and cooled to —78° C. After cooling, the resulting mixture is treated with 44.16 ml of a 1.02 M solution of t-butyllithium in n-pentane. This reaction mixture is then stirred at —78° C. for 1 hr and hereinafter referred to as solution 32-II. Solution 32-II is then transferred with stirring over 15 min to solution 32-I under a nitrogen atmosphere. The resulting solution changed in color from clear to yellow to an orange-brown to tan. The resulting mixture is then stirred at —78° C. for 30 min and labelled solution 32-III. Thereafter 4α-hydroxy-3β-(4',4'-difluoro-3'α-hydroxy-trans-1'-octenyl)-2-methylene-cyclopentanone, 4,3'-bis(tetrahydropyran-2-yl ether), 4 g, Example 25 of U.S. Pat. No. 4,181,798, and 38 ml of anhydrous dry ethyl ether are combined with stirring and the resulting mixture alternately degassed and flushed with nitrogen and thereafter cooled to —78° C. The resulting solution is referred to herein as solution 32-IV. Solution 32-IV is then added to solution 32-III with vigorous stirring over 25 min at —78° C. under a nitrogen atmosphere. The reaction mixture is then stirred at —78° C. for 30 min and thereafter transferred to 100 ml of 8% glacial acetic acid in diethyl ether (—40° C.) with vigorous stirring under a nitrogen atmosphere. The resulting mixture is then diluted with brine and extracted with diethyl ether. The ethereal extracts are then washed with aqueous sodium bicarbonate in brine, dried over sodium sulfate, concentrated under reduced pressure, and chromatographed on silica gel eluting with 20% ethyl acetate in Skellysolve B to yield 5.56 g of pure formula CLXXI compound: 16,16-difluoro-3-oxa-1,2,4,5,6-pentanor-3,7-inter-m-phenylene-PGE$_1$, 3-(t-butyldimethylsilyl ether), 11,15-bis(tetrahydropyran-2-yl ether). NMR absorptions (CDCl$_3$) are observed at 0.18, 3.1-5.0, 5.67, 6.52-6.88, and 6.88-7.2δ. Infrared absorptions are observed at 1745, 1600, 1585, 1490, 1275, 1260, 1200, 1155, 1125, 1075, 1035, 1025, 975, 840, and 780 cm$^{-1}$. Silica gel TLC R$_f$ is 0.36 and 0.41 in 25% ethyl acetate in Skellysolve B. Silica gel TLC R$_f$ is 0.5 in 5% acetone in methylene chloride.

B. Following the procedure of Example 31, Part A, 3.47 g of the reaction product of Part A of this example is converted to 2.98 g of formula CLXXII product as a colorless oil, 9-deoxy-9-methylene-3-oxa-1,2,4,5,6-pentanor-3,7-inter-m-phenylene-16,16-difluoro-PGF$_1$, 3-(t-butylsilyl ether), 11,15-bis(tetrahydropyranyl ether). NMR absorptions are observed at 0.17, 0.97, 1.0-3.2, 3.2-4.4, 4.4-5.0, 5.3-6.0, and 6.4-7.3δ. Infrared absorptions are observed at 1655, 1605, 1585, 1485, 1275, 1260, 1200, 1144, 1125, 1080, 1025, 970, 870, and 780 cm$^{-1}$. Silica gel TLC R$_f$ is 0.31 and at 0.36 in 10% ethyl acetate in hexane.

C. Following the procedure of Example 31, Part B, 2.83 g of the reaction product of Part B of this example is converted to 2.5 g of formula CLXXIII product as a colorless oil, 9-deoxy-9α-(hydroxymethyl)-3-oxa-1,2,4,5,6-pentanor-3,7-inter-m-phenylene-16,16-difluoro-PGF$_1$, 3-(t-butyldimethylsilyl ether), 11,15-bis(tetrahydropyranyl ether). NMR absorptions (CDCl$_3$) are observed at 0.18, 0.98, 1.15-3.0, 3.0-4.5, 4.5-5.0, 5.3-5.9, and 6.4-7.3δ. Infrared absorptions are observed at 3460, 1670, 1600, 1585, 1485, 1275, 1260, 1160, 1135, 1126, 1075, 1025, 975, 840, and 780 cm$^{-1}$. Silica gel TLC R$_f$ is 0.28 in 35% ethyl acetate in hexane.

D. Following the procedure of Example 31, Part C, the reaction product of Part C of this example (2.29 g) is converted to 1.83 g of formula CLXXIV product as a colorless oil, 9-deoxy-9α-mesyloxymethyl-3-oxa- 1,2,4,5,6-pentanor-3,7-inter-m-phenylene-16,16-difluoro-PGF$_1$, 3-(t-butyldimethylsilyl ether), 11,15-bis(tetrahydropyranyl ether). NMR absorptions are observed at 0.18, 0.98, 1.15–2.85, 2.95, 311–4.5, 4.5–5.0, 5.2–5.9, and 6.5–7.4$\delta$. Infrared absorptions are observed at 2930, 2860, 1605, 1590, 1490, 1465, 1440, 1360, 1275, 1200, 1175, 1120, 1025, 975, and 840 cm$^{-1}$. Silica gel TLC R$_f$ is 0.28 in 30% ethyl acetate and hexane.

E. Following the procedure of Example 31, Part D, 1.7 g of the reaction product of Part D of this example is converted to 1.6 g of formula CLXXV product as a yellow oil, 9-deoxy-9$\alpha$-mesyloxymethyl-3-oxa-1,2,4,5,6-pentanor-3,7-inter-m-phenylene-16,16-difluoro-PGF$_1$, 11,15-bis(tetrahydropyranyl ether). Silica gel TLC R$_f$ is 0.34 in ethyl acetate and hexane (1:1).

F. Following the procedure of Example 31, Part E, 1.52 g of the reaction product of Part D of this example is converted to 0.83 g of formula CLXXVI product as a white foam, 9-deoxy-2',9$\alpha$-methano-3-oxa-1,2,4,5,6-pentanor-3,7-(1',3'-inter-phenylene)-16,16-difluoro-PGF$_1$, 11,15-bis(tetrahydropyranyl ether). NMR absorptions are observed at 0.95, 1.05–2.95, 3.5–5.0, 5.3–6.0, and 6.5–7.2$\delta$. Infrared absorptions are observed at 3350, 2930, 1670, 1615, 1590, 1465, 1280, 1200, 1120, 1070, and 975 cm$^{-1}$. The mass spectrum exhibits peaks at 534, 451, 446, 402, and 348. Silica gel TLC R$_f$ is 0.26 in ethyl acetate and hexane (1:3) and 0.40 in acetone and methylene chloride (1:19).

G. Following the procedure of Example 31, Part F, 0.80 g of the reaction product of Part F of this example is converted to 1.06 g of formula CLXXVII product as a colorless oil, 9-deoxy-2',9$\alpha$-methano-3-oxo-4,5,6-trinor-3,7-(1',3'-inter-phenylene)-16,16-difluoro-PGF$_1$, methyl ester, 11,15-bis(tetrahydropyranyl ether). Silica gel TLC R$_f$ is 0.44 in 5% acetone and methylene chloride.

H. Following the procedure of Example 31, Part G, 1.0 g of the reaction product of Part G of this example is converted to 0.62 g of crystalline methyl ester title product, a Formula CLXXVIII white solid. Recrystallization from hexane in diethyl ether yields a material with melting range 93°–95° C. NMR absorptions are observed at 0.95, 1.10–2.90, 2.90–4.8, 5.4–5.8, and 6.4–7.3. Infrared absorptions are observed at 3560, 3400, 1765, 1750, 1735, 1720, 1675, 1605, 1585, 1270, 1215, 1205, 1120, 1105, 1080, 1010, 970, and 770 cm$^{-1}$. The mass spectrum for the bis-trimethylsilyl derivative exhibits a high resolution peak at 582.2997. Silica gel TLC R$_f$ is 0.35 in hexane and ethyl acetate (1:4).

Following the procedure of Example 31, Part H, the reaction product of Part H of this example (0.25 g) is converted to the carboxylic acid title product (158 mg) as a crystalline solid. Melting range is 128°–130° C. NMR absorptions (COCD$_3$) are observed at 0.9, 1.3–3.0, 3.0–4.6, 4.68, 4.8–5.5, 6.5–6.9, 5.5–5.9, and 6.6–7.3$\delta$. Infrared absorptions are observed at 3570, 3480, 3370, 3220, 2800, 1740, 1720, 1605, 1585, 1235, 1210, 1125, 1105, 1080, 1000, and 970 cm$^{-1}$. The mass spectrum for the tris-trimethylsilyl derivative exhibits a high resolution peak at 640.3232. Silica gel TLC R$_f$ is 0.18 in the A-IX solvent system.

Following the procedure of Examples 31 and 32, there are prepared each of the various formula CLXXVIII products in free acid or ester form from corresponding formula CLXXI reactants.

Formula CLXXVIII compounds wherein Y$_1$ is unsaturated (trans- or cis—CH=CH—) are transformed to corresponding formula CLXXVIII compounds wherein Y is saturated (—CH$_2$CH$_2$—) by hydrogenation, as exemplified below:

EXAMPLE 33

9-Deoxy-2',9$\alpha$-methano-3-oxa-4,5,6-trinor-3,7-(1',3'-inter-phenylene)-13,14-dihydro-PGF$_1$ (Formula XI: X$_1$ is COOH, Y$_1$ is —CH$_2$CH$_2$—, R$_{20}$, R$_{21}$, R$_{23}$, and R$_{24}$ are all hydrogen, Z$_4$ is —CH$_2$—, R$_{22}$ is $\beta$-hydrogen, R$_8$, M$_1$, L$_1$, and R$_7$ are as defined in Example 8) and its corresponding methyl ester (X$_1$ is —COOCH$_3$)

A. A solution of the methyl ester title product of Example 31 (0.341 g) in ethyl acetate (35 ml) is treated at ambient temperature with 5% palladium-on-charcoal and hydrogenated at atmospheric pressure. The resulting suspension is then stirred for 70 minutes with a hydrogen uptake of 20 ml (atmospheric pressure). The resulting suspension is then filtered through diatomaceous earth and the filter cake washed with ethyl acetate. The combined filtrate is then concentrated under reduced pressure to yield a colorless oil which is chromatographed on silica gel eluting with ethyl acetate in Skellysolve B to yield 0.306 g of title product (methyl ester), a colorless oil. NMR absorptions (CDCl$_3$) are observed at 0.9, 0. 1.07–1.23, 3.3–4.03, 3.77, 4.62, 6.52, and 7.27$\delta$. Infrared absorptions are observed at 3350, 2930, 2855, 1760, 1740, 1605, 1585, 1467, 1435, 1275, 1205, 1120, 1080, 1025, and 775 cm$^{-1}$. Silica gel TLC R$_f$ is 0.54 in ethyl acetate.

B. Following the procedure of Example 31, Part H, the title product of Part A of this example (0.177 g) is converted to 0.23 g of title product (free acid) as a solid. Recrystallization from ethyl acetate in hexane yields 0.096 g with melting range 121°–123° C. The mass spectrum for the tris-trimethylsilyl derivatives exhibits a high resolution peak at 606.3553 and other peaks at 591–535, 516, 427, 426, 275, 274, 173, and 157. Silica gel TLC R$_f$ is 0.27 in A-IX.

EXAMPLE 34

9-Deoxy-2',9$\beta$-methano-3-oxa-4,5,6-trinor-3,7-(1',3'-inter-phenylene)-PGF$_1$ (Formula XI: X$_1$ is COOH, R$_{20}$, R$_{21}$, R$_{22}$, and R$_{24}$ are all hydrogen, Z$_4$ is —CH$_2$—, R$_{22}$ is $\alpha$-hydrogen, R$_8$, Y$_1$, M$_1$, L$_1$, and R$_7$ are as defined in Example 8) and its corresponding methyl ester (X$_1$ is —COOCH$_3$)

Refer to Charts Q and R.

A. A solution of 0.82 g of the reaction product of Example 31, Part B, in 16 ml of methylene chloride is stirred at ambient temperature under nitrogen atmosphere and treated with diatomaceous earth followed by 26 ml of Collins reagent (prepared from 2.5 ml of pyridine and 1.55 g of chromium trioxide in 50 ml of methylene chloride). The resulting suspension is then stirred for 35 min at ambient temperature under a nitrogen atmosphere and filtered through 30 g of silica gel, eluting with 150 ml of ethyl acetate. Concentration under reduced pressure yields 0.90 g of a pale yellow oil. Chromatographing on 85 g of silica gel eluting with 20% ethyl acetate in Skellysolve B yields 0.644 g of pure formula CLXXXII aldehyde as a colorless oil, 9-deoxo-9$\alpha$-formyl-3-oxa-1,2,4,5,6-pentanor-3,7-inter-m-phenylene-PGE$_1$, 1-(t-butyldimethylsilyl ether), 11,15-bis(tetrahydropyranyl ether). NMR absorptions are observed at 0.18, 0.88, 0.98, 1.13–3.08, 3.23–4.35, 4.73, 5.25–5.75, 6.57–7.37, and 9.88$\delta$. Infrared absorptions are observed at 2730, 1720, 1600, 1585, 1485, 1275, 1260, 1075, 1035, 1030, 1020, 975, and 840 cm$^{-1}$. Silica gel TLC $R_f$ is 0.47 in ethyl acetate and hexane (1:3).

B. A degassed solution of 1.5 g of the reaction product of Part A and 0.36 ml of 1,8-diazobicyclo[5.4.0]undec-7-ene in 150 ml of methylene chloride is stirred for 40 hr at ambient temperature under a nitrogen atmosphere, washed with 100 ml of ice cold 0.15 M aqueous potassium bisulfate, 100 ml of saturated aqueous sodium carbonate, and 100 ml of brine, dried over anhydrous sodium sulfate and concentrated under reduced pressure to yield 1.5 g of formula CXCII product as a yellow oil, 9-deoxy-9$\beta$-formyl-3-oxa-1,2,4,5,6-pentanor-3,7-inter-phenylene-PGF$_1$, 3-(t-butyldimethylsilyl ether), 11,15-bis(tetrahydropyranyl ether). NMR absorptions (CDCl$_3$) are observed at 0.18, 0.89, 0.98, 1.1–3.2, 3.2–4.4, 4.68, 5.2–5.8, 6.58–7.4, and 9.22$\delta$. Infrared absorptions are observed at 1725, 1600, 1585, 1485, 1440, 1275, 1260, 1200, 1160, 1130, 1075, 1035, 1020, 975, 870, and 840 cm$^{-1}$. Silica gel TLC $R_f$ is 0.24 in ethyl acetate and hexane (1:3).

C. A solution of 1.5 g of the reaction product of Part B in 40 ml of methanol is treated with stirring at 20° C. under a nitrogen atmosphere over several minutes with 400 mg of sodium borohydride, stirred for 20 min at 20° C. The resulting mixture is then added to a cold solution of 200 ml of brine and 32 ml of 0.1 M aqueous potassium sulfate, extracted with 600 ml of ethyl acetate, washed with 200 ml of saturated aqueous sodium bicarbonate in 200 ml of brine, dried over anhydrous magnesium sulfate, concentrated under reduced pressure, and chromatographed on 200 g of silica gel eluting with 35% ethyl acetate in hexane to yield 1.37 g of formula CLCIII product as a colorless oil, 9-deoxy-9$\beta$-hydroxymethyl-3-oxa-1,2,4,5,6-pentanor-3,7-inter-m-phenylene-PGF$_1$, 3-(t-butyldimethylsilyl ether), 11,15-(tetrahydropyranyl ether). NMR absorptions (CDCl$_3$) are observed at 0.17, 0.88, 0.99, 1.1–3.0, 3.0–4.35, 4.7, 5.25–5.85, and 6.5–7.4$\delta$. Infrared absorptions are observed at 3460, 1665, 1605, 1685, 1490, 1275, 1260, 1200, 1160, 1135, 1115, 1075, 1120, 1005, 975, 840, and 780 cm$^{-1}$. Silica gel TLC $R_f$ is 0.20 in 35% ethyl acetate in hexane.

D. A degassed solution of 1.32 g of the reaction product of Part B in 0.47 ml of triethyl amine and 30 ml of methylene chloride at 20° C. under a nitrogen atmosphere is treated with 0.5 ml of methanesulfonyl chloride, stirred for 5 min at 0° C., warmed to 20° C. over 90 min, added to 50 g of ice, diluted with 150 ml of brine, extracted with 450 ml of diethyl ether, washed with 150 ml of brine and 300 ml of saturated aqueous sodium bicarbonate, dried over anhydrous magnesium sulfate, concentrated under reduced pressure to yield an oil, and filtered through 70 g of silica gel eluting with 30% ethyl acetate in hexane to yield 1.47 g of mesylate corresponding to the starting material, i.e., the 9$\beta$ analog of formula CLXXIV. Silica gel TLC $R_f$ is 0.23 in 30% ethyl acetate in hexane.

E. A degassed solution of 1.47 g of the reaction product of Part D and 50 ml of dry tetrahydrofuran at 0° C. under a nitrogen atmosphere is treated with 3.9 ml of 0.45 M tetra-n-butylammonium fluoride. The resulting solution is then stirred at 0° C. for 4 hr, treated with another 0.5 ml of tetra-n-butylammonium fluoride, stirred for 30 min at 0° C., diluted with 150 ml of brine, extracted with 450 ml of ethyl acetate, washed successively with 150 ml of 0.5 M aqueous ammonium chloride, 300 ml of saturated aqueous sodium bicarbonate, and 150 ml of brine, dried over anhydrous sodium sulfate, and concentrated under reduced pressure to yield 1.3 g of a yellow oil, the phenol corresponding to the starting material, i.e., the 9$\beta$ isomer of the formula CLXXV compound. Silica gel TLC $R_f$ is 0.11 in 35% ethyl acetate in hexane.

F. A degassed solution of 1.3 g of the reaction product of Part E in 75 ml of dry glyme at $-40°$ C. under a nitrogen atmosphere is treated with 90 mg of 57% sodium hydride dispersion in mineral oil, stirred at $-40°$ to $-30°$ C. for 40 min, stirred at 0° C. for 15 min, stirred at ambient temperature for 15 min, heated and refluxed for 5 hr, cooled to ambient temperature, added to 200 ml of ice cold glyme, extracted with 450 ml of ethyl acetate, washed with 300 ml of brine, dried over anhydrous on 175 g of silica gel eluting with 25% ethyl acetate in hexane to yield 0.61 g of the 9$\beta$ isomer corresponding to the formula CLXXVI compound as a viscous oil. NMR absorptions are observed at 0.90, 1.07–3.1, 3.1–4.4, 4.75, 5.33–6.16, and 6.5–7.2$\delta$. Infrared absorptions are observed at 3340, 1665, 1610, 1585, 1500, 1465, 1135, 1110, 1075, 1020, and 980 cm$^{-1}$. Silica gel TLC $R_f$ is 0.26 in 25% ethyl acetate in hexane and 0.23 in 5% acetone in methylene chloride.

G. A solution of 0.50 g of the reaction product of Part F in 28 ml of methyl bromoacetate in 16 ml of dry glyme at 0° C. under an argon atmosphere is treated with 0.14 g of a 57% mineral oil dispersion of sodium hydride. The resulting suspension is then stirred for 2.5 hr at 0° C., quenched with 200 ml of cold brine, extracted with 460 ml of ethyl acetate, washed with 300 ml of brine, dried over anhydrous sodium sulfate, and concentrated under reduced pressure to yield 0.68 g of an oil, the 9$\beta$ isomer corresponding to the formula CLXXVII compound.

H. A solution of the reaction product of Part G (0.68 g) in 5 ml of tetrahydrofuran, 7.5 ml of water, and 15 ml of acetic acid is heated for 2.5 hr at 45° C., cooled, diluted with 200 ml of brine, extracted with 400 ml of ethyl acetate, washed with 400 ml of brine, washed with 200 ml of saturated aqueous sodium bicarbonate, and 200 ml of brine, dried over anhydrous sodium sulfate, concentrated under reduced pressure to yield an oil, chromatographed on 75 g of silica gel eluting with 30% hexane in ethyl acetate to 100% ethyl acetate to yield 0.32 g of title methyl ester as a white foam. Crystallization from hot diethyl ether in hexane yields 0.23 g of pure ester product as a white solid. Melting range is 85°–87° C. NMR absorptions (CDCl$_3$) are observed at 0.90, 1.07–2.9, 2.9–4.5, 4.61, 5.4–5.8. and 6.38–7.34$\delta$. Infrared absorptions are observed at 3520, 3420, 1735, 1720, 1605, 1580, 1300, 1240, 1210, 1110, 1085, 1050, 1010, 970, 760, 720, and 710 cm$^{-1}$. The mass spectrum of the bis-trimethylsilyl derivative exhibits a high resolution peak at 546.3182. Silica gel TLC $R_f$ is 0.14 in 30% ethyl acetate in hexane.

I. Following the procedure of Example 31, Part H, the title product of Part H (158 mg) is transformed to the title free acid (129 mg) as a white solid. Melting range is 150°–154° C. NMR absorptions are observed at 0.90, 1.07–3.5, 3.85–4.35, 4.70, 5.09–5.9, and 6.5–7.3$\delta$. Infrared absorptions are observed at 3380, 2640, 2560, 1730, 1605, 1580, 1260, 1230, 1115, 1050, 1025, 970, and 770 cm$^{-1}$.

Following the procedure of Example 34, each of the various formula XI compounds are prepared wherein R$_{22}$ is $\alpha$-hydrogen. Further following the procedure of Example 33, the various 9$\beta$-methano isomers of Example 34 and corresponding formula XI compounds wherein $Y_1$ is cis- or trans—CH=CH— are hydrogenated to corresponding 13,14-dihydro-PGF$_1$ compounds.

EXAMPLE 35

9-Deoxo-2′,9′-metheno-3-oxa-4,5,6-trinor-3,7-(1′,3′-inter-phenylene)-PGE$_1$ (Formula XI: $X_1$ is COOH, $R_{20}$, $R_{21}$, $R_{23}$, and $R_{24}$ are all hydrogen, $Z_4$ is —CH$_2$—, $R_{21}$ and $R_{22}$ taken together form a valence bond, $R_8$, $Y_1$, $M_1$, $L_1$, and $R_7$ are as defined in Example 8) and its corresponding methyl ester ($X_1$ is —COOCH$_3$)

Refer to Chart T.

A. A degassed solution of the reaction product of Example 34, Part A, (1.68 g) in dry tetrahydrofuran (50 ml) is cooled to 0° C. and treated under a nitrogen atmosphere with 0.75 M tetrabutylammonium fluoride (4.37 ml). The resulting solution is then stirred at 0° C. for 2 hr, diluted with brine (300 ml), extracted with ethyl acetate, washed with brine, dried over magnesium sulfate, filtered, and concentrated under reduced pressure to yield 2.3 g of an oil. The oil is chromatographed on silica gel (160 g) in 25% ethyl acetate in Skellysolve B yielding 1.21 g of formula CCXI compound, 9-deoxo-9α-formyl-1,2,4.5,6-pentanor-3,7-inter-m-phenylene-PGE$_1$, 11,15-bis(tetrahydropyranyl ether). NMR absorptions (CDCl$_3$) are observed at 0.88, 1.13–3.15, 3.27–4.47, 4.71, 6.10, 6.53–7.41, 9.27δ. Infrared absorptions are observed at 3345, 2930, 2860, 2720, 1735, 1715, 1605, 1595, 1585, 1485, 1450, 1370, 1350, 1255, 1235, and 970 cm$^{-1}$. Silica gel TLC R$_f$ is 0.12 in 25% ethyl acetate and hexane and 0.39 in 50% ethyl acetate in hexane.

B. A degassed solution of 0.28 g of the reaction product of Part A in 33 ml of glyme is cooled to −40° C. under argon and treated with 2.95 N methylmagnesium chloride in tetrahydrofuran (0.2 ml). The reaction mixture is stirred at −40° C. for 15 min, stirred at 0° C. for 15 min, permitted to warm to ambient temperature, stirred at reflux for 115 hr under an argon atmosphere, cooled, diluted with ice cold brine (150 ml), extracted with ethyl acetate (300 ml), washed with brine (300 ml), dried over magnesium sulfate, filtered, concentrated under reduced pressure to yield 0.31 g of an oil, and chromatographed on silica gel eluting with 25% ethyl acetate in Skellysolve B to yield 0.16 g of the formula CCXII compound, 9-deoxo-2′,9-metheno-3-oxa-1,2,4,5,6-pentanor-3,7-(1′,3′-inter-phenylene)-PGE$_1$, 11,15-bis(tetrahydropyranyl ether). The mass spectrum of the trimethylsilyl derivative exhibits a molecular peak at 568 and other peaks at 466, 382, 364, 314, 297, 267, 255, 243, 230, 270, 153, and 85. Silica gel TLC R$_f$ is 0.25 in 25% ethyl acetate in hexane and 0.58 in 50% ethyl acetate in hexane.

C. A degassed solution of the reaction product of Part C (0.16 g) in dry glyme (5 ml) is cooled at −5° C. and treated with methylbromo acetate (0.04 ml) under a nitrogen atmosphere. The resulting solution is then treated with 50% sodium hydride dispersion in mineral oil (0.16 g). Precipitate forms in 5 min in the resulting suspension is stirred for 1.5 hr at 0° C., diluted with brine (100 ml), extracted with ethyl acetate (240 ml), washed with brine (100 ml), dried over magnesium sulfate, filtered, concentrated to yield a brown residue which solidifies on refrigeration, and chromatographed on 25 g of silica gel eluting with 20% ethyl acetate in Skellysolve B to yield 0.136 g of the bis(tetrahydropyranyl ether) of a formula CCXIII compound: 9-deoxo-2′,9-metheno-3-oxa-4,5,6-trinor-3,7-(1,3-inter-phenylene)-PGF$_1$, methyl ester, 11,15-bis(tetrahydropyranyl ether). Melting range is 81°–83° C. The mass spectrum exhibits peaks at 366, 384, 364, 279, 247, 230, 215, 149, and 85. Silica gel TLC R$_f$ is 0.45 in 5% acetone in methylene chloride.

D. A solution of the reaction product of Part C (0.12 g) in tetrahydrofuran (1 ml), water (2 ml) and acetic acid (4 ml) is heated at 45° C. under a nitrogen atmosphere for 2.25 hr, cooled, and partitioned between brine (100 ml) in ethyl acetate (90 ml). The layers are separated and the aqueous layer extracted with ethyl acetate (160 ml). The organic layers are then washed successively with brine (100 ml), water (100 ml), saturated aqueous sodium bicarbonate (300 ml) and brine (200 ml), dried over magnesium sulfate, filtered, concentrated to yield 0.97 g of a solid, and chromatographed on 30 g of silica gel, eluting with 85% ethyl acetate in hexane to yield 0.083 g of white crystalline formula CCXIII title product in methyl ester form. Recrystallization from diethyl ether in hexane yields 0.056 g of pure methyl ester title product. Melting range is 96°–98° C. NMR absorptions (CDCl$_3$) are observed at 0.94, 3.86, 3.92–4.28, 4.72, 5.58–5.86, and 6.62–7.18δ. Infrared absorptions are observed at 3420, 1765, 1665, 1600, 1575, 1465, 1440, 1275, 1215, 1190, 1105, 1085, 970, and 770 cm$^{-1}$. The mass spectrum for the trimethylsilyl derivative exhibits a molecular ion at 554 and other peaks at 454, 383, 365, 364, 230, 229, 225. Silica gel TLC R$_f$ is 0.41 in ethyl acetate.

E. Following the procedure of Example 31, Part H, the reaction product of Part D (0.19 g) is converted to 76 mg of crystalline title product in free acid form. Melting range is 150°–152° C. NMR absorptions (CDCl$_3$) are observed at 0.91, 1.2–3.48, 3.88–4.15, 4.70, 5.62–4.66, and 6.63–7.11. The mass spectrum for the trimethylsilyl derivative exhibits a high resolution peak at 602.3251 and other peaks at 512, 422, 287, 225, 174, and 173. Silica gel TLC R$_f$ is 0.23 in the A-IX solvent system.

EXAMPLE 36

9-Deoxy-2′,9α-methano-3-oxa-4,5,6,13,14,15,16,17,18,19,20-undecanor-3,7-(1′,3′-inter-phenylene)-12-formyl-PGF$_1$, methyl ester (formula CCXXII: $X_1$ is —COOCH$_3$, $Z_4$ is —CH$_2$—, $R_{20}$, $R_{21}$, and $R_{23}$ are hydrogen, $R_{22}$ is β-hydrogen, and $R_{18}$ is tetrahydropyran-2-yl-oxy)

Refer to Chart U.

Ozone is bubbled through a solution of 0.72 g of the reaction product of Example 31, Part F, in 50 ml of absolute methanol at −78° C. for 5 min. Thereafter oxygen is bubbled through the resulting solution for 5 min and the solution is treated with 16 ml of dimethyl sulfide. After standing at 0° C. for 16 hr under a nitrogen atmosphere and 2½ hr at ambient temperature, the solution is diluted with 200 ml of ethyl acetate, washed successively with 100 ml of brine, 100 ml of saturated aqueous sodium bicarbonate and 100 ml of brine, dried over anhydrous sodium sulfate, concentrated under reduced pressure, and chromatographed on 175 g of silica gel eluting with 35% ethyl acetate in hexane to yield 367 mg of title product as a colorless oil. NMR absorptions (CDCl$_3$) are observed at 1.0–3.0, 3.1–4.5, 3.63, 6.45–7.34, and 9.77δ. The mass spectrum exhibits peaks at 388 and 304. Silica gel TLC R$_f$ is 0.19 and 0.22 in 25% and 30% ethyl acetate in hexane.

EXAMPLE 37

9-Deoxy-2′,9α-methano-20-methyl-3-oxa-4,5,6-trinor-3,7-(1′,3′-inter-phenylene)-PGF$_1$ (Formula XI: $X_1$, $Z_4$, $R_8$, $R_{20}$, $R_{21}$, $R_{22}$, $R_{23}$, $R_{24}$, $Y_1$, $M_1$, and $L_1$ are as defined in Example 31 and $R_7$ is n-pentyl) its methyl ester ($Z_1$ is —COOCH$_3$), its 15-epimer ($M_1$ is α-H:β-OH), and 15-epimer methyl ester ($M_1$ is α-H:β-OH and $Z_1$ is —COOCH$_3$)

Refer to Chart U.

A. A suspension of 56 mg of a 57% sodium hydride dispersion in mineral oil and 4 ml of tetrahydrofuran at 0° C. under a nitrogen atomsphere is treated with a solution of 286 mg of dimethyl 2-oxooctylphosphonate in 4 ml of tetrahydrofuran, stirred for 5 min at 0° C., stirred for 1 hr at ambient temperature, cooled to 0° C., treated with a solution of 0.39 g of title product of Example 36 and 4 ml of tetrahydrofuran, stirred for 2½ hr at ambient temperature, cooled at 0° C., added to a solution of 40 ml of ethyl acetate containing several drops of acetic acid), extracted with 120 ml of ethyl acetate, washed with 30 ml of saturated aqueous sodium bicarbonate, washed with 30 ml of brine, dried over anhydrous sodium sulfate, concentrated under reduced pressure to yield an oil, and chromatographed on 60 g of silica gel eluting with 25% ethyl acetate in hexane to yield 0.42 g of a colorless oil, 9,15-dideoxy-15-keto-2′,9α-methano-20-methyl-4,5,6-trinor-3,7-(1′,3′-inter-phenylene)-PGF$_1$, methyl ester, 11-tetrahydropyranyl ether. NMR absorptions are observed at 0.89, 1.05–3.0, 3.5–4.37, 4.62, and 5.97–7.30δ. The mass spectrum exhibits peaks at 414, 396, 323, 311, and 301. Silica gel TLC R$_f$ is 0.26 in 25% ethyl acetate in hexane.

B. A degassed solution of 42 mg of sodium borohydride and 4 ml of absolute methanol at −30° C. under a nitrogen atmosphere is treated dropwise with a solution of 391 mg of the title reaction product of Part A in 0.3 ml of methylene chloride and 3 ml of methanol, stirred for 1½ hr at −30° C., quenched by careful addition of 0.2 ml of glacial acetic acid, diluted with 70 ml of brine, extracted with 210 ml of ethyl acetate, washed with 70 ml of saturated aqueous sodium bicarbonate, washed with 70 ml of brine, dried over anhydrous sodium sulfate, concentrated under reduced pressure to yield 0.42 g of a colorless oil, and chromatographed on 60 g of silica gel eluting with 40% ethyl acetate in hexane to yield 0.36 g of an epimeric mixture of C-15 alcohols. Silica gel TLC R$_f$ is 0.20 in 40% ethyl acetate in hexane.

C . A solution of the reaction products of Part B above in 3 ml of tetrahydrofuran, 4.5 ml of water, and 9 ml of acetic acid is heated to 45° C. under a nitrogen atmosphere for 2.5 hrs, cooled, diluted washed with 100 ml of brine, extracted with 200 ml of ethyl acetate, washed with 100 ml of brine, washed with 300 ml of saturated aqueous sodium bicarbonate and 100 ml of brine, dried over anhydrous sodium sulfate, concentrated under reduced pressure to a yellow oil, and chromatographed on 60 g of silica gel eluting with 20% ethyl acetate in methylene chloride to yield 96 mg of 9-deoxy-2′,9α-methano-20-methyl-3-oxa-4,5,6-trinor-3,7-(1,3-inter-phenylene)-15-epi-PGF$_1$, methyl ester as a colorless oil and 159 mg of 9-deoxy-2′,9α-methano-20-methyl-3-oxa-4,5,6-trinor-3,7-(1,3-inter-phenylene)-PGF$_1$, methyl ester as a white solid. Recrystallization of the 15α-hydroxy compound from hot hexane in diethyl ether yields 140 mg as a white solid. Melting range is 79°–82° C. For the title product methyl ester, NMR absorptions are observed at 0.92, 1.08–3.0, 3.38–4.5, 4.64, 5.33–5.70, and 6.5–7.4. The mass spectrum of the trimethylsilyl derivative exhibits a high resolution peak at 560.3375. Silica gel TLC R$_f$ is 0.19 in 20% ethyl acetate in methylene chloride and 0.31 in 20% hexane in ethyl acetate. For the 15-epi compound, NMR absorptions (CDCl$^3$) are observed at 0.89, 1.07–3.0, 3.7–4.33, 4.63, 5.5–5.8, and 6.55–7.37δ. Infrared absorptions are observed at 3360, 1765, 1750, 1735, 1605, 1585, 1470, 1440, 1205, 1120, 1080, 970, and 770 cm$^{-1}$. The mass spectrum for the trimethylsilyl derivative exhibits a high resolution peak at 560.3385. Silica gel TLC R$_f$ is 0.35 in 20% acetone and methylene chloride and 0.45 in 20% hexane and ethyl acetate.

D. Following the procedure of Example 31, Part H, the 15α-hydroxy title product of Part C (94 mg) is transformed to 9-deoxy-2′,9α-methano-20-methyl-3-oxa-4,5,6-trinor-3,7-(1,3-inter-phenylene)-PGE$_1$, title free acid, as a white solid, 81 mg. Melting range is 144°–146° C. NMR absorptions (CD$_3$COCD$_3$) are observed at 0.8, 1.05–2.9, 3.2–4.5, 4.65, 5.38–5.56, and 6.6–7.2δ. The mass spectrum of the trimethylsilyl derivative exhibits a high resolution peak at 618.3576. Silica gel TLC R$_f$ is 0.14 in the A-IX solvent system.

E. Further following the procedure of Example 31, Part H, the 15-epi title product of Part C (93 mg) is converted to 9-deoxy-2′,9α-methano-20-methyl-3-oxa-4,5,6-trinor-3,7-(1,3-inter-phenylene)-15-epi-PGF$_1$, a white solid, 72 mg. Melting range is 105°–108° C. MMR absorptions (CD$_3$COCD$_3$) are observed at 0.90, 1.05–2.9, 3.2–4.3, 4.71, 5.0–5.84, and 6.5–7.34δ. Silica gel TLC R$_f$ is 0.19 in the A-IX solvent system.

Following the procedures of Examples 36 and 37, there are substituted C-12 side chains according to the procedure of Chart U for each of the various formula XI compounds.

Thus, according to procedures described above, there are prepared (5E)-9β-methyl-CBA$_2$ compounds,
(5Z)-9β-methyl-CBA$_2$ compounds,
(5E)-5-fluoro-9β-methyl-CBA$_2$ compounds,
(5Z)-5-fluoro-9β-methyl-CBA$_2$ compounds,
(5E)-5-fluoro-CBA$_2$ compounds,
(5Z)-5-fluoro-CBA$_2$ compounds,
(5E)-9β-methyl-2,5-inter-o-phenylene-3,4-dinor-CBA$_2$ compounds,
(5Z)-9β-methyl-2,5-inter-o-phenylene-3,4-dinor-CBA$_2$ compounds,
(5E)-9β-methyl-1,5-inter-o-phenylene-2,3,4-trinor-CBA$_2$ compounds,
(5E)-9β-methyl-1,5-inter-o-phenylene-3,4,5-trinor-CBA$_2$ compounds,
(5E)-2,5-inter-o-phenylene-3,4-dinor-CBA$_2$ compounds,
(5Z)-2,5-inter-o-phenylene-3,4-dinor-CBA$_2$ compounds,
(5E)-1,5-inter-m-phenylene-2,3,4-trinor-CBA$_2$ compounds,
(5Z)-1,5-inter-m-phenylene-2,3,4-trinor-CBA$_2$ compounds,
2,2-difluoro-(5E)-9β-methyl-CBA$_2$ compounds,
2,2-difluoro-(5Z)-9β-methyl-CBA$_2$ compounds,
2,2,5-trifluoro-(5E)-9β-methyl-CBA$_2$ compounds,
2,2,5-trifluoro-(5Z)-9β-methyl-CBA$_2$ compounds,
2,2,5-trifluoro-(5E)-CBA$_2$ compounds,
2,2,5-trifluoro-(5Z)-CBA$_2$ compounds,
2,2-difluoro-(5E)-9β-methyl-2,5-inter-o-phenylene-3,4-dinor-CBA$_2$ compounds, 2,2-difluoro-(5Z)-9β-methyl-2,5-inter-o-phenylene-3,4-dinor-CBA₂ compounds,
2,2-difluoro-(5E)-9β-methyl-1,5-inter-o-phenylene-2,3,4-trinor-CBA₂ compounds,
2,2-difluoro-(5E)-9β-methyl-1,5-inter-o-phenylene-3,4,5-trinor-CBA₂ compounds,
2,2-difluoro-(5E)-2,5-inter-o-phenylene-3,4-dinor-CBA₂ compounds,
2,2-difluoro-(5Z)-2,5-inter-o-phenylene-3,4-dinor-CBA₂ compounds,
2,2-difluoro-(5E)-1,5-inter-m-phenylene-2,3,4-trinor-CBA₂ compounds,
2,2-difluoro-(5Z)-1,5-inter-m-phenylene-2,3,4-trinor-CBA₂ compounds,
trans-2,3-didehydro-(5E)-9β-methyl-CBA₂ compounds,
trans-2,3-didehydro-(5Z)-9β-methyl-CBA₂ compounds,
trans-2,3-didehydro-(5E)-5-fluoro-9β-methyl-CBA₂ compounds,
trans-2,3-didehydro-(5Z)-5-fluoro-9β-methyl-CBA₂ compounds,
trans-2,3-didehydro-(5E)-5-fluoro-CBA₂ compounds,
trans-2,3-didehydro-(5Z)-5-fluoro-CBA₂ compounds,
trans-2,3-didehydro-(5E)-9β-methyl-2,5-inter-o-phenylene-3,4-dinor-CBA₂ compounds,
trans-2,3-didehydro-(5Z)-9β-methyl-2,5-inter-o-phenylene-3,4-dinor-CBA₂ compounds,
trans-2,3-didehydro-(5E)-9β-methyl-1,5-inter-o-phenylene-2,3,4-trinor-CBA₂ compounds,
trans-2,3-didehydro-(5E)-9β-methyl-1,5-inter-o-phenylene-3,4,5-trinor-CBA₂ compounds,
trans-2,3-didehydro-(5E)-2,5-inter-o-phenylene-3,4-dinor-CBA₂ compounds,
trans-2,3-didehydro-(5Z)-2,5-inter-o-phenylene-3,4-dinor-CBA₂ compounds,
trans-2,3-didehydro-(5E)-1,5-inter-m-phenylene-2,3,4-trinor-CBA₂ compounds,
trans-2,3-didehydro-(5Z)-1,5-inter-m-phenylene-2,3,4-trinor-CBA₂ compounds,
9-deoxy-2',9α-methano-3-oxa-4,5,6-trinor-3,7-(1',3'-inter-phenylene)-PGF₁ compounds,
9-deoxy-2',9β-methano-3-oxa-4,5,6-trinor-3,7-(1',3'-inter-phenylene)-PGF₁ compounds,
9-deoxo-2',9-methano-3-oxa-3,4,5-trinor-3,7-(1',3'-inter-phenylene)-7,8-didehydro-PGE₁ compounds,
9-deoxo-2',9-metheno-3-oxa-3,4,5-trinor-3,7-(1',3'-inter-phenylene)-PGE₁ compounds,
6a-oxo-9-deoxy-2',9α-methano-3-oxa-4,5,6-trinor-3,7-(1',3'-inter-phenylene)-PGF₁ compounds,
6a-oxo-9-deoxy-2',9β-methano-3-oxa-4,5,6-trinor-3,7-(1',3'-inter-phenylene-PGF₁ compounds,
6aα-hydroxy-9-deoxy-2',9α-methano-3-oxa-4,5,6-trinor-3,7-(1',3'-inter-phenylene)-PGF₁ compounds,
6aα-hydroxy-9-deoxy-2',9β-methano-3-oxa-4,5,6-trinor-3,7-(1',3'-inter-phenylene)PGF₁ compounds,
6aβ-hydroxy-9-deoxy-2',9α-methano-3-oxa-4,5,6-trinor-3,7-(1',3'-inter-phenylene-PGF₁, and
6aα-hydroxy-9-deoxy-2',9β-methano-3-oxa-4,5,6-trinor-3,7-(1',3'-inter-phenylene)-PGF₁ compounds,
in free acid or methyl ester form which exhibit the following side chain substituents:
15-cyclohexyl-16,17,18,19,20-pentanor-;
17-(2-furyl)-18,19,20-trinor-;
16-(3-thienyl)oxy-17,18,19,20-tetranor-;
17-(3-thienyl)-18,19,20-trinor-;
15-methyl-;
16-methyl-;
15,16-dimethyl-;
16,16-dimethyl-;
17,20-dimethyl;
16-fluoro-;
15-methyl-16-fluoro-;
16,16-difluoro-;
15-methyl-16,16-difluoro-;
17-phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-methyl-17-phenyl-18,19,20-trinor-;
16-methyl-17-phenyl-18,19,20-trinor-;
16,16-dimethyl-17-phenyl-18,19,20-trinor-;
16-fluoro-17-phenyl-18,19,20-trinor-;
16,16-difluoro-17-phenyl-18,19,20-trinor-;
16-phenyl-17,18,19,20-tetranor-;
15-methyl-16-phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-phenyl-18,19,20-trinor-;
15-methyl-16-phenyl-18,19,20-trinor-;
16-methyl-16-phenyl-18,19,20-trinor-;
15,16-dimethyl-16-phenyl-18,19,20-trinor-;
16-phenoxy-17,18,19,20-tetranor-;
15-methyl-16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-phenoxy-18,19,20-trinor-;
15-methyl-16-phenoxy-18,19,20-trinor-;
16-methyl-16-phenoxy-18,19,20-trinor-;
15,16-dimethyl-16-phenoxy-18,19,20-trinor-;
13,14-didehydro-;
15-cyclohexyl-16,17,18,19,20-pentanor-13,14-didehydro-;
17-(2-furyl)-18,19,20-trinor-13,14-didehydro-;
16-(3-thienyl)oxy-17,18,19,20-tetranor-13,14-didehydro-;
17-(3-thienyl)-18,19,20-trinor-13,14-didehydro-;
15-methyl-13,14-didehydro-;
16-methyl-13,14-didehydro-;
15,16-dimethyl-13,14-didehydro-;
16,16-dimethyl-13,14-didehydro-;
17,20-dimethyl-13,14-didehydro-;
16-fluoro-13,14-didehydro-;
15-methyl-16-fluoro-13,14-didehydro-;
16,16-difluoro-13,14-didehydro-;
15-methyl-16,16-difluoro-13,14-didehydro-;
17-phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
15-methyl-17-phenyl-18,19,20-trinor-13,14-didehydro-;
16-methyl-17-phenyl-18,19,20-trinor-13,14-didehydro-;
16,16-dimethyl-17-phenyl-18,19,20-trinor-13,14-didehydro-;
16-fluoro-17-phenyl-18,19,20-trinor-13,14-didehydro-;
16,16-difluoro-17-phenyl-18,19,20-trinor-13,14-didehydro-;
16-phenyl-17,18,19,20-tetranor-13,14-didehydro-;
15-methyl-16-phenyl-17,18,19,20-tetranor-13,14-didehydro-;
16-(m-trifluoromethylphenyl)-17,18,19,20-tetranor-13,14-didehydro-;
16-(m-chlorophenyl)-17,18,19,20-tetranor-13,14-didehydro-;

16-(p-fluorophenyl)-17,18,19,20-tetranor-13,14-didehydro-;
16-phenyl-18,19,20-trinor-13,14-didehydro-;
15-methyl-16-phenyl-18,19,20-trinor-13,14-didehydro-;
16-methyl-16-phenyl-18,19,20-trinor-13,14-didehydro-;
15,16-dimethyl-16-phenyl-18,19,20-trinor-13,14-didehydro-;
16-phenoxy-17,18,19,20-tetranor-13,14-didehydro-;
15-methyl-16-phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
16-(p-fluorophenoxy)-17,18,19,20-tetranor-13,14-didehydro-;
16-phenoxy-18,19,20-trinor-13,14-didehydro-;
15-methyl-16-phenoxy-18,19,20-trinor-13,14-didehydro-;
16-methyl-16-phenoxy-18,19,20-trinor-13,14-didehydro-;
15,16-dimethyl-16-phenoxy-18,19,20-trinor-13,14-didehydro-;
13,14-dihydro-;
15-cyclohexyl-16,17,18,19,20-pentanor-13,14-dihydro-;
17-(2-furyl)-18,19,20-trinor-13,14-dihydro-;
16-(3-thienyl)oxy-17,18,19,20-tetranor-13,14-dihydro-;
17-(3-thienyl)-18,19,20-trinor-13,14-dihydro-;
15-methyl-13,14-dihydro-;
16-methyl-13,14-dihydro-;
15,16-dimethyl-13,14-dihydro-;
16,16-dimethyl-13,14-dihydro-;
17,20-dimethyl-13,14-dihydro-;
16-fluoro-13,14-dihydro-;
15-methyl-16-fluoro-13,14-dihydro-;
16,16-difluoro-13,14-dihydro-;
15-methyl-16,16-difluoro-13,14-dihydro-;
17-phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
15-methyl-17-phenyl-18,19,20-trinor-13,14-dihydro-;
16-methyl-17-phenyl-18,19,20-trinor-13,14-dihydro-;
16,16-dimethyl-17-phenyl-18,19,20-trinor-13,14-dihydro-;
16-fluoro-17-phenyl-18,19,20-trinor-13,14-dihydro-;
16,16-difluoro-17-phenyl-18,19,20-trinor-13,14-dihydro-;
16-phenyl-17,18,19,20-tetranor-13,14-dihydro-;
15-methyl-16-phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-phenyl-18,19,20-trinor-13,14-dihydro-;
15-methyl-16-phenyl-18,19,20-trinor-13,14-dihydro-;
16-methyl-16-phenyl-18,19,20-trinor-13,14-dihydro-;
15,16-dimethyl-16-phenyl-18,19,20-trinor-13,14-dihydro-;
16-phenoxy-17,18,19,20-tetranor-13,14-dihydro-;
15-methyl-16-phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-phenoxy-18,19,20-trinor-13,14-dihydro-;
15-methyl-16-phenoxy-18,19,20-trinor-13,14-dihydro-;
16-methyl-16-phenoxy-18,19,20-trinor-13,14-dihydro-;
15,16-dimethyl-16-phenoxy-18,19,20-trinor-13,14-dihydro-;
13-cis-;
15-cyclohexyl-16,17,18,19,20-pentanor-13-cis-;
17-(2-furyl)-18,19,20-trinor-13-cis-;
16-(3-thienyl)oxy-17,18,19,20-tetranor-13-cis-;
17-(3-thienyl)-18,19,20-trinor-13-cis-;
15-methyl-13-cis-;
16-methyl-13-cis-;
15,16-dimethyl-13-cis-;
16,16-dimethyl-13-cis-;
17,20-dimethyl-13-cis-;
16-fluoro-13-cis-;
15-methyl-16-fluoro-13-cis-;
16,16-difluoro-13-cis-;
15-methyl-16,16-difluoro-13-cis-;
17-phenyl-18,19,20-trinor-13-cis-;
17-(m-trifluoromethylphenyl)-18,19,20-trinor-13-cis-;
17-(m-chlorophenyl)-18,19,20-trinor-13-cis-;
17-(p-fluorophenyl)-18,19,20-trinor-13-cis-;
15-methyl-17-phenyl-18,19,20-trinor-13-cis-;
16-methyl-17-phenyl-18,19,20-trinor-13-cis-;
16,16-dimethyl-17-phenyl-18,19,20-trinor-13-cis-;
16-fluoro-17-phenyl-18,19,20-trinor-13-cis-;
16,16-difluoro-17-phenyl-18,19,20-trinor-13-cis-;
16-phenyl-17,18,19,20-tetranor-13-cis-;
15-methyl-16-phenyl-17,18,19,20-tetranor-13-cis-;
16-(m-trifluoromethylphenyl)-17,18,19,20-tetranor-13-cis-;
16-(m-chlorophenyl)-17,18,19,20-tetranor-13-cis-;
16-(p-fluorophenyl)-17,18,19,20-tetranor-13-cis-;
16-phenyl-18,19,20-trinor-13-cis-;
15-methyl-16-phenyl-18,19,20-trinor-13-cis-;
16-methyl-16-phenyl-18,19,20-trinor-13-cis-;
15,16-dimethyl-16-phenyl-18,19,20-trinor-13-cis-;
16-phenoxy-17,18,19,20-tetranor-13-cis-;
15-methyl-16-phenoxy-17,18,19,20-tetranor-13-cis-;
16-(m-trifluoromethylphenoxy)-17,18,19,20-tetranor-13-cis-;
16-(m-chlorophenoxy)-17,18,19,20-tetranor-13-cis-;
16-(p-fluorophenoxy)-17,18,19,20-tetranor-13-cis-;
16-phenoxy-18,19,20-trinor-13-cis-;
15-methyl-16-phenoxy-18,19,20-trinor-13-cis-;
16-methyl-16-phenoxy-18,19,20-trinor-13-cis-; and
15,16-dimethyl-16-phenoxy-18,19,20-trinor-13-cis-.

FORMULAS

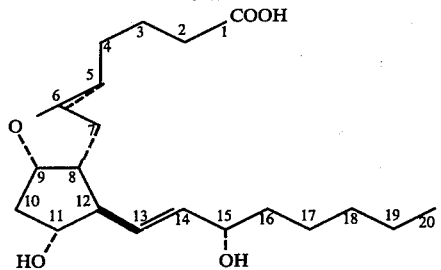

I

-continued
FORMULAS
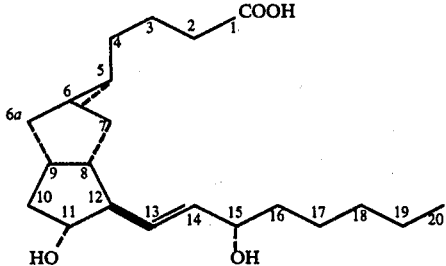
II
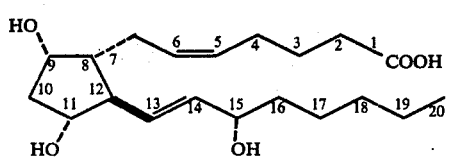
III
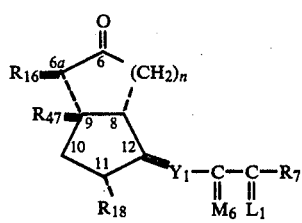
IV
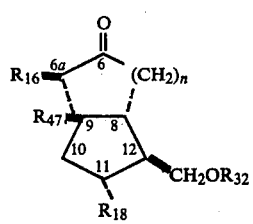
V
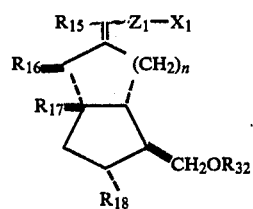
VI
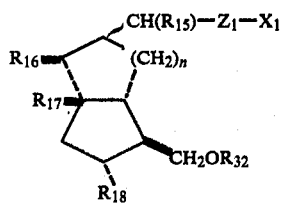
VII
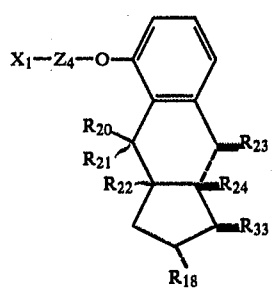
VIII
-continued
FORMULAS
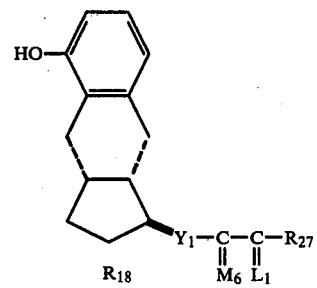
IX
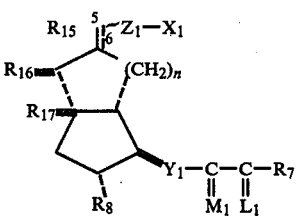
X
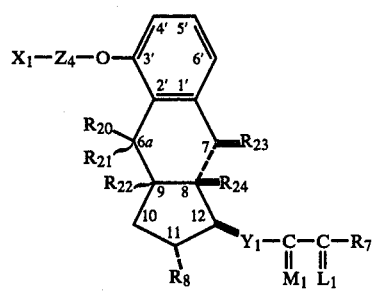
XI
CHART A
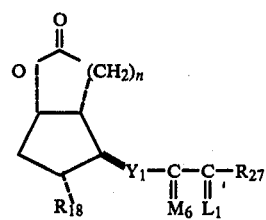
XXI
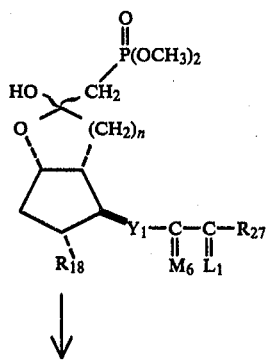
XXII

CHART A
-continued
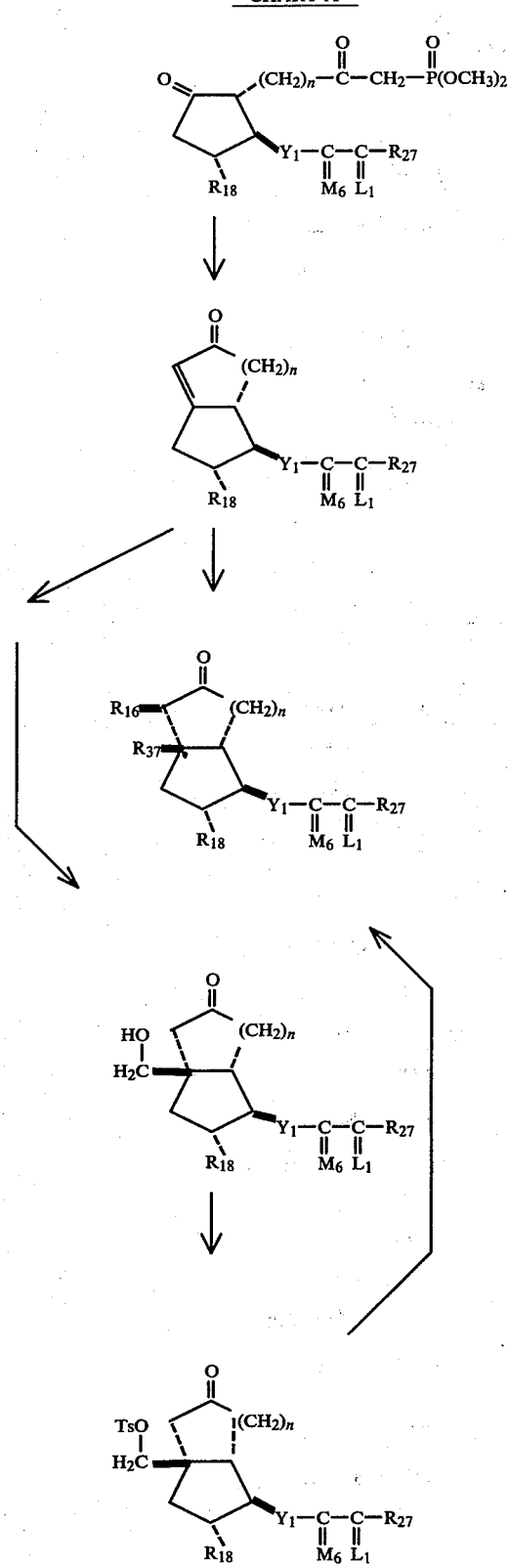
CHART B
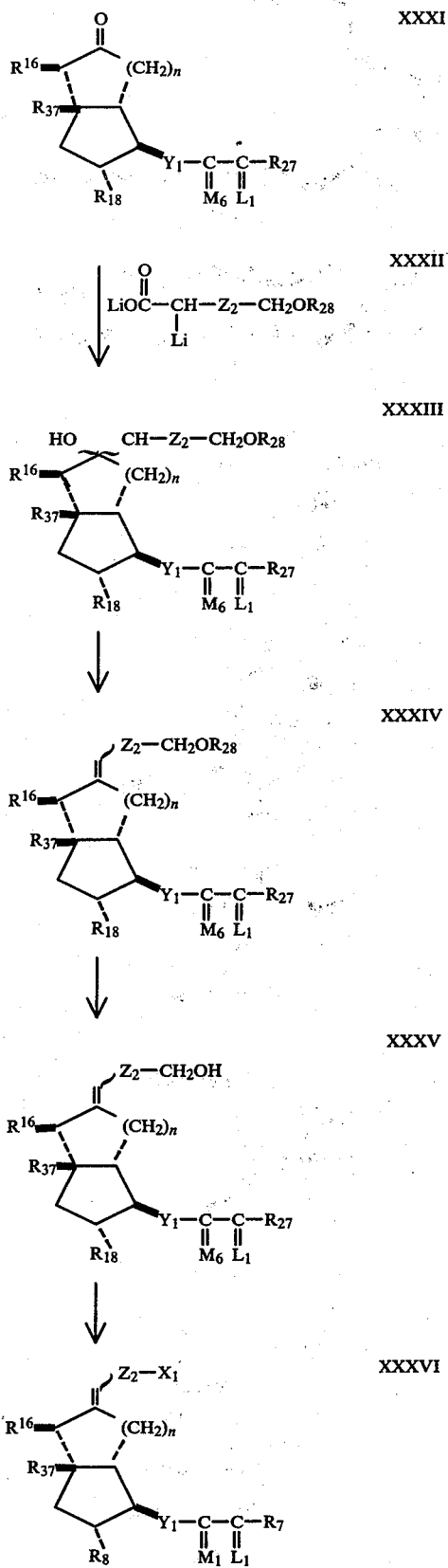

CHART C
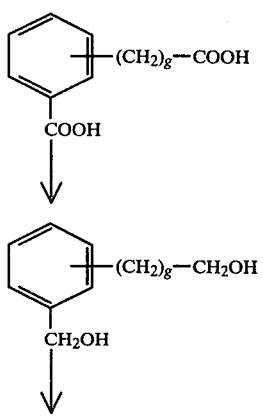
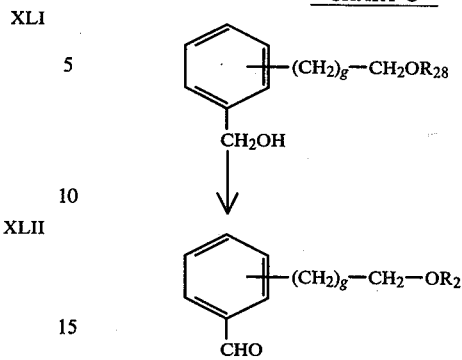
CHART D
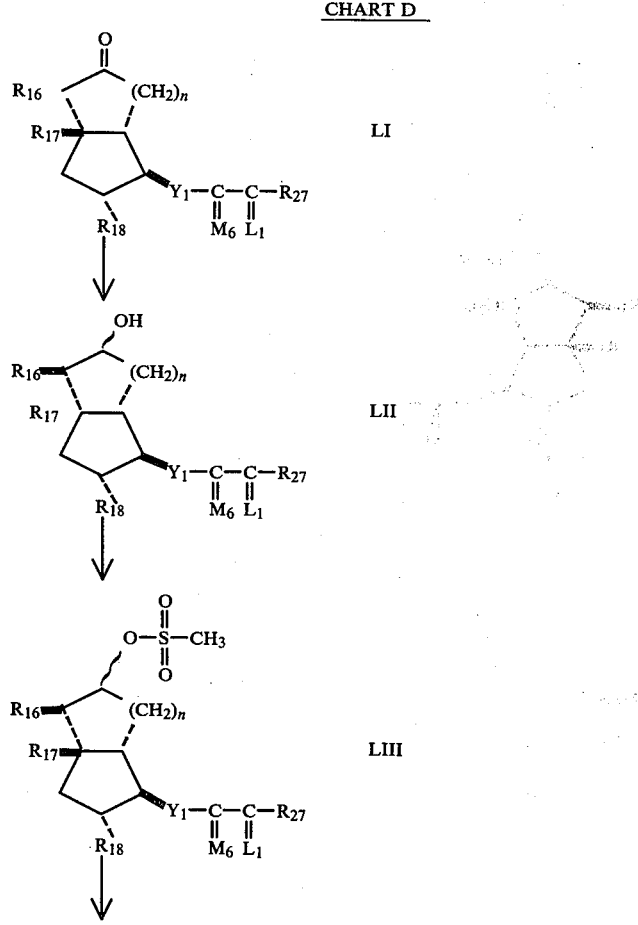

CHART D
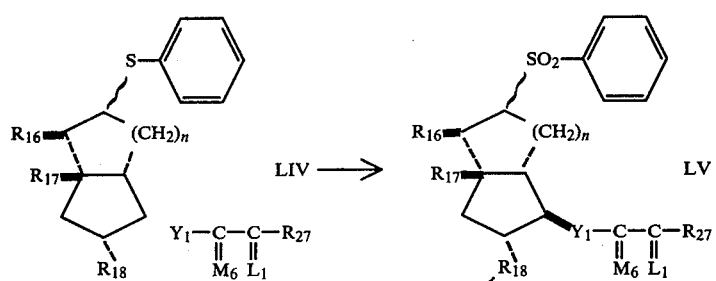
LIV ⟶
LV
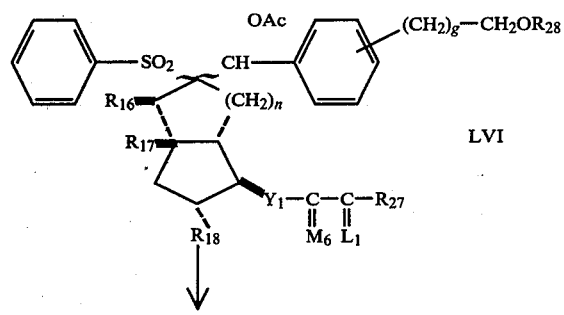
LVI
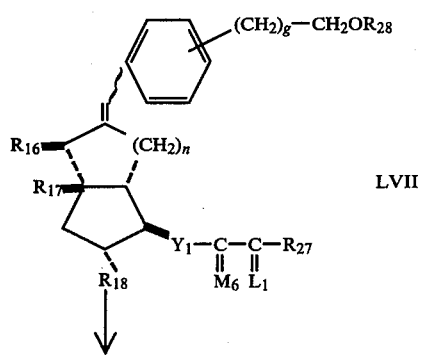
LVII
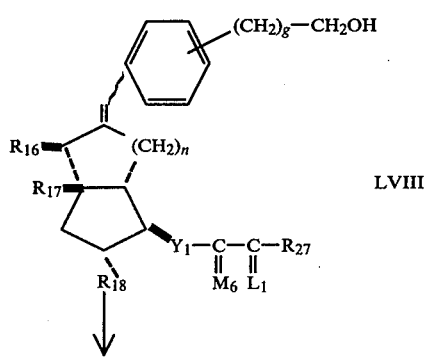
LVIII

CHART D
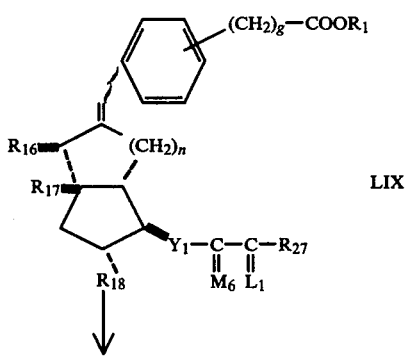
CHART E
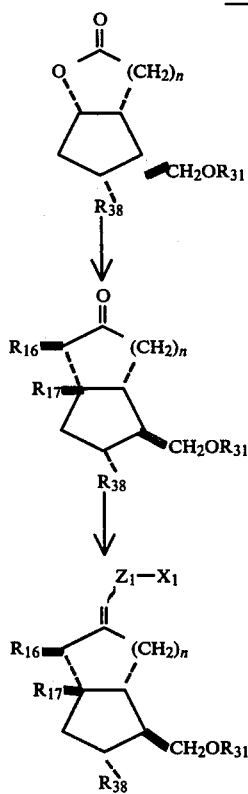
CHART F
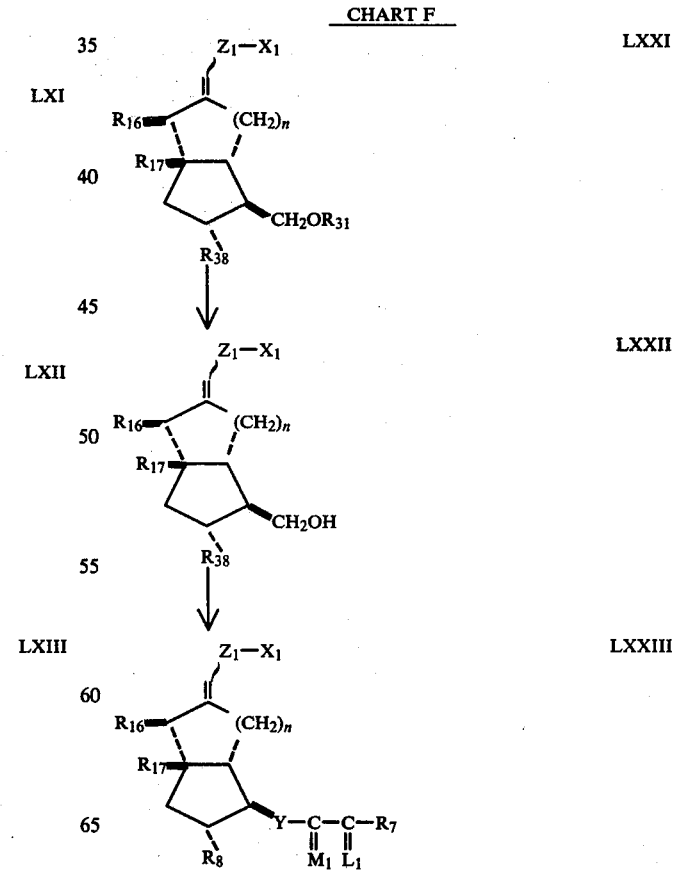

CHART G
 LXXXI
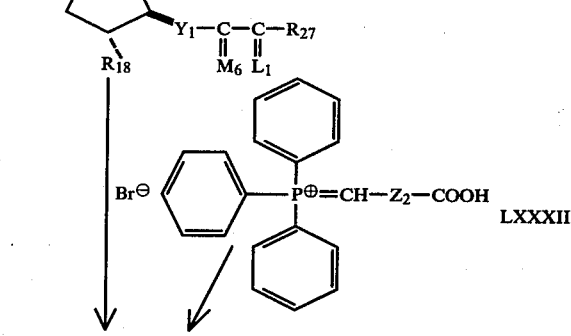 LXXXII
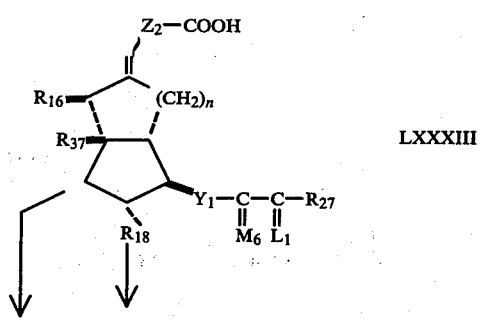 LXXXIII
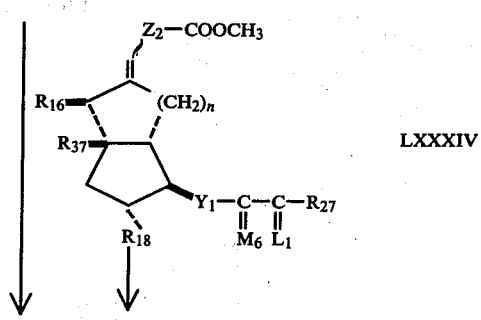 LXXXIV
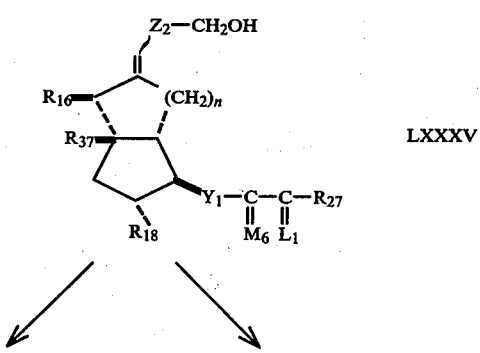 LXXXV -continued
CHART G
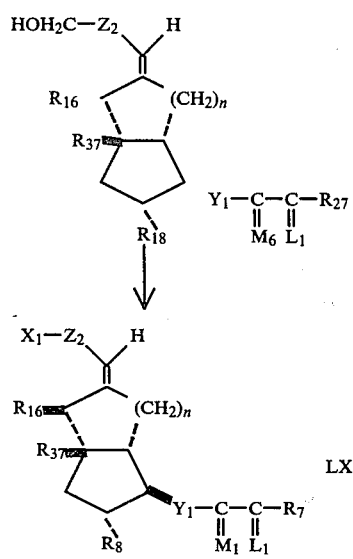
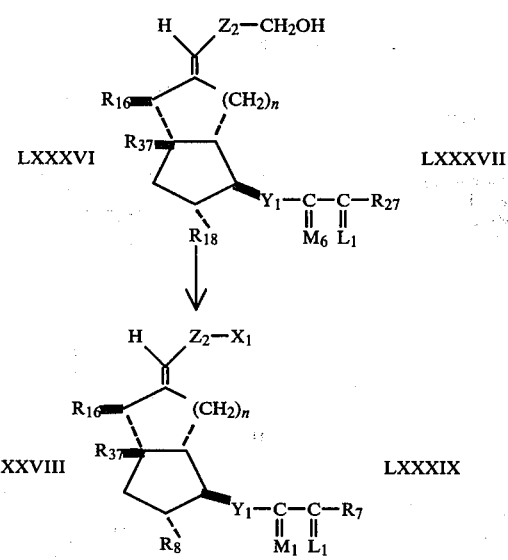
CHART H
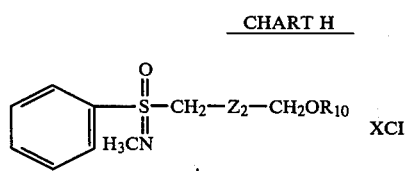
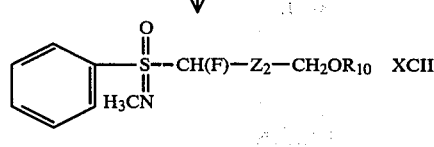
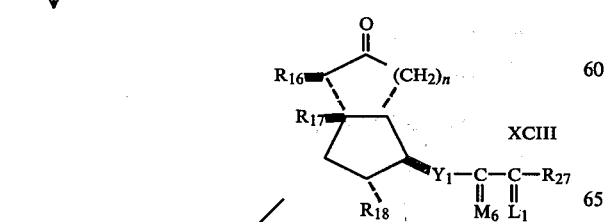
-continued
CHART H -continued
CHART H
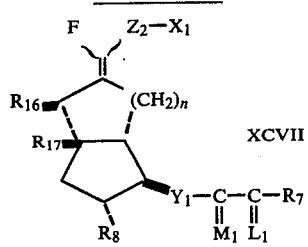
XCVII
CHART I
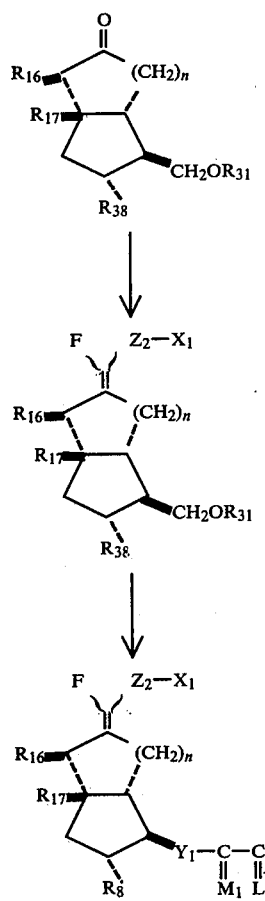
-continued
CHART J
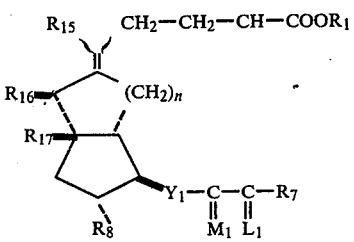
CXII
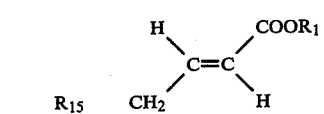
CXIII
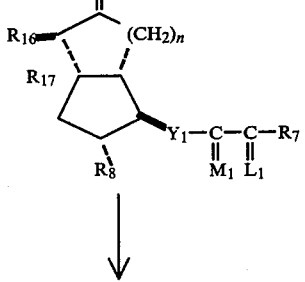
CXIV
CHART J
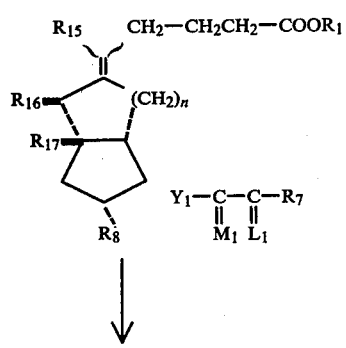
CXI
CHART K
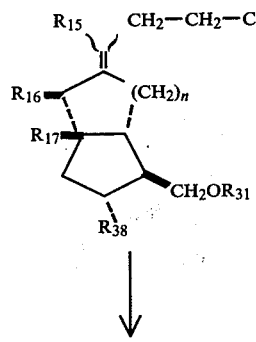
CXXI -continued
CHART K
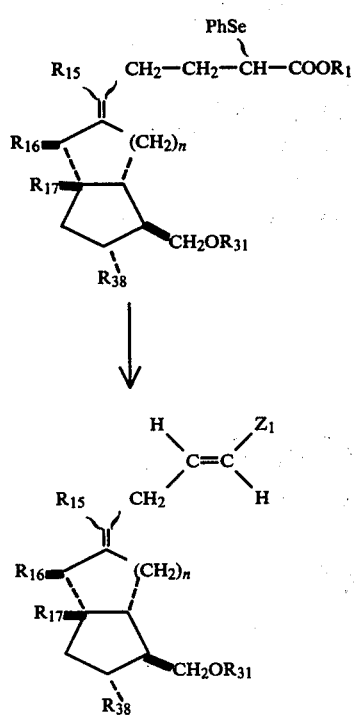
CXXII
CXXIII
CHART L
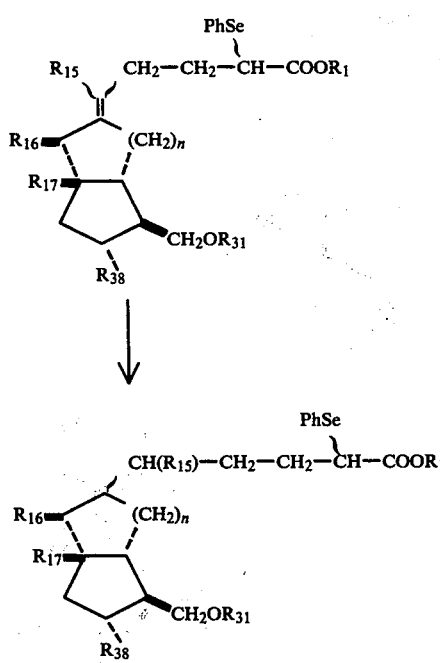
CXXXI
CXXXII
CHART L
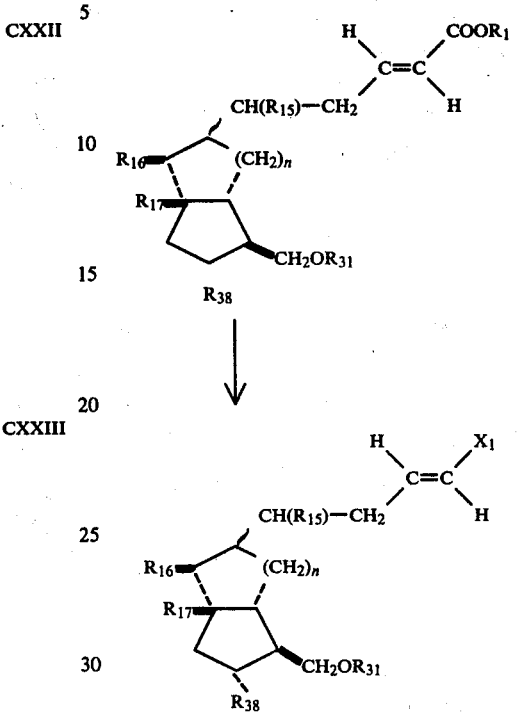
CXXXIII
CXXXIV
CHART M
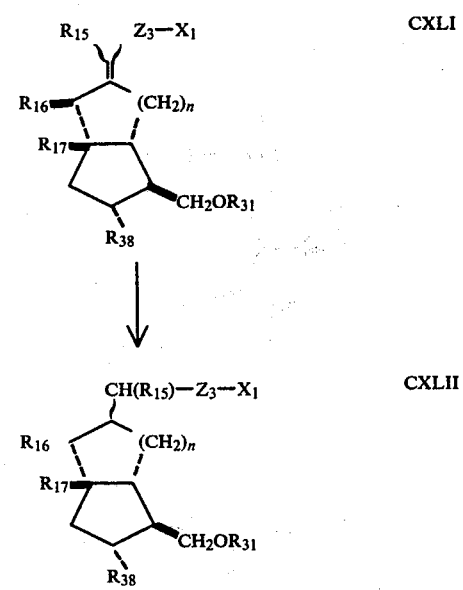
CXLI
CXLII
CHART N -continued
CHART N
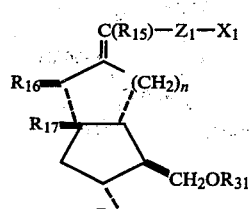
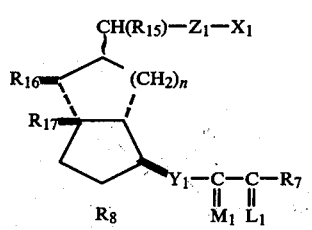
CHART O
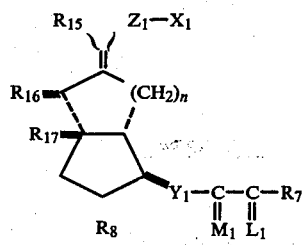
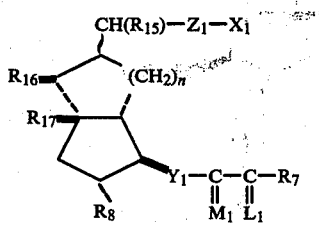
CHART P
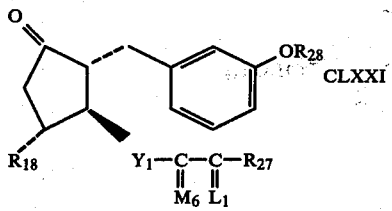
↓
-continued
CHART P
CLI 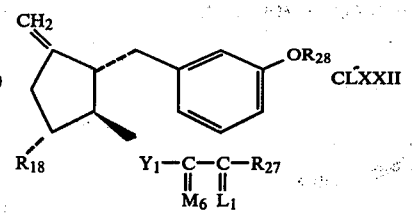
↓
CLII 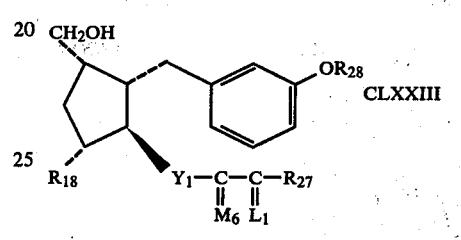
↓
CLXI 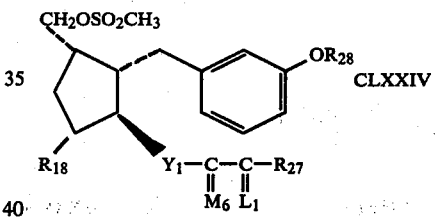
↓
CLXII 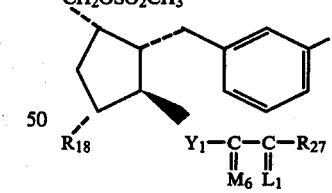
→
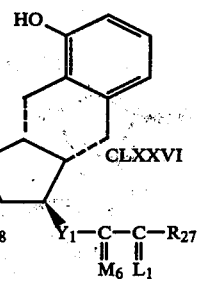
↓

4,420,632
-continued
CHART P
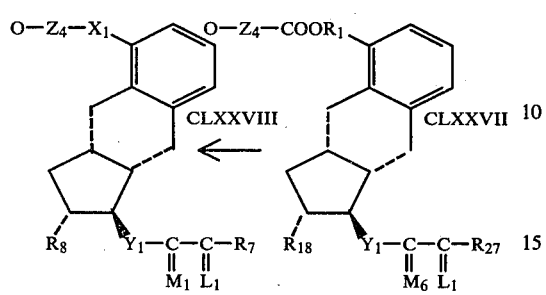
CHART Q
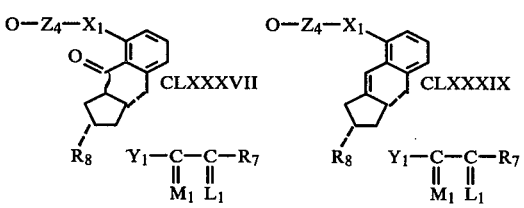
CHART Q
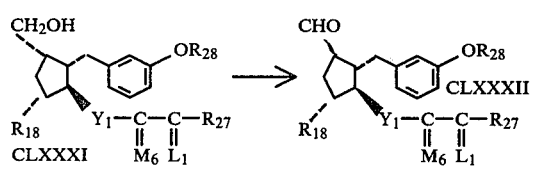
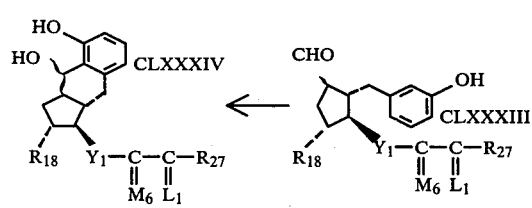
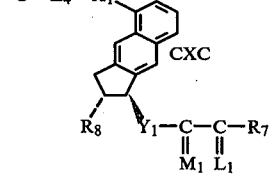
CHART R
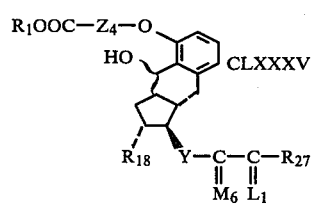
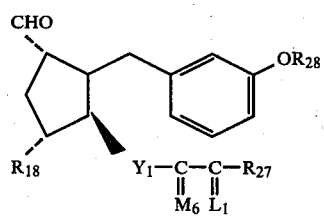
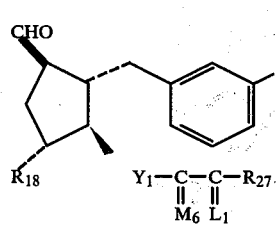
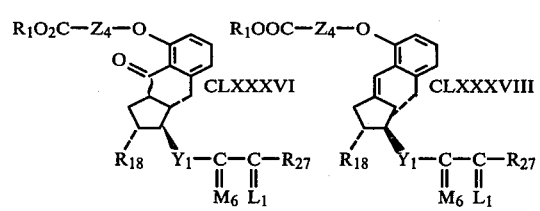
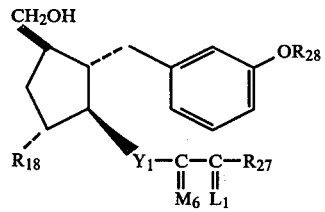

-continued
CHART R
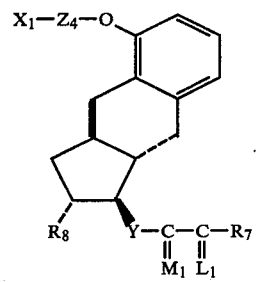
CXCIV
CHART S
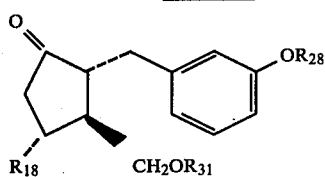
CCI
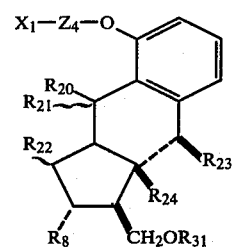
CCII
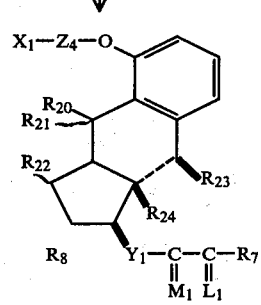
CCIII
CHART T
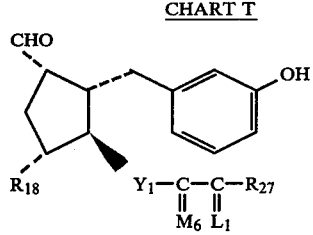
CCXI
-continued
CHART T
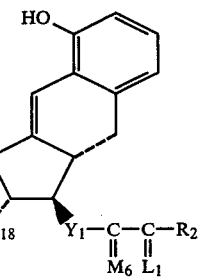
CCXII
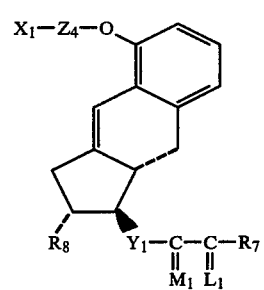
CCXIII
CHART U
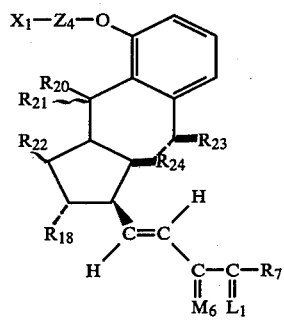
CCXXI
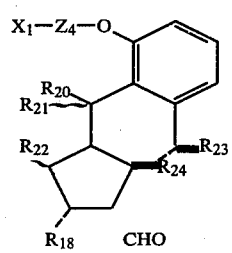
CCXXII -continued
CHART U

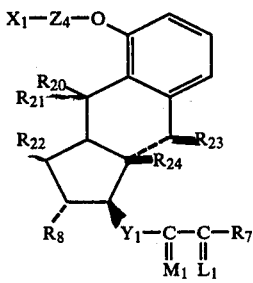

CCXXIII

I claim:
1. A carbacyclin analog of formula X:

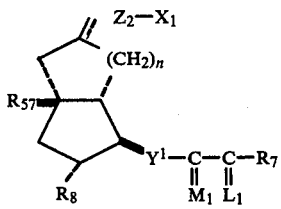

X wherein n is one or 2;
wherein $L_1$ is $\alpha\text{-}R_3\text{:}\beta\text{-}R_4$, $\alpha\text{-}R_4\text{:}\beta\text{-}R_3$, or a mixture of $\alpha\text{-}R_3\text{:}\beta\text{-}R_4$ and $\alpha\text{-}R_4\text{:}\beta\text{-}R_3$, wherein $R_3$ and $R_4$ are hydrogen, methyl, or fluoro, being the same or different, with the proviso that one of $R_3$ and $R_4$ is fluoro only when the other is hydrogen or fluoro;
wherein $M_1$ is $\alpha\text{-}OH\text{:}\beta\text{-}R_5$ or $\alpha\text{-}R_5\text{:}\beta\text{-}OH$, wherein $R_5$ is hydrogen or methyl;
wherein $R_7$ is
(1) $-C_mH_{2m}-CH_3$, wherein m is an integer from one to 5, inclusive,
(2) phenoxy optionally substituted by one, two or three chloro, fluoro, trifluoromethyl, $(C_1\text{-}C_3)$alkyl, or $(C_1\text{-}C_3)$alkoxy, with the proviso that not more than two substituents are other than alkyl, with the proviso that $R_7$ is phenoxy or substituted phenoxy, only when $R_3$ and $R_4$ are hydrogen or methyl, being the same or different,
(3) phenyl, benzyl, phenylethyl, or phenylpropyl optionally substituted on the aromatic ring by one, two or three chloro, fluoro, trifluoromethyl, $(C_1\text{-}C_3)$alkyl, or $(C_1\text{-}C_3)$alkoxy, with the prosivo that not more than two substituents are other than alkyl,
(4) cis—$CH=CH-CH_2-CH_3$,
(5) $-(CH_2)_2-CH(OH)-CH_3$, or
(6) $-(CH_2)_3-CH=C(CH_3)_2$;
wherein $-C(L_1)-R_7$ taken together is
(1) $(C_4\text{-}C_7)$cycloalkyl optionally substituted by one to 3 $(C_1\text{-}C_5)$alkyl;
(2) 2-(2-furyl)ethyl,
(3) 2-(3-thienyl)ethoxy, or
(4) 3-thienyloxymethyl;
wherein $R_8$ is hydroxy, hydroxymethyl, or hydrogen;
wherein $R_{57}$ is $(C_1\text{-}C_4)$alkyl;
wherein $X_1$ is
(1) $-COOR_1$, wherein $R_1$ is
(a) hydrogen,
(b) $(C_1\text{-}C_{12})$alkyl,
(c) $(C_3\text{-}C_{10})$cycloalkyl,
(d) $(C_7\text{-}C_{12})$aralkyl,
(e) phenyl, optionally substituted with one, 2 or 3 chloro or $(C_1\text{-}C_3)$alkyl,
(f) phenyl substituted in the para position by (i) $-NH-CO-R_{25}$,
(ii) $-CO-R_{26}$,
(iii) $-O-CO-R_{54}$, or
(iv) $-CH=N-NH-CO-NH_2$ wherein $R_{25}$ is methyl, phenyl, acetamidophenyl, benzamidophenyl, or $-N_2$; $R_{26}$ is methyl, phenyl, $-NH_2$, or methoxy; and $R_{54}$ is phenyl or acetamidophenyl; inclusive, or
(g) a pharmacologically acceptable cation;
(2) $-CH_2OH$,
(3) $-COL_4$, wherein $L_4$ is
(a) amino of the formula $-NR_{51}R_{52}$, wherein $R_{51}$ and $R_{52}$ are
(i) hydrogen,
(ii) $(C_1\text{-}C_{12})$alkyl,
(iii) $(C_3\text{-}C_{10})$cycloalkyl,
(iv) $(C_7\text{-}C_{12})$aralkyl,
(v) phenyl, optionally substituted with one, 2 or 3 chloro, $(C_1\text{-}C_3)$alkyl, hydroxy, carboxy, $(C_2\text{-}C_5)$alkoxycarbonyl, or nitro,
(vi) $(C_2\text{-}C_5)$carboxyalkyl,
(vii) $(C_2\text{-}C_5)$carbamoylalkyl,
(viii) $(C_2\text{-}C_5)$cyanoalkyl,
(ix) $(C_3\text{-}C_6)$acetylalkyl,
(x) $(C_7\text{-}C_{11})$benzoalkyl, optionally substituted by one, 2 or 3 chloro, $(C_1\text{-}C_3)$alkyl, hydroxy, $(C_1\text{-}C_3)$alkoxy, carboxy, $(C_2\text{-}C_5)$alkoxycarbonyl, or nitro,
(xi) pyridyl, optionally substituted by one, 2 or 3 chloro, $(C_1\text{-}C_3)$alkyl, or $(C_1\text{-}C_3)$alkoxy,
(xii) $(C_6\text{-}C_9\text{-pyridylalkyl}$ optionally substituted by one, 2 or 3 chloro, $(C_1\text{-}C_3)$alkyl, hydroxy, or $(C_1\text{-}C_3)$alkyl,
(xiii) $(C_1\text{-}C_4)$hydroxyalkyl,
(xiv) $(C_1\text{-}C_4)$dihydroxyalkyl,
(xv) $(C_1\text{-}C_4)$trihydroxyalkyl,
with the further proviso that not more than one of $R_{51}$ and $R_{52}$ is other than hydrogen or alkyl,
(b) cycloamino selected from the group consisting of pyrolidino, piperidino, morpholino, piperazino, hexamethyleneimino, pyrrolino, or 3,4-didehydropiperidinyl optionally substituted by one or 2 $(C_1\text{-}C_{12})$alkyl of one to 12 carbon atoms, inclusive,
(c) carbonylamino of the formula $-NR_{53}COR_{51}$, wherein $R_{53}$ is hydrogen or $(C_1\text{-}C_4)$alkyl and $R_{51}$ is other than hydrogen, but otherwise as defined above,
(d) sulfonylamino of the formula $-NR_{53}SO_2R_{51}$, wherein $R_{51}$ and $R_{53}$ are as defined in (c),
(4) $-CH_2NL_2L_3$, wherein $L_2$ and $L_3$ are hydrogen or $(C_1\text{-}C_4)$-alkyl, being the same or different, or the pharmacologically acceptable acid addition salts thereof when $X_1$ is $-CH_2NL_2L_3$,
wherein $Y_1$ is trans—$CH=CH-$, cis—$CH=CH-$, $-CH_2CH_2-$, or $-C\equiv C-$; and
wherein $Z_2$ is
(1) $-CH_2-(CH_2)_f-C(R_2)_2$, wherein $R_2$ is hydrogen or fluoro and f is zero, one, 2, or 3, or
(2) trans—$CH_2-CH=CH-$.
2. (5E)-9$\beta$-methyl-CBA$_2$, a carbacyclin analog according to claim 1.
3. (5Z)-9$\beta$-methyl-CBA$_2$, a carbacyclin analog according to claim 1.
4. (5E)-9$\beta$-methyl-CBA$_2$, methyl ester, a carbacyclin analog according to claim 1.
5. (5Z)-9$\beta$-methyl-CBA$_2$, methyl ester, a carbacyclin analog according to claim 1.
6. A carbacyclin compound of claim 1 which is (5Z)-9$\beta$-methyl-CBA$_2$ calcium salt hydrate.

* * * * *

UNITED STATES PATENT OFFICE
CERTIFICATE OF CORRECTION

Patent No. 4,420,632            Dated   December 13, 1983

Inventor(s)  Paul A. Aristoff

It is certified that error appears in the above-identified patent and that said Letters Patent are hereby corrected as shown below:

Column 3, line 6, "Facial" should read -- Facile --.

Column 35, line 45, "-]β-" should read -- -9β- --.

Column 35, line 47, "$Z_2$, $R_{18}$" should read -- $Z_2$, n, $R_{18}$ --.

Column 45, line 11, "Example 14 is 15 ml" should read -- Example 14 in 15 ml --.

Column 47, line 21, "4.93δ" should read -- 5.93δ --.

Column 60, line 63, "1126" should read -- 1125 --.

Column 61, line 32, "-oxo-4,5,6-" should read -- -oxa-4,5,6- --.

Column 62, line 64, "1-(t-" should read -- 3-(t- --.

Column 74, Formulas, lower portion of Formula IX should appear as follows:

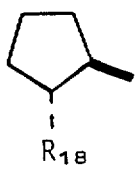

Column 74, Formulas, upper portion of Formula X should appear as follows:

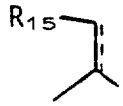

UNITED STATES PATENT OFFICE
CERTIFICATE OF CORRECTION

Patent No. 4,420,632      Dated  December 13, 1983

Inventor(s)  Paul A. Aristoff

It is certified that error appears in the above-identified patent and that said Letters Patent are hereby corrected as shown below:

Column 74, Chart A, upper portion of Formula XXI should appear as follows:

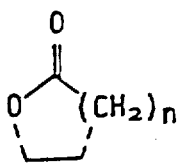

Column 78, Chart D, Formula LII should appear as follows:

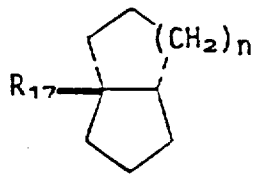

Column 79, Chart D, lower portion of Formula LIV should appear as follows:

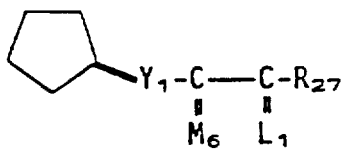

Column 79, Chart D, upper right portion of Formula LVI should appear as follows:

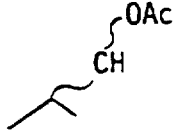

UNITED STATES PATENT OFFICE
CERTIFICATE OF CORRECTION

Patent No. 4,420,632  Dated December 13, 1983

Inventor(s) Paul A. Aristoff

It is certified that error appears in the above-identified patent and that said Letters Patent are hereby corrected as shown below:

Column 81, Chart E, lower portion of Formula LXI should appear as follows:

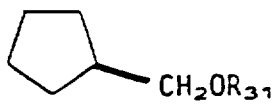

Column 85, Chart G, Formula LXXXVI should appear as follows:

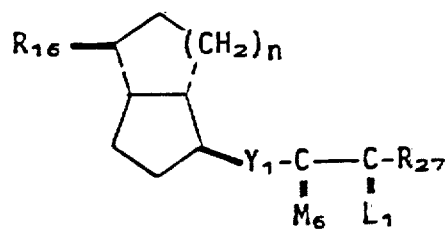

Column 85, Chart H, Formula XCII should appear as follows:

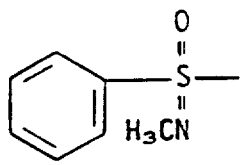

UNITED STATES PATENT OFFICE
CERTIFICATE OF CORRECTION

Patent No. 4,420,632  Dated December 13, 1983

Inventor(s) Paul A. Aristoff

It is certified that error appears in the above-identified patent and that said Letters Patent are hereby corrected as shown below:

Column 88, Chart J, upper portion of Formula CXII should appear as follows:

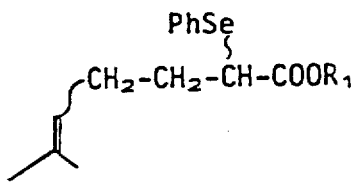

Column 90, Chart L, lowermost portion of Formula CXXXIII should appear as follows:

Column 90, Chart M, upper portion of Formula CXLII should appear as follows:

UNITED STATES PATENT OFFICE
CERTIFICATE OF CORRECTION

Patent No. 4,420,632　　　　Dated December 13, 1983

Inventor(s) Paul A. Aristoff

It is certified that error appears in the above-identified patent and that said Letters Patent are hereby corrected as shown below:

Column 91, Chart N, lower portion of Formula CLII should appear as follows:

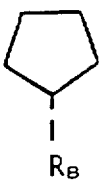

Column 91, Chart O, lower portion of Formula CLXI should appear as follows:

Column 93, Chart P, uppermost portion of Formula CLXXVII should appear as follows:

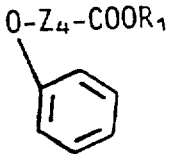

Column 93, Chart P, uppermost portion of Formula CLXXVIII should appear as follows:

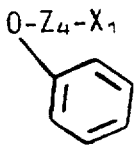

UNITED STATES PATENT OFFICE
CERTIFICATE OF CORRECTION

Patent No. 4,420,632  Dated December 13, 1983

Inventor(s)

It is certified that error appears in the above-identified patent and that said Letters Patent are hereby corrected as shown below:

Column 93, Chart Q, leftmost portion of Formula CLXXXIII should appear as follows:

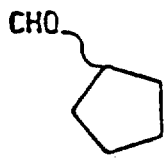

Column 94, Chart Q, uppermost portion of Formula CLXXXVII should appear as follows:

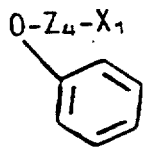

Column 94, Chart Q, lowermost portion of Formula CLXXXVII should appear as follows:

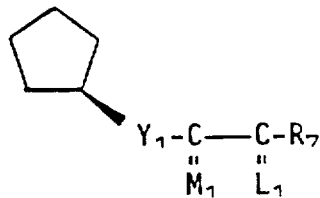

Column 94, Chart Q, uppermost portion of Formula CLXXXIX should appear as follows:

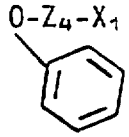

UNITED STATES PATENT OFFICE
CERTIFICATE OF CORRECTION

Patent No. 4,420,632    Dated December 13, 1983

Inventor(s) Paul A. Aristoff

It is certified that error appears in the above-identified patent and that said Letters Patent are hereby corrected as shown below:

Column 94, Chart Q, lowermost portion of Formula CLXXXIX should appear as follows:

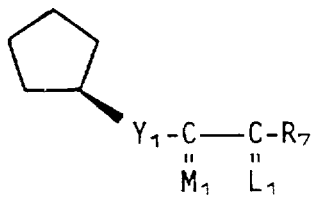

Column 94, Chart Q, uppermost portion of Formula CXC should appear as follows:

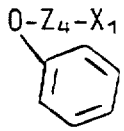

Column 95, Chart S, Formula CCII, $R_{22}$ bond should appear as follows:

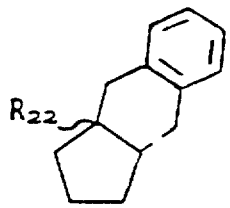

UNITED STATES PATENT OFFICE
CERTIFICATE OF CORRECTION

Patent No. 4,420,632  Dated December 13, 1983

Inventor(s) Paul A. Aristoff

It is certified that error appears in the above-identified patent and that said Letters Patent are hereby corrected as shown below:

Column 95, Chart S, Formula CCIII, $R_{22}$ bond should appear as follows:

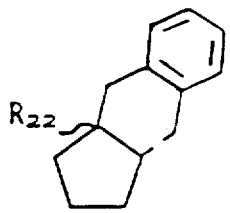

Column 96, Chart U, Formula CCXXI, $R_{22}$ bond should appear as follows:

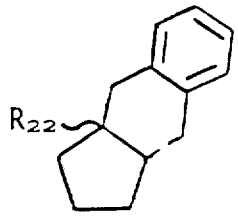

Column 96, Chart U, Formula CCXXII, $R_{22}$ bond should appear as follows:

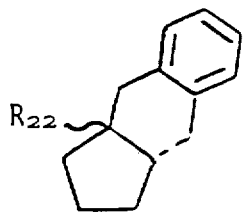

UNITED STATES PATENT OFFICE
CERTIFICATE OF CORRECTION

Patent No. 4,420,632                    Dated  December 13, 1983

Inventor(s)  Paul A. Aristoff

It is certified that error appears in the above-identified patent and that said Letters Patent are hereby corrected as shown below:

Column 97, Chart U, Formula CCXXIII, $R_{22}$ bond should appear as follows:

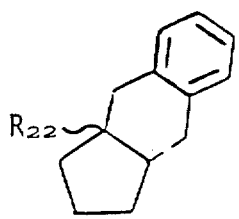

Column 97, Claim 1, uppermost portion of Formula X should appear as follows:

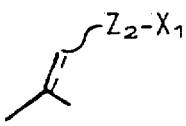

Signed and Sealed this

Twenty-first Day of January 1986

[SEAL]

Attest:

DONALD J. QUIGG

Attesting Officer          Commissioner of Patents and Trademarks